(12) United States Patent
Suka et al.

(10) Patent No.: US 10,472,377 B2
(45) Date of Patent: Nov. 12, 2019

(54) METHOD FOR PRODUCING POLYALKYLENE GLYCOL DERIVATIVE HAVING AMINO GROUP AT END, POLYMERIZATION INITIATOR FOR USE IN THE SAME, AND ALCOHOL COMPOUND AS RAW MATERIAL FOR THE POLYMERIZATION INITIATOR

(71) Applicant: Shin-Etsu Chemical Co., Ltd., Tokyo (JP)

(72) Inventors: Yuki Suka, Joetsu (JP); Yuji Harada, Joetsu (JP); Takeru Watanabe, Joetsu (JP); Shiori Nonaka, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/621,272

(22) Filed: Jun. 13, 2017

(65) Prior Publication Data
US 2017/0275305 A1 Sep. 28, 2017

Related U.S. Application Data

(62) Division of application No. 14/959,318, filed on Dec. 4, 2015, now Pat. No. 9,708,350.

(30) Foreign Application Priority Data

Dec. 4, 2014 (JP) .................................. 2014246046
Jul. 30, 2015 (JP) .................................. 2015151012

(51) Int. Cl.
C07F 7/10 (2006.01)
C08G 65/26 (2006.01)
C08G 65/329 (2006.01)

(52) U.S. Cl.
CPC ............ C07F 7/10 (2013.01); C08G 65/2609 (2013.01); C08G 65/2618 (2013.01);
(Continued)

(58) Field of Classification Search
None
See application file for complete search history.

(56) References Cited

U.S. PATENT DOCUMENTS 4,504,622 A 3/1985 Schmitt
5,021,585 A 6/1991 Dougherty et al.
(Continued)

FOREIGN PATENT DOCUMENTS

EP 0555101 A2 8/1993
EP 1167418 A1 1/2002
(Continued)

OTHER PUBLICATIONS

European Examination Report corresponding to European Application No. 15197846.7, dated Jul. 25, 2017. 7 pp.
Yokoyama et al. "Synthesis of Poly(ethylene oxide) with Heterobifunctional Reactive Groups at Its Terminals by an Anionic Initiator", *Bioconjugate Chem.* 3:275-276 (1992).
Extended European Search Report corresponding to European Application No. 15197846.7 dated Jul. 7, 2016.
Extended European Search Report corresponding to European Application No. 15197844.2 dated Aug. 9, 2016.
Jia et al., Synthesis of Poly(Ethylene Glycol) with Sulfadiazine and Chlorambucil End Groups and Investigation of Its Antitumor Activity, Bioorganic & Medicinal Chemistry Letters 13 (2003) 2531-2534.
(Continued)

*Primary Examiner* — Clinton A Brooks
*Assistant Examiner* — Kofi Adzamli
(74) *Attorney, Agent, or Firm* — Myers Bigel, P.A.

(57) ABSTRACT

A method for producing a narrowly distributed and high-purity polyalkylene glycol derivative having an amino group at an end, a polymerization initiator for use in the method, and a precursor of the polymerization initiator are provided.

The present invention provides: a method for producing a polyalkylene glycol derivative having an amino group at an end, using, as a polymerization initiator, a compound represented by the general formula (I); a compound represented by the following general formula (I); and a precursor thereof:

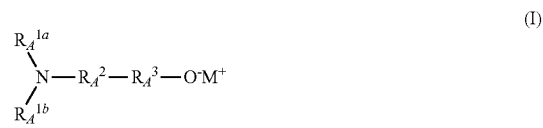

wherein $R_A^{1a}$ and $R_A^{1b}$ each independently represent a protective group of the amino group, or one of $R_A^{1a}$ and $R_A^{1b}$ represents H and the other represents a protective group of the amino group, or $R_A^{1a}$ and $R_A^{1b}$ bind to each other to represent a cyclic protective group forming a ring; $R_A^2$ represents a linear, branched, or cyclic hydrocarbon group having 1 to 6 carbon atoms; $R_A^3$ represents a single bond, or a linear, branched, or cyclic hydrocarbon group having 1 to 20 carbon atoms, and the hydrocarbon group may contain a heteroatom; the total number of carbon atoms (or the total number of carbon atoms and heteroatoms) of $R_A^2$ and $R_A^3$ is 4 or more; and M represents an alkali metal.

3 Claims, No Drawings

(52) U.S. Cl.
CPC ....... *C08G 65/2639* (2013.01); *C08G 65/329* (2013.01); *Y02P 20/55* (2015.11)

(56) References Cited

U.S. PATENT DOCUMENTS

| | | | |
|---|---|---|---|
| 5,483,008 A * | 1/1996 | Sakurai | C08G 65/2639 525/408 |
| 5,510,103 A | 4/1996 | Yokoyama et al. | |
| 6,388,041 B1 * | 5/2002 | Kataoka | C08G 63/6852 528/14 |
| 6,455,639 B1 | 9/2002 | Yasukohchi et al. | |
| 2001/0000510 A1 | 4/2001 | Sakurai et al. | |
| 2006/0074200 A1 | 4/2006 | Daugs et al. | |
| 2007/0088081 A1 | 4/2007 | Phanstiel | |
| 2008/0188638 A1 * | 8/2008 | Breitenkamp | C07D 273/01 528/393 |
| 2011/0136805 A1 | 6/2011 | Himmelsbach et al. | |
| 2011/0218322 A1 | 9/2011 | Nakamoto et al. | |
| 2013/0310555 A1 | 11/2013 | Chong | |
| 2016/0046762 A1 | 2/2016 | Yoshioka et al. | |

FOREIGN PATENT DOCUMENTS

| | | |
|---|---|---|
| EP | 2896643 A1 | 7/2015 |
| JP | 04-182465 | 6/1992 |
| JP | 3507962 | 11/1994 |
| JP | 08-099979 | 4/1996 |
| JP | 08-134078 | 5/1996 |
| JP | 2690276 B2 | 12/1997 |
| JP | 2777530 B2 | 7/1998 |
| JP | 10-316690 | 12/1998 |
| JP | 11-335267 | 12/1999 |
| JP | 3050228 B2 | 6/2000 |
| JP | 3562000 | 6/2004 |
| JP | 2010-138388 | 6/2010 |
| JP | 4581248 B | 11/2010 |
| JP | 4987719 B2 | 7/2012 |
| JP | 2014-062050 | 4/2014 |
| JP | 2014-156400 | 8/2014 |
| WO | 96/22994 | 8/1996 |
| WO | 96/033162 | 10/1996 |
| WO | 98/043972 | 10/1998 |
| WO | 1999/057174 | 11/1999 |
| WO | 00/02877 | 1/2000 |
| WO | 2004/048316 | 6/2004 |
| WO | 2004/111094 | 12/2004 |
| WO | WO 2006/047419 A2 | 5/2006 |
| WO | WO 2007/127440 A2 | 11/2007 |
| WO | 2008/146172 | 12/2008 |
| WO | 2009/005671 | 1/2009 |
| WO | 2009/021965 | 2/2009 |
| WO | 2011/146336 | 11/2011 |
| WO | 2012/110986 | 8/2012 |
| WO | 2014/157117 | 10/2014 |

OTHER PUBLICATIONS

Corriu, Robert J. P. et al., Silyliron carbonyl complexes in organic synthesis: selective conversion of nitrils into N,N-bis (silyl) enamines, Organometallics, 1985, 4, 623-629.

Iwata, Masaaki et al., Design and synthesis of macromonocyclic polyamines composed of natural methylene arrays, Bulletin of the Chemical Society of Japan, 1989, vol. 62 No. 1, 198-210.

Miki, Yuya et al., Copper-catalyzed electrophili amination of arylsilanes with hydroxylamines, Organic Letters, 2013, vol. 15 No. 1, 172-175.

Snider, Barry B. et al., Synthesis of a bicyclic model for the marine hepatoxin cylindrospermospin, Tetrahedron Letters, 1995, Vo. 36 No. 26, 4587-4590.

Japan Patent Office Action, JP 2016-077377, dated Feb. 8, 2019, 8 pages.

European Patent Office Examination Report, EP 15197846.7, dated May 8, 2018, 6 pages.

Japan Patent Office Action, JP 2015-151011, dated Apr. 24, 2018, 6 pages.

Japan Patent Office Action, JP 2015-151012, dated Apr. 27, 2018, 7 pages.

Extended European Search Report corresponding to European Application No. 18186866.3, dated Aug. 29 2018, 8 pages.

Extended European Search Report corresponding to European Application No. 18165868.9, dated Aug. 24, 2018, 6 pages.

Takasu et al, "Chiral amine-silyl triflate complex mediated asymmetric intramolecuiar Michael-aidol reaction via a novel enanioselective enol silylation process." Chemical Communications (2000) No. 18, pp. 1739-1740.

* cited by examiner

METHOD FOR PRODUCING POLYALKYLENE GLYCOL DERIVATIVE HAVING AMINO GROUP AT END, POLYMERIZATION INITIATOR FOR USE IN THE SAME, AND ALCOHOL COMPOUND AS RAW MATERIAL FOR THE POLYMERIZATION INITIATOR

RELATED APPLICATIONS

This application is a divisional of and claims priority to U.S. patent application Ser. No. 14/959,318, filed Dec. 4, 2015, now allowed, which claims priority from Japanese Patent Application No. 2014-246046, filed Dec. 4, 2014 and Japanese Application No. 2015-151012, filed Jul. 30, 2015, the disclosures of each of which are incorporated by reference herein in their entirety.

FIELD AND BACKGROUND OF THE INVENTION

The present invention relates to a method for producing a polyalkylene glycol derivative having a terminal amino group, a polymerization initiator for use in the same, and an alcohol compound as a raw material of the polymerization initiator.

Recently, in the drug delivery system, a method for encapsulating drugs in a polymer micelle using a block copolymer formed from a hydrophilic segment and a hydrophobic segment has been proposed (refer to, for example, Japanese Patent No. 2690276, Japanese Patent No. 2777530, and Japanese Patent Application Laid-Open No. 11-335267). By using the method, the polymer micelle functions as a carrier for drugs, producing various effects including sustained release of drugs in vivo and concentrated dosage at an affected region.

As the hydrophilic segment, many examples with use of a polyalkylene glycol skeleton are proposed (refer to, for example, Japanese Patent No. 2690276, Japanese Patent No. 2777530, and Japanese Patent Application Laid-Open No. 11-335267). A compound having a polyalkylene glycol skeleton has low toxicity in vivo, and enables excretion by the kidney to be delayed. Consequently, in comparison with a compound having no polyalkylene glycol skeleton, the retention time in blood can be prolonged. As a result, with use of a drug micellized with a polyalkylene glycol derivative, the dosage amount or dosage frequency can be reduced.

Among polyalkylene glycol derivatives, a compound having an amino group at an end can lead to a block copolymer composed of a polyalkylene glycol skeleton and an amino acid skeleton through a ring-opening polymerization reaction with α-amino acid-N-carboxy anhydride. Many examples with use of the produced block copolymer for encapsulating drugs in a polymer micelle are proposed (refer to, for example, Japanese Patent No. 2690276, Japanese Patent No. 2777530, and Japanese Patent Application Laid-Open No. 11-335267).

Synthesis methods of such polyalkylene glycol derivatives having an amino group at an end are also known (refer to, for example, Japanese Patent No. 3050228 and Japanese Patent No. 3562000). In these methods, after polymerization of an alkylene oxide with use of a metal salt of monohydric alcohol as a polymerization initiator, a polymer end is converted to a hydroxyl group, and then to a 2-cyanoethoxy group, finally leading to an amino group-containing substituent group (3-amino-1-propoxy group) through hydrogen reduction of the cyano group.

Other methods for synthesizing a polyalkylene glycol derivative having an amino group include, for example, a method in which ethylene oxide is polymerized with a polymerization initiator the amino group of which is silyl-protected, and then deprotection is performed to lead an amino group (refer to Bioconj. Chem. 1992, 3, 275-276, and Japanese Patent No. 4581248). However, in this method, there is a problem that the end is limited to a 2-amino-1-ethoxy group. Moreover, it is considered that the reactivity is low and the problem is that a long time, as long as 96 hours, are required for increasing the molecular weight up to 6000 (refer to Bioconj. Chem. 1992, 3, 275-276).

SUMMARY OF THE INVENTION

As disclosed in in Japanese Patent No. 3050228, it is difficult to completely dissolve the metal salts of monohydric alcohol used as a polymerization initiator in polymerization solvents (organic solvents such as, for example, tetrahydrofuran (abbreviated as "THF")) in many cases. In these cases, in order to dissolve the metal salts in polymerization solvents, an excess amount of alcohol that is a initiator raw material has to be left during synthesis of the metal salts (for example, in Japanese Patent No. 3050228, 13-mol of methanol to 2 mol of sodium methoxide that is a polymerization initiator). Due to the presence of these alcohols in a reaction system, however, reduction in the polymerization rate is unavoidable. Consequently, crucial reaction conditions such as high temperature and high pressure are required for increasing the polymerization rate. Moreover, when the polymerization initiator does not dissolve in a polymerization solvent, the system does not become uniform, and therefore there is a problem in that the variation of the obtained polyalkylene glycol derivatives becomes broad because polymerization only progresses from the dissolved polymerization initiator.

Monohydric alcohols contain a trace amount of water in many cases. The polymerization of an alkylene oxide with a polymerization initiator prepared in a water-containing state produces a polymer compound having a hydroxyl group at both ends as by-product (hereinafter abbreviated as "diol polymer"). In the case of monohydric alcohols having a boiling point sufficiently higher than that of water, the water content can be reduced by dehydration under reduced pressure. However, since methanol for use in the case in which an end is, for example, a methyl group, has a boiling point lower than that of water, the water content cannot be removed by dehydration under reduced pressure. Therefore, the polymerization of an alkylene oxide with a metal salt prepared by using methanol, unavoidably produces a diol polymer. Since various physical properties of diol polymer such as structure and molecular weight are similar to those of the target substance, separation and purification are extremely difficult. When the subsequent reactions proceed in the presence of diol polymer as an impurity, a polymer including an amino group at both ends is produced unless proper reaction conditions are selected. The direct use of the polymer which includes such an impurity may result in the possibility that an intended performance cannot be achieved in designing a polymer micellizing agent. Therefore, in the polymerization reaction, the water content is required to be reduced to be as low as possible.

In the synthesis methods described in Japanese Patent No. 3050228 and Japanese Patent No. 3562000, a cyano group is converted to an aminomethyl group through hydrogen reduction with a Raney nickel catalyst. In these methods, there is concern over a possibility that trace amounts of metals will be mixed in the final product depending on the use of the polyalkylene glycol derivative in some cases. Furthermore, the reaction is generally considered to require high temperature, there have been problems yet to be solved in that a target product cannot be obtained with a high yield rate because β-elimination of acrylonitrile progresses associated with reaction at a high temperature, and that there is a risk that secondary and tertiary amines are produced due to addition reaction of an amine to an imine that is an intermediate in nitrile reduction and polyacrylonitrile is by-produced.

As a method for synthesizing a polyalkylene glycol derivative having an amino group at an end without using a heavy metal, a method is considered in which an alkylene oxide is polymerized using, as a polymerization initiator, an alkoxide the amino group of which is protected. For example, in the case in which a silyl group is used as a protective group of the amino group, it is extremely difficult to selectively synthesize an alcohol, only the amino group of which is silylated, because the silicon-nitrogen bond is weaker than the silicon-oxygen bond, and therefore, a synthesis example of the alcohol has not yet been reported.

The present invention intends to solve the problems of the conventional technologies, and to provide: a method for producing a narrowly distributed and high-purity polyalkylene glycol derivative having an amino group at an end; and a polymerization initiator for use in the method.

Through intensive research for achieving the objects, the present inventors have found that use of a compound, the amino group of which is protected by a protective group, the compound having a sufficient solubility to polymerization solvents, as a polymerization initiator, makes it possible: to polymerize an alkylene oxide under mild conditions; to suppress production of a diol polymer; further, to remove the diol polymer when produced; besides, to achieve prevention of mixing of heavy metals and prevention of production of by-products; and finally to lead to a high-purity and narrowly distributed polyalkylene glycol derivative having an amino group at an end, and have completed the present invention.

That is to say, the present invention relates to a method for producing a polyalkylene glycol derivative having an amino group at an end with a compound represented by the following general formula (I) as a polymerization initiator, the method including at least a step of reacting the polymerization initiator with an alkylene oxide.

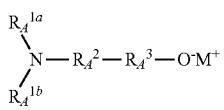

(I)

wherein $R_A^{1a}$ and $R_A^{1b}$ each independently represent a protective group of the amino group, or one of $R_A^{1a}$ and $R_A^{1b}$ represents a hydrogen atom and the other represents a protective group of the amino group, or $R_A^{1a}$ and $R_A^{1b}$ bind to each other to represent a cyclic protective group forming a ring together with a nitrogen atom of the amino group;

$R_A^2$ represents a linear divalent hydrocarbon group having 1 to 6 carbon atoms, or a branched or cyclic divalent hydrocarbon group having 3 to 6 carbon atoms;

$R_A^3$ represents a single bond, or a linear divalent hydrocarbon group having 1 to 20 carbon atoms, or a branched or cyclic divalent hydrocarbon group having 3 to 20 carbon atoms, and the hydrocarbon group may contain a heteroatom;

a total number of carbon atoms of $R_A^2$ and $R_A^3$ is 4 or more, or in a case in which $R_A^3$ contains a heteroatom, a total number of carbon atoms and heteroatoms of $R_A^2$ and $R_A^3$ is 4 or more; and M represents an alkali metal.

According to another embodiment, the present invention relates to a method for producing a polyalkylene glycol derivative having an amino group at an end including the following steps a) to step c):

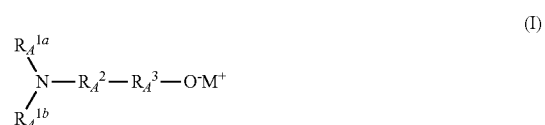

(I)

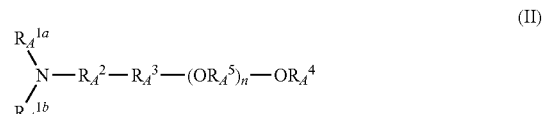

(II)

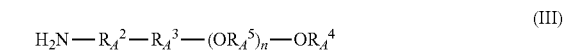

(III)

wherein $R_A^{1a}$ and $R_A^{1b}$ each independently represent a protective group of the amino group, or one of $R_A^{1a}$ and $R_A^{1b}$ represents a hydrogen atom and the other represents a protective group of the amino group, or $R_A^{1a}$ and $R_A^{1b}$ bind to each other to represent a cyclic protective group forming a ring together with a nitrogen atom of the amino group;

$R_A^2$ represents a linear divalent hydrocarbon group having 1 to 6 carbon atoms, or a branched or cyclic divalent hydrocarbon group having 3 to 6 carbon atoms; $R_A^3$ represents a single bond, or a linear divalent hydrocarbon group having 1 to 20 carbon atoms, or a branched or cyclic divalent hydrocarbon group having 3 to 20 carbon atoms, and the hydrocarbon group may contain a heteroatom;

a total number of carbon atoms of $R_A^2$ and $R_A^3$ is 4 or more, or in a case in which $R_A^3$ contains a heteroatom, a total number of carbon atoms and heteroatoms of $R_A^2$ and $R_A^3$ is 4 or more;

$R_A^4$ represents a hydrogen atom, or a linear, branched, or cyclic hydrocarbon group that may be substituted, the hydrocarbon group having 1 to 12 carbon atoms, and the hydrocarbon group may contain a heteroatom;

$R_A^5$ represents an alkylene group having 2 to 8 carbon atoms;

M represents an alkali metal; and n represents an integer of 1 to 450;

Step a)

a step of reacting a polymerization initiator represented by the general formula (I) with an alkylene oxide in a polymerization solvent to obtain a compound represented by the following general formula (I-1):

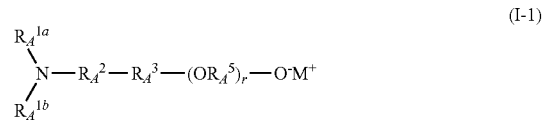

(I-1)

wherein $R_A^{1a}$, $R_A^{1b}$, $R_A^2$, $R_A^3$ and $R_A^5$ are the same as defined in the general formulas (II) and (III) as above;

M represents an alkali metal and is the same as M in the general formula (I) as above; and r represents an integer of 1 to 445;

Step b)

a step of reacting the compound represented by the general formula (I-1) with a compound represented by the following general formula (I-2) to obtain a compound represented by the general formula (II):

$$R_A^4OR_A^5)_kL \qquad (1\text{-}2)$$

wherein $R_A^4$ and $R_A^5$ are the same as defined in the general formulas (II) and (III);

k represents an integer of 0 to 5; and

L represents a leaving group; and

Step c)

a step of deprotecting the compound represented by the general formula (II) to obtain a compound represented by the general formula (III).

According to yet another embodiment, the present invention relates to a protected amino group-containing alcohol compound represented by the following general formula (i):

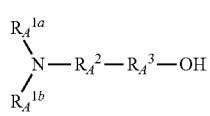

(i)

wherein $R_A^{1a}$ and $R_A^{1b}$ each independently represent a protective group of the amino group, or one of $R_A^{1a}$ and $R_A^{1b}$ represents a hydrogen atom and the other represents a protective group of the amino group, or $R_A^{1a}$ and $R_A^{1b}$ bind to each other to represent a cyclic protective group forming a ring together with a nitrogen atom of the amino group;

$R_A^2$ represents a linear divalent hydrocarbon group having 1 to 6 carbon atoms, or a branched or cyclic divalent hydrocarbon group having 3 to 6 carbon atoms;

$R_A^3$ represents a single bond, or a linear divalent hydrocarbon group having 1 to 20 carbon atoms, or a branched or cyclic divalent hydrocarbon group having 3 to 20 carbon atoms, and the hydrocarbon group may contain a heteroatom; and total number of carbon atoms of $R_A^2$ and $R_A^3$ is 4 or more, or in a case in which $R_A^3$ contains a heteroatom, a total number of carbon atoms and heteroatoms of $R_A^2$ and $R_A^3$ is 4 or more.

According to still yet another embodiment, the present invention relates to a metal salt of a protected amino group-containing alcohol compound, the metal salt represented by the following general formula (I):

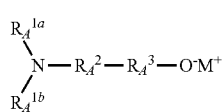

(I)

wherein $R_A^{1a}$ and $R_A^{1b}$ each independently represent a protective group of the amino group, or one of $R_A^{1a}$ and $R_A^{1b}$ represents a hydrogen atom and the other represents a protective group of the amino group, or $R_A^{1a}$ and $R_A^{1b}$ bind to each other to represent a cyclic protective group forming a ring together with a nitrogen atom of the amino group;

$R_A^2$ represents a linear divalent hydrocarbon group having 1 to 6 carbon atoms, or a branched or cyclic divalent hydrocarbon group having 3 to 6 carbon atoms;

$R_A^3$ represents a single bond, or a linear divalent hydrocarbon group having 1 to 20 carbon atoms, or a branched or cyclic divalent hydrocarbon group having 3 to 20 carbon atoms, and the hydrocarbon group may contain a heteroatom;

a total number of carbon atoms of $R_A^2$ and $R_A^3$ is 4 or more, or in a case in which $R_A^3$ contains a heteroatom, a total number of carbon atoms and heteroatoms of $R_A^2$ and $R_A^3$ is 4 or more; and M represents an alkali metal.

By using the method for producing a polyalkylene glycol derivative having an amino group at an end according to the present invention, polymerization performed substantially in the absence of an alcohol, that is a polymerization initiator raw material and that is a cause of reduction in polymerization rate, becomes possible. The polymerization of an alkylene oxide can be performed under milder conditions than conventional conditions. Furthermore, production of impurities such as a diol polymer attributable to a trace amount of water is suppressed. Even if water is mixed, and resulting in production of polymer impurities, the polymer impurities can be removed by separation and purification, making it possible to produce a high-purity and narrowly distributed polyalkylene glycol derivative. Moreover, in the case in which the method also includes a purification step, since freeze drying is not needed during the purification and extraction of the polyalkylene glycol derivative, the method is further advantageous in that the polyalkylene glycol derivative can be produced on an industrial scale and simplification of facilities and processes can be realized. Furthermore, by using the polymerization initiator in which the amino group is protected, the reduction method using a heavy metal does not have to be used to prevent for by-products being mixed, and therefore, it becomes possible to reduce a risk of mixing heavy metal impurities and by-products that should be avoided in medical supplies. Furthermore, since the polymerization initiator uniformly dissolves in the system, the polyalkylene glycol derivative produced by the production method according to the present invention is narrowly distributed, capable of being extremely advantageously used in leading to a block copolymer formed from a hydrophilic segment and a hydrophobic segment, for use in the field of drug delivery systems. Furthermore, the alcohol compound the amino group of which is protected and the alkali metal salt thereof according to the present invention may be used as a more useful polymerization initiator and a precursor thereof in place of conventional polymerization initiators and precursors thereof in the method for producing a polyalkylene glycol derivative, and therefore are extremely useful.

DETAILED DESCRIPTION OF PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

The present invention is a method for producing a polyalkylene glycol derivative having an amino group at an end, using a compound represented by the following general formula (I) as a polymerization initiator, the method including at least a step of reacting the polymerization initiator with an alkylene oxide. The present invention, according to an embodiment, sequentially performs the following steps a) to c) (hereinafter, this embodiment is sometimes referred to as "Embodiment 1"):

Step a)
a step of reacting a polymerization initiator represented by the general formula (I) with an alkylene oxide in a polymerization solvent to obtain a compound represented by the following general formula (I-1);

Step b)
a step of reacting the compound represented by the general formula (I-1) with a compound represented by the following general formula (I-2) to obtain a compound represented by the following general formula (II); and Step c)
a step of deprotecting the compound represented by the general formula (II) to obtain a compound represented by the general formula (III).

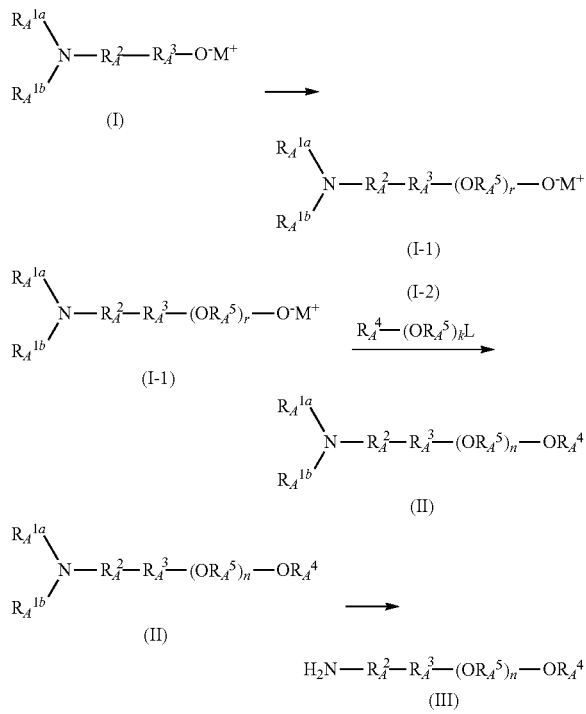

In the general formulas (I), (I-1), and (II), $R_A^{1a}$ and $R_A^{1b}$ each independently represent a protective group of the amino group, or one of $R_A^{1a}$ and $R_A^{1b}$ represents a hydrogen atom and the other represents a protective group of the amino group, or $R_A^{1a}$ and $R_A^{1b}$ bind to each other to represent a cyclic protective group forming a ring together with a nitrogen atom of the amino group. The protective group is preferably a protective group that is deprotectable without using a heavy metal catalyst. The kinds of protective groups represented by $R_A^{1a}$ and/or $R_A^{1b}$ may be exemplified by classifying the protective groups into the following (P-1) to (P-4), although this is not limited thereto.

(P-1) Protective group of a structure represented by $Si(R^1)_3$ (trialkylsilyl group)

In the case in which $R_A^{1a}$ and $R_A^{1b}$ in the general formulas (I), (I-1), and (II) each independently represent a protective group of the amino group, and in the case in which one of $R_A^{1a}$ and $R_A^{1b}$ represents a hydrogen atom and the other represents a protective group of the amino group, $R_A^{1a}$ and/or $R_A^{1b}$ may be a protective group of a structure represented by $Si(R^1)_3$ (trialkylsilyl group).

In the structure represented by $Si(R^1)_3$, $R^1$ each independently represent a linear monovalent hydrocarbon group having 1 to 6 carbon atoms, or a branched or cyclic monovalent hydrocarbon group having 3 to 6 carbon atoms, or $R^1$ may bind to each other to form a 3 to 6 membered ring together with a silicon atom having bonds with $R^1$. Examples of $R^1$ include a methyl group, an ethyl group, an n-propyl group, an isopropyl group, an n-butyl group, an isobutyl group, a tert-butyl group, an n-pentyl group, an n-hexyl group, a cyclopropyl group, a cyclobutyl group, a cyclopentyl group, and a cyclohexyl group. Moreover, in the case in which $R^1$ bind to each other to form a ring together with a silicon atom, examples of $R^1$ include a group obtained by eliminating one hydrogen atom from the above-listed groups.

Preferred specific examples of the protective group having a structure represented by $Si(R^1)_3$ include a trimethylsilyl group, a triethylsilyl group, and a tert-butyldimethylsilyl group, although this is not limited thereto.

(P-2) Protective Group of a Structure Represented by $R_A^6 OCO$

In the case in which $R_A^{1a}$ and $R_A^{1b}$ in the general formulas (I), (I-1), and (II) each independently represent a protective group of the amino group, and in the case in which one of $R_A^{1a}$ and $R_A^{1b}$ represents a hydrogen atom and the other represents a protective group of the amino group, $R_A^{1a}$ and/or $R_A^{1b}$ may be a protective group of a structure represented by $R_A^6 OCO$.

In the structure represented by $R_A^6 OCO$, $R_A^6$ represents a residue of a monovalent hydrocarbon having 1 to 20 carbon atoms, and the residue may contain a halogen atom, an oxygen atom, a nitrogen atom, a sulfur atom, a silicon atom, a phosphorus atom, or a boron atom.

As the protective group represented by the structure of $R_A^6 OCO$, a methyloxycarbonyl group, an ethyloxycarbonyl group, an isobutyloxycarbonyl group, a tert-butyloxycarbonyl group, a tert-amyloxycarbonyl group, a 2,2,2-trichloroethyloxycarbonyl group, a 2-trimethylsilylethyloxycarboyl group, a phenylethyloxycarbonyl group, a 1-(1-adamantyl)-1-methylethyloxycarbonyl group, a 1,1-dimethyl-2-haloethyloxycarbonyl group, a 1,1-dimethyl-2,2-dibromoethyloxycarbonyl group, a 1,1-dimethyl-2,2,2-trichloroethyloxycarbonyl group, a 1-methyl-1-(4-biphenyl) ethyloxycarbonyl group, a 1-(3,5-di-t-butylphenyl)-1-methylethyloxycarbonyl group, a 2-(2'-pyridyl) ethyloxycarbonyl group, a 2-(4'-pyridyl)ethyloxycarbonyl group, a 2-(N,N-dicyclohexylcarboxyamide)ethyloxycarbonyl group, a 1-adatnantyloxycarbonyl group, a vinyloxycarbonyl group, an allyloxycarbonyl group, a 1-isopropylallyloxycarbonyl group, a cinnamyloxycarbonyl group, a 4-nitrocinnamyloxycarbonyl group, a 8-quinolyloxycarbonyl group, a N-hydroxypiperidinyloxycarbonyl group, an alkyldithiocarbonyl group, a benzyloxycarbonyl group, a p-methoxybenzyloxycarbonyl group, a p-nitrobenzyloxycarbonyl group, a p-bromobenzyloxycarbonyl group, a p-chlorobenzyloxycarbonyl group, a 2,4-dichlorobenzyloxycarbonyl group, a 4-methylsulfinylbezyloxycarbonyl group, a 9-anthrylmethyloxycarbonyl group, a diphenylmethyloxycarbonyl group, a 9-fluorenylmethyloxycarbonyl group, a 9-(2,7-dibromo)fluorenylmethyloxycarbonyl group, a 2,7-di-t-butyl-[9-(10,10-dioxo-thioxanthenyl)]methyloxycarbonyl group, a 4-methoxyphenacyloxycarbonyl group, a 2-methylthioethyloxycarbonyl group, a 2-methylsulfonylethyloxycarbonyl group, a 2-(p-toluenesulfonyl)ethyloxycarbonyl group, a [2-(1,3-dithianyl)]methyloxycarbonyl group, a 4-methylthiophenyloxycarbonyl group, a 2,4-dimethylthiophenyloxycarbonyl group, a 2-phosphonioethyloxycarbonyl group, a 2-triphenylphosphonioisopropyloxycarbonyl group, a 1,1-dimethyl-2-cyanoethyloxycarbonyl group, an m-chloro-p-acyloxybenzyloxycarbonyl group, a p-(dihydroxyboryl)benzyloxycarbonyl group, a 5-benzoisooxazolylmethyloxycarbonyl group, a 2-(trifluoromethyl)-6-chromonylmethyloxycarbonyl group, a phenyloxycarbonyl group, an m-nitrophenyloxycarbonyl group, a 3,5-dimethoxybenzyloxycarbonyl group, an o-nitrobenzyloxycarbonyl group, a 3,4-dimethoxy-6-nitrobenzyloxycarbonyl group, and a phenyl(o-nitrophenyl)methyloxycarbonyl group are included. Among them, the tert-butyloxycarbonyl group, the 2,2,2-trichloroethyloxycarbonyl group, the allyloxycarbonyl group, the benzyloxycarbonyl group, and the 9-flurorenylmethyloxycarbonyl group are preferred.

(P-3) Cyclic Protective Group

In the case in which $R_A^{1a}$ and $R_A^{1b}$ bind to each other to represent a cyclic protective group forming a ring together with a nitrogen atom of the amino group, as the cyclic protective group, an N-phthaloyl group, an N-tetrachlorophthaloyl group, an N-4-nitrophthaloyl group, an N-dithiasucciloyl group, an N-2,3-diphenylmaleoyl group, an N-2,5-dimethylpyrrolyl group, an N-2,5-bis(triisopropylsiloxy)pyrrolyl group, an N-1,1,3,3-tetramethyl-1,3-disilaisoindolyl group, a 3,5-dinitro-4-pyridonyl group, a 1,3,5-dioxazinyl group, and a 2,2,5,5-tetramethyl-2,5-disila-1-azacyclopentane are included, although this is not limited thereto. Among them, the N-phthaloyl group is preferred.

(P-4) Other Protective Groups

In the case in which $R_A^{1a}$ and/or $R_A^{1b}$ represent a protective group other than (P-1) to (P-3), as the protective group, a benzyl group, a p-methoxybenzyl group, a p-toluenesulfonyl group, a 2-nitrobenzenesulfonyl group, a (2-trimethylsilyl)ethanesulfonyl group, an allyl group, a pivaloyl group, a methoxymethyl group, a di(4-methoxyphenyl)methyl group, a 5-dibenzosuberyl group, a trinylmethyl group, a (4-methoxyphenyl)diphenylmethyl group, a 9-phenylfluorenyl group, a [2-(trimethylsilyl)ethoxy]methyl group, and an N-3-acetoxypropyl group are included, although this is not limited to the protective groups. Preferably, a protective group that is deprotectable without using a heavy metal catalyst may appropriately be selected for use. Among others, the benzyl group, the p-toluenesulfonyl group, the 2-nitrobenzenesulfonyl group, and the allyl group are preferable.

In the general formulas (I), (I-1), (II), and (III), $R_A^2$ represents a linear divalent hydrocarbon group having 1 to 6 carbon atoms, or a branched or cyclic divalent hydrocarbon group having 3 to 6 carbon atoms. Specific examples of $R_A^2$ include a group obtained by eliminating one hydrogen atom from each of a methyl group, an ethyl group, an n-propyl group, an isopropyl group, an n-butyl group, an isobutyl group, a tert-butyl group, an n-pentyl group, an n-hexyl group, a cyclopropyl group, a cyclobutyl group, a cyclopentyl group, and a cyclohexyl group.

In the general formulas (I), (I-1), (II), and (III), $R_A^3$ represents a single bond, or a linear divalent hydrocarbon group having 1 to 20 carbon atoms, or a branched or cyclic divalent hydrocarbon group having 3 to 20 carbon atoms, and the hydrocarbon group may contain a heteroatom such as a nitrogen atom, an oxygen atom, and a sulfur atom. Specific examples of $R_A^3$ include a group obtained by eliminating one hydrogen atom from each of a methyl group, an ethyl group, an n-propyl group, an isopropyl group, an n-butyl group, an isobutyl group, a tert-butyl group, a pentyl group, a cyclopentyl group, a hexyl group, a cyclohexyl group, an octyl group, a decyl group, a dodecyl group, a phenyl group, an o-tolyl group, an m-tolyl group, ap-tolyl group, a 2,3-xylyl group, a 2,4-xylyl group, a 2,5-xylyl group, a 2,6-xylyl group, a 3,4-xylyl group, a 3,5-xylyl group, a mesityl group. Some of the carbon atoms in these hydrocarbon groups may be substituted by a heteroatom such as a nitrogen atom, an oxygen atom, and a sulfur atom (however, excluding: a bonding site with the oxygen atom that constitutes $O^-M^+$ in the general formula (I); and bonding site with the oxygen atom that constitutes $(OR_A^5)$ in the general formulas (I-1), (II), and (III)). Among others, $R_A^3$ is preferably a structure represented by the following general formula (VII). The reason is because the compatibility between the polymerization initiator represented by the general formula (I) and polymerization solvents can be improved.

$$—(OR_A^5)_p^- \qquad (VII)$$

In the general formula (VII), $R_A^5$ is the same as $R_A^5$ in the general formulas (I-1), (I-2), (II), and (III), the specific examples thereof are as will be described later. p represents an integer of 1 to 10, preferably an integer of 1 to 5, more preferably an integer of 1 to 2 in the viewpoint of purifying the alcohol compound to be a raw material of a polymerization initiator by distillation.

The total number of carbon atoms of $R_A^2$ and carbon atoms of $R_A^3$ is 4 or more. In the case in which part of the carbon atoms in $R_A^3$ is substituted by a heteroatom, the total number of carbon atoms in which the number of heteroatoms is included as the number of carbon atoms may be 4 or more. The total number of carbon atoms of $R_A^2$ and $R_A^3$ is preferably 4 to 15, more preferably 4 to 9. In the polymerization initiator represented by the general formula (I), the length of a chain consisting of $R_A^2$ and $R_A^3$ and connecting the nitrogen atom at one end and the oxygen atom-(oxygen atom that constitutes $O^-M^+$) at the other end is made long, as long as 4 or more, so that the solubility to polymerization solvents is improved and, in a substrate having a possibility that a protective group on nitrogen is rearranged on oxygen in the compound represented by the general formula (I), the rearrangement can be prevented.

In the general formulas (I-2), (II), and (III), $R_A^4$ represents a hydrogen atom, or a linear, branched, or cyclic hydrocarbon group that may be substituted, the hydrocarbon group having 1 to 12 carbon atoms, and the hydrocarbon group may contain a heteroatom. Specific examples of $R_A^4$ include a methyl group, an ethyl group, an n-propyl group, an isopropyl group, an n-butyl group, an isobutyl group, a tert-butyl group, a pentyl group, a cyclopentyl group, a hexyl group, a cyclohexyl group, an octyl group, a decyl group, a dodecyl group, a phenyl group, an o-tolyl group, an m-tolyl group, ap-tolyl group, a 2,3-xylyl group, a 2,4-xylyl group, a 2,5-xylyl group, a 2,6-xylyl group, a 3,4-xylyl group, a 3,5-xylyl group, a mesityl group, a vinyl group, and an allyl group. In the case in which $R_A^4$ has a substituent, examples of the substituent include an acetalized formyl group, a cyano group, a formyl group, a carboxyl group, an amino group, an alkoxycarbonyl group having 1 to 6 carbon atoms, an acylamide group having 2 to 7 carbon atoms, tri(same or different alkyl having 1 to 6 carbon atoms)siloxy group, a siloxy group, a silylamino group, a maleimide group, a thiol group, a hydroxide group, a methacryloyloxy group, an acryloyloxy group, an active ester group, and an azi group. Specific examples of $R_A^4$ having a substituent include substituents represented by the following structures, although this is not limited thereto. In addition, the following formulas each represent an end portion of $R_A^4$ of a substituted structure, and the dotted lines in the formulas show that a hydrocarbon portion of $R_A^4$ can have variations as exemplified above. The number of substituents is preferably 1 to 3, although this is not particularly limited thereto. Such substituents may further be protected by a freely selected appropriate protective group.

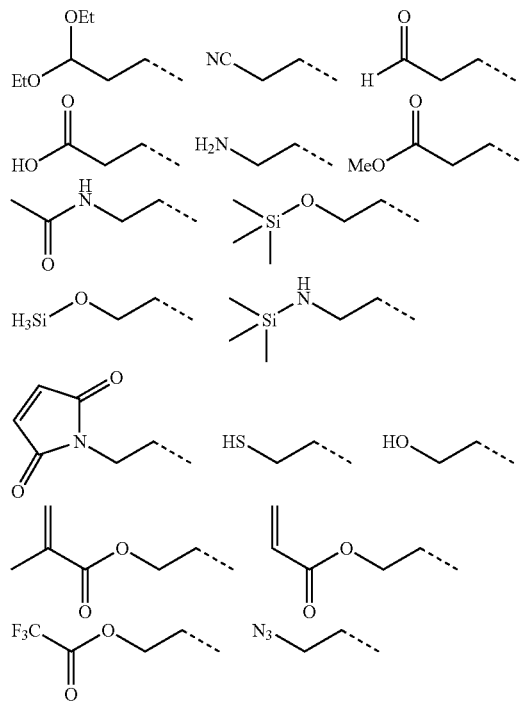

In the general formulas (I-1), (I-2), (II), and (III), $R_A^5$ represents an alkylene group having 2 to 8 carbon atoms. Among others, alkylene groups having 2 to 3 carbon atoms are preferred. That is to say, $R_A^5$ is preferably an ethylene group or a propylene group. The $(OR_A^5)$ unit in the general formulas (I-1), (I-2), (II), and (III) may be constituted from a single kind of oxyalkylene group, for example, from only an oxyethylene or oxypropylene group, or two or more kinds of oxyalkylene groups may be mixed together. In the case in which two or more kinds of oxyalkylene groups are mixed together, $(OR_A^5)$ may be constituted from two or more kinds of different oxyalkylene groups by random polymerization or block polymerization.

In the general formulas (I) and (I-1), M represents an alkali metal. Specific examples of M include lithium, sodium, potassium, cesium, sodium-potassium alloy.

In the general formula (I-1), r represents an integer of, for example, 1 to 445, preferably an integer of 10 to 395, more preferably an integer of 20 to 345.

In the general formula (I-2), k represents an integer of, for example, 0 to 5. The compound represented by the general formula (I-2) where k=0 has a low boiling point and is difficult to handle, or has a high toxicity in some cases, and therefore k is preferably an integer of 1 to 5, more preferably an integer of 1 to 3.

In the general formula (I-2), L represents a leaving group. Specific examples of L include Cl, Br, I, trifluoromethanesulfonate (hereinafter, written as "TfO"), p-toluenesulfonate (hereinafter, written as "TsO"), and methanesulfonate (hereinafter, written as "MsO"), although this is not limited thereto.

In the general formulas (II) and (III), n represents an integer of 1 to 450, preferably an integer of 10 to 400, more preferably an integer of 20 to 350. Moreover, n is also represented by the sum of r and k.

In selecting each of the compounds for use in each step in the production method of the present embodiment 1 and represented by the general formulas (I), (I-1), (I-2), and (II), desired $R_A^{1a}$, $R_A^{1b}$, $R_A^2$, $R_A^3$, $R_A^4$, $R_A^5$, M, r, k, L, and n in the general formulas (I), (I-1), (I-2), and (II) may be selected so that the compounds represented by the general formulas (III) as the desired final products may be obtained.

Moreover, the present embodiment 1 may include, as an optional step prior to the steps a) to c), a pre-step for synthesizing the compound represented by the general formula (I) used as a polymerization initiator. The pre-step includes: a step (pre-step 1) of synthesizing a compound represented by the following general formula (i) used as a precursor of the polymerization initiator and; and a step (pre-step 2) of synthesizing, using the compound represented by the general formula (i), the compound represented by the general formula (I) used as a polymerization initiator. The present embodiment includes: an aspect in which the pre-step 2 is performed subsequently to the pre-step 1; and an aspect in which only the pre-step 2 is performed not through the pre-step 1. A scheme of the pre-step 2 is shown as follows.

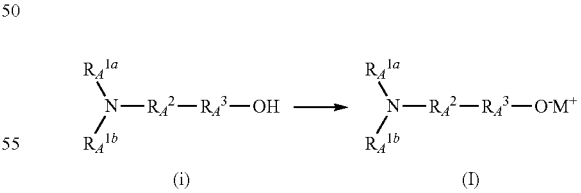

(In the general formula (i), $R_A^{1a}$, $R_A^{1b}$, $R_A^2$, $R_A^3$, and M are the same as defined in the general formula (I))

Moreover, the present embodiment 1 may include, as an optional step after the steps a) to c), a post-treatment step of purifying the compound represented by the general formula (III) obtained in the step c).

The preferred embodiments will be described below in the order of the pre-steps 1 to 2, the steps a) to c), and the post-treatment step along time series.

[Pre-Step 1]

The pre-step 1 is a step of synthesizing the alcohol compound represented by the general formula (i) used as a precursor of the polymerization initiator, and the production may be performed by the following step (i-1), although this is not limited thereto.

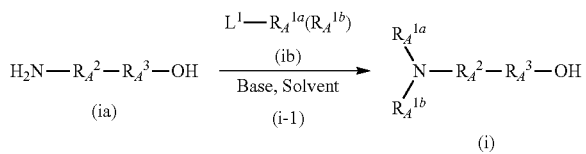

(In the general formulas (ia) and (ib), $R_A^{1a}$, $R_A^{1b}$, $R_A^2$, and $R_A^3$ are the same as defined in the general formula (i), namely are the same as defined in the general formula (I), and $L^1$ represents a leaving group)

Specific examples of $L^1$ as the leaving group in the general formulas (ia) and (ib) include Cl, Br, I, TfO, TsO, and MsO, although this is not limited thereto.

In synthesizing the compound represented by the general formula (i) by performing the step (i-1), for example, reaction may be performed by adding a basic compound to the compound represented by the general formula (ia) without a solvent, and subsequently dripping the compound represented by the general formula (ib) to mix, or, reaction may be performed by dissolving the compound represented by the general formula (ia) in a proper solvent, then adding a basic compound, and then dripping the compound represented by the general formula (ib) to mix. The amount of the compound represented by the general formula (ib) used is, for example, 1 to 5 times, preferably 1.5 to 3 times the number of moles of the compound represented by the general formula (ia), and, in the viewpoint of reacting a protective group selectively with only an amino group, 1.5 to 2 times are more preferred.

In the case in which a solvent is used in the step (i-1), and specific examples of the solvent include ethers such as THF and 1,4-dioxane, aromatic hydrocarbons such as benzene, toluene, and xylene, halogens such as methylene chloride, and N,N-dimethylformamide, N-methyl-2-pyrrolidone, acetonitrile, and acetone, although this is not limited thereto. The amount of the solvent used is, for example, 1 to 20 times, preferably 2 to 10 times, more preferably 2 to 5 times the mass of the compound represented by the general formula (ia), although this is not particularly limited thereto.

Specific examples of the basic compound for use in the step (i-1) include hydroxides such as sodium hydroxide, potassium hydroxide, and tetramethylammonium hydroxide, carbonates such as sodium carbonate, potassium carbonate, and cesium carbonate, metal alkoxides such as sodium methoxide, sodium ethoxide, and potassium t-butoxide, metal hydrides such as sodium hydride and potassium hydride, and primary, secondary, and tertiary aliphatic amines, conjugated amines, aromatic amines, heterocyclic amines, and ammonia water, although this is not limited thereto. The amount of the basic compound used is, for example, 1 to 5 times, preferably 1.5 to 3 times, more preferably 1.5 to 2 times the mass of the compound represented by the general formula (ia).

The reaction temperature in the step (i-1) may be within a range from the melting point to the boiling point of the solvent used, and is, for example, −60° C. to 150° C., preferably 0° C. to 80° C. The completion of the reaction in the step (i-1) can be assumed when the compound represented by the general formula (ia) analyzed by gas chromatography disappears, or when the compound represented by the general formula (i) is obtained as a main product.

In the case in which $R_A^{1a}$ and $R_A^{1b}$ are intended to be different protective groups, or in the case in which there is a risk that a protective group protects not only an amino group but also a hydroxy group because of a high steric hindrance of the protective group, synthesis may be performed by protecting an amino group by a first protective group in the first place, then protecting a hydroxy group by another deprotectable protective group, subsequently protecting the amino group further by a second protective group, and finally deprotecting the hydroxy group. It can happen that a protective group may protect a hydroxy group, or only one protective group is introduced in an amino group because selectivity of the amino group against a hydroxy group is not obtained depending on the reaction condition, however, in that case, the compound represented by the general formula (i) and the other by-products can be separated by precision distillation. The compound represented by the general formula (i) is preferably purified by distillation to remove water, even in the case in which the by-product is not produced. In that case, the water content ratio of the compound represented by the general formula (i) is, for example, 50 ppm or less, preferably 10 ppm or less, more preferably 5 ppm or less.

In the case in which $R_A^3$ in the compound represented by the general formula (i) contains a heteroatom, examples of the other methods for producing the compound represented by the general formula (i) include such, methods as (i-2) to (i-3) using a compound represented by the general formula (if) having a hydrogen atom next to the heteroatom, although this is not limited thereto.

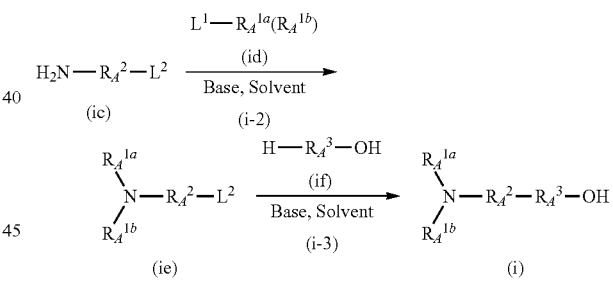

(In the general formulas (ic), (id), (ie), and (if), $R_A^{1a}$, $R_A^{1b}$, $R_A^2$, $R_A^3$, and $L^1$ are the same as defined in the general formulas (ia) and (ib), and $L^2$ represents a leaving group)

Specific examples of $L^2$ as the leaving group in the general formulas (ic) and (ie) include Cl, Br, I, TfO, TsO, and MsO, although this is not limited thereto.

In performing the step (i-2), for example, reaction may be performed by adding a basic compound to the compound represented by the general formula (ic) without a solvent, and subsequently dripping the compound represented by the general formula (id) to mix, or, reaction may be performed by dissolving the compound represented by the general formula (ic) in a proper solvent, then adding a basic compound, and then dripping the compound represented by the general formula (id) to mix. The amount of the compound represented by the general formula (id) used is, for example, 2 to 10 times, preferably 2 to 5 times, more preferably 2 to 3 times the number of moles of the compound represented by the general formula (ic).

In the case in which a solvent is used in the step (i-2), specific examples of the solvent are the same as the specific examples of the solvent described in the step (i-1). The amount of the solvent used is, for example, 1 to 20 times, preferably 2 to 10 times, more preferably 2 to 5 times the mass of the compound represented by the general formula (ic), although this is not particularly limited thereto.

Specific examples of the basic compound for use in the step (i-2) are the same as the specific examples of the basic compound described in the step (i-1). The amount of the basic compound used is, for example, 2 to 10 times, preferably 2 to 5 times, more preferably 2 to 3 times the number of moles of the compound represented by the general formula (ic).

The reaction temperature in the step (i-2) may be within a range from the melting point to the boiling point of the solvent used, and is, for example, −60° C. to 150° C., preferably 0° C. to 80° C. The completion of the reaction in the step (i-2) can be assumed when the compound represented by the general formula (ic) analyzed by gas chromatography disappears, or when the compound represented by the general formula (ie) is obtained as a main product.

In synthesizing the compound represented by the general formula (i) by subsequently performing the step (i-3), the compound represented by the general formula (if) and a basic compound may be directly added to the reaction liquid after completion of the step (i-2), or, the compound represented by the general formula (ie) may be dripped into a mixed solution of the compound represented by the general formula (if), the basic compound, and the solvent, after the compound represented by the general formula (ie) is once purified and extracted. Moreover, the step (i-3) may be performed without a solvent. The amount of the compound represented by the general formula (if) used is 1 to 30 times, preferably 2 to 20 times, more preferably 5 to 10 times the number of moles of the compound represented by the general formula (ie). For example, in the case in which $R_A^3$ is a compound represented by the general formula (VII), the compound represented by the general formula (if) is a diol, and use of the compound represented by the general formula (if) in an excessive amount relative to the number of moles of the compound represented by the general formula (ie) makes it possible to react a hydroxy group at one end of the compound represented by the general formula (if).

In the case in which a solvent is used in the step (i-3), and specific examples of the solvent are the same as the specific examples of the solvent described in the step (i-1). The amount of the solvent is, for example, 1 to 20 times, preferably 2 to 10 times, more preferably 2 to 5 times the mass of the compound represented by the general formula (ie), although this is not particularly limited thereto. Specific examples of the basic compound for use in the step (i-3) are the same as the specific examples of the basic compound described in the step (i-1). The amount of the basic compound used is, for example, 1 to 2 times, preferably 1 to 1.5 times, more preferably 1 to 1.2 times the number of moles of the compound represented by the general formula (ie).

The reaction temperature in the step (i-3) may be within a range from the melting point to the boiling point of the solvent, and is, for example, −60° C. to 150° C., preferably 0° C. to 80° C. The completion of the reaction in the step (i-3) can be assumed when the compound represented by the general formula (ie) analyzed by gas chromatography disappears. Both the heteroatom on $R_A^3$ and the hydroxy group at an end react with the compound represented by the general formula (ie) to produce a by-product in some cases depending on the reaction condition; however, in that case, the compound represented by the general formula (i) and by-product can be separated by precision distillation. The compound represented by the general formula (i) is preferably purified by distillation to remove water, even in the case in which the by-product is not produced. In that case, the water content ratio of the compound represented by the general formula (i) is, for example, 50 ppm or less, preferably 10 ppm or less, more preferably 5 ppm or less.

[Pre-Step 2]

The pre-step 2 is a step of reacting the compound represented by the general formula (i) with an alkali metal or an alkali metal compound to obtain the compound represented by the general formula (I).

In the [Pre-Step 2], the alkali metal or the alkali metal compound to be reacted with the compound represented by the general formula (i) may be a substance selected from the group consisting of alkali metals represented by M, hydrides of alkali metals represented by $M^+H^-$, organic alkali metals represented by $R_X^-M^+$ or $[R_Y]^-$ ($R_X$ represents an alkyl group that may have a substituent, the alkyl group having 1 or 20 carbon atoms, preferably represents an alkyl group having 1 to 20 carbon atoms, or an arylalkyl group having 7 to 20 carbon atoms, and Ry represents an aromatic compound that may have a substituent), and alkali metal salts of monohydric alcohols represented by $R_Z O^- M^+$ ($R_Z$ represents an alkyl group having 1 to 6 carbon atoms).

Specific examples of M as the alkali metal include lithium, sodium, potassium, cesium, and sodium-potassium alloy. Specific examples of $M^+H^-$ include sodium hydride, and potassium hydride. Specific examples of $R_X^-M^+$ include ethyllithium, ethylsodium, n-butyllithium, sec-butyllithium, tert-butyllithium, 1,1-diphenylhexyllithium, 1,1-diphenyl-3-methylpentyllithium, 1,1-diphenylmethylpotassium, cumylsodium, cumylpotassium, and cumylcesium. Specific examples of $[R_Y]^-M^+$ include lithium naphthalenide, sodium naphthalenide, potassium naphthalenide, anthracenelithium, anthracenesodium, anthracenepotassium, biphenylsodium, sodium 2-phenylnaphthalenide, phenanthrenesodium, sodium acenaphthylenide, sodium benzophenone ketyl, sodium 1-methylnaphthalenide, potassium 1-methylnaphthalenide, sodium 1-methoxynaphthalenide, potassium 1-methoxynaphthalenide, and these compounds may be used alone or in combination of two or more. Specific examples of $R_Z$ in $R_Z O^- M^+$ include a methyl group, an ethyl group, an n-propyl group, an isopropyl group, an n-butyl group, a sec-butyl group, a tert-butyl group, an n-pentyl group, an isopentyl group, and an n-hexyl group, although this is not limited thereto. Among others, as alkali metal or the alkali metal compound, sodium, potassium, sodium hydride, and potassium hydride are preferred in the view point that side reaction is suppressed, and moreover, sodium naphthalenide, potassium naphthalenide, anthracenesodium, anthracenepotassium, sodium methoxide, potassium methoxide, sodium ethoxide, and potassium ethoxide are preferred in the viewpoint of high reactivity.

The amount of the alkali metal or the alkali metal compound used in the reaction in the pre-step 2 is 0.5 to 3.0 equivalents, preferably 0.8 to 2.0 equivalents, more preferably 0.9 to 1.0 equivalents, relative to the number of moles of the compound represented by the general formula (i). Particularly in the case in which the alkali metal compound that can also function as a polymerization initiator is used in the step a), it is necessary to suppress the amount of the alkali metal compound used to 1.0 equivalent or less. For example, in the case in which potassium methoxide is used, it is necessary to distill away methanol produced in the pre-step 2 under reduced pressure after synthesis of the polymerization initiator so that potassium methoxide may not function as a polymerization initiator in the step a).

In synthesizing the compound represented by the general formula (I) in the pre-step 2, for example, the alkali metal or the alkali metal compound may be directly added after the compound represented by the general formula (i) distilled and purified in the pre-step 1 is dissolved in a proper solvent, or, the compound represented by the general formula (i) may be added to a solution obtained by dissolving the alkali metal or the alkali metal compound in a proper solvent. Specific examples of the solvent used in the pre-step 2 include ethers such as THF and 1,4-dioxane, and aromatic hydrocarbons such as benzene, toluene, and xylene, although this is not limited thereto. In the case in which the solvent is used, a solvent distilled with a dehydrating agent such as metal sodium is preferably used. The water content ratio of the solvent is, for example, 50 ppm or less, preferably 10 ppm or less, more preferably 5 ppm or less. The amount of the solvent used is, for example, 1 to 50 times, preferably 2 to 10 times, more preferably 2 to 5 times the mass of the compound represented by the general formula (i), although this is not particularly limited thereto. Moreover, the reaction in the pre-step 2 is performed at a temperature of −78 to 100° C., preferably at a temperature of 0° C. to the reflux temperature of the solvent for use (for example, 0° C. to 66° C. as a reflux temperature of THF), and the reaction system may be cooled or heated as needed.

Among others, as the solvent for use in the [Pre-Step 2], the same solvent as will be used as the polymerization solvent in the subsequent [Step a] as will be described later is preferably used. The reason is because whether the polymerization initiator synthesized in the [Pre-Step 2] dissolves or not in the polymerization solvent for use in the [Step a] can be confirmed in advance during the synthesis of the polymerization initiator in the [Pre-Step 2]. Specifically, the solubility of the polymerization initiator in the polymerization solvent can be confirmed in a manner as described below in the case in which, for example, THF is used as the reaction solvent in the [Pre-Step 2], potassium hydride (for example, 1.0 equivalent or less of potassium hydride relative to the compound represented by the general formula (i)) is used as the alkali metal compound, and THF is used as the polymerization solvent in the [Step a]. As the reaction in the [Pre-Step 2] progresses, potassium hydride in a powder form decreases and hydrogen is produced. By confirming whether the precipitation of a salt and the cloudiness in the reaction solution are observed or not when all of the potassium hydride is finally reacted without the precipitation of the polymerization initiator represented by the general formula (I) in THF, the solubility of the polymerization initiator in the polymerization solvent in the subsequent [Step a] can be confirmed in advance.

Moreover, as another method for confirming the solubility of the polymerization initiator represented by the general formula (I) in the polymerization solvent for use in the [Step a], the method as described below can be given as an example, although this is not limited thereto. As described above, the compound represented by the general formula (i) is reacted with the alkali metal or the alkali metal compound to synthesize the polymerization initiator represented by the general formula (I), and then the solvent and the reagents other than the polymerization initiator represented by the general formula (I) are removed by a usual method to extract the polymerization initiator represented by the general formula (I). The obtained polymerization initiator represented by the general formula (I) is dissolved in the polymerization solvent to be used in the subsequent [Step a] at a concentration of, for example, 20 wt. %, and whether the precipitation of a salt and the cloudiness are observed or not can be confirmed by visual observation.

As described above, the polymerization of an alkylene oxide with a polymerization initiator prepared with a water-containing monohydric alcohol that is a polymerization initiator raw material produces a diol polymer as by-product. Separation of a diol polymer from the target substance is extremely difficult, and it is likely that the intended performance of a polymer micellizing agent cannot be achieved with the direct use of the polymer which contains a diol polymer or impurities derived therefrom. Therefore, in the polymerization reaction in the subsequent [Step a], the water content in the reaction system comprising the compound (polymerization initiator) represented by the general formula (I) is dissolved is preferably reduced to be as low as possible. Regarding this, a compound represented by the general formula (i) with, for example, $R_A^{1a}=R_A^{1b}=$a triethylsilyl group, $R_A^2=CH_2CH_2 CH_2$, $R_A^3=O CH_2CH_2$, and a high boiling point of 120° C. (10 Pa), the compound being a precursor of the compound represented by the general formula (I), has a sufficient difference in boiling point from water, so that separation of water can be achieved by drying under reduced pressure. Therefore, it is preferred that, prior to the reaction of the compound represented by the general formula (i) with the alkali metal or the alkali metal compound in the [Pre-Step 2], the compound represented by the general formula (i) is sufficiently dried under reduced pressure and then distilled. In that case, the water content ratio of the compound represented by the general formula (i) after distillation is reduced, for example, to 50 ppm or less, preferably 10 ppm or less, more preferably 5 ppm or less. In this way, by reducing the water content of the compound represented by the general formula (i) that is a raw material of the polymer initiator to be as low as possible, by-production of the diol polymer can more favorably be suppressed in performing polymerization using the obtained polymerization initiator.

The concentration of a substance (mmol/g) that can function as a polymerization initiator in a reaction solution after completion of the [Pre-Step 2] (reaction solution after synthesis of the polymerization initiator) can be determined from the amount of substance of the raw material alcohol represented by the general formula (i) for use in the [Pre-Step 2] and the total weight of the reaction solution after completion of the [Pre-Step 2]. That is to say, the concentration of the substance that can function as the polymerization initiator in the reaction solution after completion of the [Pre-Step 2] can be determined by "amount of substance of raw material alcohol (i) used (mmol)/total weight of reaction solution (g) after completion of [Pre-Step 2]". The reason is because the raw material alcohol also functions as the polymerization initiator in the case in which the raw material alcohol represented by the general formula (i) is left in the reaction solution after completion of the [Pre-Step 2]. The reaction in the subsequent [Step a] is an equilibrium reaction, and therefore, the compound represented by the general formula (I) reacts as the polymerization initiator to produce a polymer, and an alkoxide at an end of the polymer eliminates a proton of the raw material alcohol (i) to allow the raw material alcohol to function as an alkoxide (polymerization initiator). However, as will be described later, the residual amount of the raw material alcohol in the reaction solution after completion of the [Pre-Step 2] is preferably as small as possible. The reaction solution after completion of the [Pre-Step 2] may be used as it is as a polymerization initiator solution in the subsequent [Step a].

Conventionally, sodium salts and potassium salts that are generally used polymerization initiators do not dissolve in polymerization solvents such as THF in many cases. In that case, in order to uniformly perform polymerization, an excessive amount of alcohol that is a initiator raw material has to be left (for example, in Japanese Patent No. 3050228, 13 mol of methanol to 2 mol of sodium methoxide that is a polymerization initiator). However, due to the presence of these alcohols in a reaction system, reduction in the polymerization rate is unavoidable. Consequently, crucial reaction conditions such as high temperature and high pressure are required for increasing the polymerization rate. In contrast, the alcohol derivative: that is used as a polymerization initiator in the present embodiment; that is represented by the formula (I); and the amino group of which is protected by a protective group has, in its structure, a structure that is similar to that of the polymerization solvent, and therefore is easily soluble to the polymerization solvent. For example, in the case in which $R_A^3$ has an oxyethylene structure, the compound represented by the general formula (I) is easily soluble to ether compounds including THF and diethylene glycol dimethyl ether. Therefore, the raw material alcohol does not have to be left in order to dissolve a polymerization initiator in a polymerization solvent. Therefore, the polymerization rate is increased, and polymerization under mild conditions is possible.

In this way, in order to obtain a sufficient reaction rate under mild conditions in the subsequent step a), a polymerization initiator having a small amount of a residual alcohol is preferably synthesized in the pre-step 2. Specifically, the ratio of the amounts of substances between the polymerization initiator represented by the general formula (I) and the initiator alcohol raw material represented by the general formula (i) is preferably 100:0 to 80:20 (mol %) after synthesis of the polymerization initiator represented by the general formula (I) from the alcohol as an initiator raw material represented by the general formula (i), and more preferably reaction is performed so that the ratio is 100:0 to 90:10 (mol %). In order to achieve that, the [Pre-Step 2] is preferably performed under the condition so that the number of moles of the alkali metal or the alkali metal compound used is 0.8 to 1.5, preferably 0.9 to 1.0 times the number of moles of the compound used and represented by the general formula (i).

It is also possible to distill away the alcohol as an initiator raw material represented by the general formula (i) under reduced pressure after synthesis of the polymerization initiator represented by the general formula (I). In that case, the raw material alcohol is preferably removed until the ratio of the amounts of substances between the polymerization initiator represented by the general formula (I) and the alcohol as an initiator raw material represented by the general formula (i) is 100:0 to 98:2 (mol %) after completion of the [Pre-Step 2], and more preferably the raw material alcohol is removed until the ratio is 100:0 to 99:1 (mol %). By reducing the amount of the residual raw material alcohol, it is possible to increase the polymerization rate in the subsequent [Step a] more.

In the present embodiment, as described above, even when the alcohol compound represented by the general formula (i), that is an initiator raw material and that is a factor of increasing the solubility of the polymerization initiator in polymerization solvents, and, on the other hand, also a factor of reducing the polymerization rate, is not left, it is possible to dissolve the compound represented by the general formula (I) as a polymerization initiator in polymerization solvents. A structure that plays the role is $R_A^3$ in the general formula (I), and, for example, in the case in which the polymerization solvent is THF, the compatibility between the polymerization initiator and the polymerization solvent is enhanced preferably by preparing $R_A^3$ so as to have a structure as represented by the general formula (VII) ($(OR_A^5)_p$), making it possible to dissolve the polymerization initiator in the polymerization solvent without a substantial presence of the raw material alcohol. As a result thereof, polymerization in a uniform system becomes possible, and synthesizing of a narrowly distributed polyalkylene glycol derivative under mild conditions becomes possible.

[Step a)]

The step a) is a step of reacting the compound represented by the general formula (I) (polymerization initiator) with an alkylene oxide in a polymerization solvent. According to the step a), the compound represented by the following general formula (I-1) can be obtained.

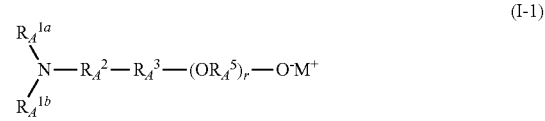

(I-1)

In the [Step a], the compound represented by the general formula (I) is reacted with an alkylene oxide after the compound represented by the general formula (I) is completely dissolved in the polymerization solvent. As described above, the compound represented by the general formula (I) is easily soluble to the polymerization solvent even when the compound represented by the general formula (i) that is the raw material alcohol is not substantially present. Among others, $R_A^3$ in the general formula (I) preferably has the alkylene oxide structure represented by the general formula (VII) ($-(OR_A^5)_p-$) in the viewpoint of high compatibility with polymerization solvents. That the compound represented by the general formula (I) can completely be dissolved in the polymerization solvent can be confirmed by, for example, the fact that the precipitation of a salt or cloudiness is not observed in the polymerization solvent by visual observation. In this case, the precipitation of a salt and the cloudiness are not desirably observed in a state in which the mass of the polymerization solvent is equal to or less than 10 times (and equal to or less than 1 times) the mass of the compound represented by the general formula (I). That is to say, the precipitation of a salt and the cloudiness are not desirably observed in a state in which the concentration of the compound represented by the general formula (I) in the polymerization solvent solution is 9.1 wt. % or more (and 50 wt. % or less). After confirming as described above, the polymerization solvent solution containing the compound represented by the general formula (I) may be used for polymerization reaction keeping the concentration as it is during the confirmation, or may be used for polymerization reaction in a diluted state by further adding the polymerization solvent. In addition, the amount of the polymerization solvent may be adjusted so as to be, for example, 1 to 50 times, preferably 2 to 25 times the mass of the alkylene oxide used at the time of starting the polymerization reaction.

Furthermore, as described above, the presence of the raw material alcohol becomes the factor of reducing the polymerization rate, and therefore the polymerization initiator is preferably used in a state in which the amount of the raw material alcohol is small in the [Step a]. For example, in the case in which the pre-step 2 is performed prior to the step a), the reaction product obtained in the pre-step 2 and containing the polymerization initiator represented by the general formula (I) and the raw material alcohol represented by the general formula (i), preferably in a ratio of the amounts of substances of 100:0 to 80:20 (the reaction product containing a small amount of the raw material alcohol), is preferably used by directly dissolving the reaction product in a polymerization solvent As the polymerization solvent for use in the [Step a], cyclic ether compounds having 4 to 10 carbon atoms or linear or branched ether compounds are preferably used in the viewpoint that compatibility with the polymerization initiator is high. Specific examples of the cyclic ether compound includes furan, 2,3-dihydrofuran, 2,5-dihydrofuran, 2,3-dimethylfuran, 2,5-dimethylfuran, tetrahydrofuran (THF), 2-methyltetrahydrofuran, 3-methyltetrahydrofuran, 2,5-dimethyltetrahydrofuran, 1,2-methylenedioxybenzene, 1,3-dioxolane, 2-methyl-1,3-dioxolane, 4-methyl-1,3-dioxolane, 2,2-dimethyl-1,3-dioxolane, 3,4-dihydro-2H-pyran, tetrahydropyran, 1,3-dioxane, 1,4-dioxane, 2,4-dimethyl-1,3-dioxane, 1,4-benzodioxane, 1,3,5-trioxane, and oxepane, although this is not limited thereto. Specific example of the linear or branched ether compound include monoethylene glycol dimethyl ether, diethylene glycol dimethyl ether, and triethylene glycol dimethyl ether, although this is not limited thereto. THF in particular is preferably used. Moreover, polymerization solvents other than the ether compounds may be used, and specific examples thereof include aromatic hydrocarbons such as benzene, toluene, and xylene, although this is not limited thereto. The polymerization solvent for use may be a single solvent, or may be used in combination of two or more. In the case in which the polymerization solvents are used in combination, the combination and the mixing ratio is not particularly limited.

The amount of the polymerization solvent used for polymerization reaction is, for example, 1 to 50 times, preferably 2 to 30 times, more preferably 3 to 20 times the mass of the alkylene oxide used, although this is not particularly limited. The polymerization solvent distilled with, for example, a dehydrating agent such as metal sodium is preferably used. The water content of the polymerization solvent is, for example, 50 ppm or less, preferably 10 ppm or less, more preferably 5 ppm or less.

Specific example of the alkylene oxide used includes ethylene oxide, propylene oxide. Among them, ethylene oxide is preferred in the viewpoint of high polymerizability. The ratio of amounts of use between the compound used for polymerization reaction and represented by the general formula (I) and the alkylene oxide is, for example, 1:1 to 1:450, preferably 1:10 to 1:400 as the ratio of the amounts of substances of the compound represented by the general formula (I): the alkylene oxide, although this is not particularly limited thereto.

In the step a), for example, the alkylene oxide may be added in one batch to a reaction system with the compound represented by the general formula (I) dissolved in the polymerization solvent, or the alkylene oxide may successively be added to the reaction system. Or, a solution of the alkylene oxide dissolved in the polymerization solvent may be dripped into the reaction system. The polymerization may be performed at a temperature of, for example, 30 to 80° C., preferably 50 to 80° C., more preferably 60 to 80° C. The pressure during polymerization is, for example, 1.0 MPa or less, preferably 0.5 MPa or less. The degree of progress of polymerization reaction can be monitored with GPC, and when no change is observed in conversion ratio of the alkylene oxide, the completion can be assumed. As described above, the present embodiment is advantageous in that crucial reaction conditions such as high temperature and high pressure are not required in polymerization.

[Step b)]

The step b) is a step of reacting the compound represented by the general formula (I-1) obtained in the step a) with the compound represented by the following general formula (I-2). Through the step b), the compound represented by the following general formula (II) can be obtained.

$$R_A^4(OR_A^5)_k L \tag{I-2}$$

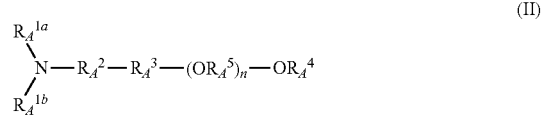

In synthesizing the compound represented by the general formula (II) in the step b), for example, the compound represented by the general formula (I-2) may directly be added to the reaction liquid (reaction liquid containing (I-1)) after completion of the reaction in step a), or the compound represented by the general formula (I-2) may be dissolved for use in a proper solvent as needed. Specific examples of the solvent used include ethers such as THF and 1,4-dioxane, and aromatic hydrocarbons such as benzene, toluene, and xylene. The amount of the solvent used is, for example, 1 to 50 times, preferably 2 to 10 times, more preferably 2 to 5 times the mass of the compound represented by the general formula (I-2), although this is not particularly limited thereto. The reaction may be performed at a temperature of, for example, 0 to 100° C., preferably at a temperature of 40 to 70° C., and the reaction system may be cooled or heated as needed. The amount of the compound represented by the general formula (I-2) used is, for example, 1 to 50 equivalents, preferably 1 to 40 equivalents, more preferably 1 to 30 equivalents, relative to the number of moles of the compound represented by the general formula (I-1). The degree of progress of reaction can be monitored with $^1$H-NMR, and when a peak derived from a hydroxy group produced in quenching the reaction liquid with water disappears, the completion can be assumed.

Although the reaction in the step b) proceeds without a catalyst, a basic catalyst may be added for further acceleration of the reaction. As the basic catalyst, hydroxides such as sodium hydroxide, potassium hydroxide, and tetramethylammonium hydroxide, carbonates such as sodium carbonate, potassium carbonate, and cesium carbonate, metal alkoxides such as sodium methoxide, sodium ethoxide, and potassium t-butoxide, metal hydrates such as sodium hydrate and potassium hydrate, and primary, secondary, and tertiary aliphatic amines, conjugated amines, aromatic amines, heterocyclic amines, and ammonia water may be used, although this is not limited thereto. The amount of the basic catalyst used is, for example, 0.1 to 30 times, preferably 1 to 20 times the number of moles of the compound represented by the general formula (I-1).

In the step b), an alkaline adsorbent may further be used in order to separate an alkali metal salt produced through the reaction of the compound represented by the general foimula (I-1) with the compound represented by the general formula (I-2). As the suitable alkali adsorbent, an aluminum hydroxide (e.g. "KYOWADO 200" made by Kyowa Chemical Industry Co., Ltd.), a synthesized hydrotalcite (e.g. "KYOWADO 500" made by Kyowa Chemical Industry Co., Ltd.), a synthesized magnesium silicate (e.g. "KYOWADO 600" made by Kyowa Chemical Industry Co., Ltd.), a synthesized aluminum silicate (e.g. "KYOWADO 700" made by Kyowa Chemical Industry Co., Ltd.), and an aluminum oxide/magnesium oxide solid solution (e.g. "KW-2000" made by Kyowa Chemical Industry Co., Ltd. and "TOMITA AD 700NS" made by Tomita Pharmaceutical Co., Ltd.) are used, however the adsorption material is not limited thereto. Among them, KW-2000 is preferred because of high ion trapping ability. The amount of the alkali adsorbent used may be 0.01 to 10 times, preferably 0.1 to 8 times, more preferably 0.3 to 6 times the mass of the compound represented by the general formula (II), although this is not particularly limited thereto. An alkali adsorbent may be directly fed into the reaction liquid at the time of completion of the reaction of the compound represented by the general formula (I-1) with the compound represented by the general formula (I-2), or may be fed into the reaction liquid after the reaction is completed and the produced alkali metal salt is filtered. The adsorbent may be removed by filtration after the reaction was performed for 0.5 to 6 hours after feeding the adsorbent, however the reaction time is not particularly limited. As a method of using the adsorption material, the adsorption material may be used as a batch system and added into the reaction solution to perform stirring, or the adsorption material may be used as a column system and the reaction solution may be allowed to pass through a column where the adsorption material is filled. Specific example of the solvent in the case of performing adsorption treatment include ethers such as THF and 1,4-dioxane, aromatic hydrocarbons such as benzene, toluene, and xylene, esters such as ethyl acetate, n-butyl acetate, and γ-butyrolactone, ketones such as acetone, methyl ethyl ketone, and methyl isobutyl ketone, dimethyl sulfoxide (DMSO), N,N-dimethylformamide (DMF), and acetonitrile, although this is not limited thereto. The aromatic hydrocarbons such as benzene, toluene, and xylene are preferred for the purpose of enhancing the ability of adsorbing salts. These solvents may be used singly or in combinations of two or more. In that case, the mixing ratio is not particularly limited.

In the case in which the compound represented by the general formula (II) is solid, the compound represented by the general formula (II) may be extracted as solid for use before the subsequent step c). In that case, crystallization may be performed by dripping the reaction liquid directly or after concentration to a poor solvent. In concentrating the reaction liquid, the concentration of the compound represented by the general formula (II) is adjusted to be, for example, 10 to 50 mass %, preferably 15 to 45 mass %, more preferably 20 to 40 mass %.

In concentrating the reaction liquid, crystallization may be performed after solvent substitution with a good solvent of the compound represented by the general formula (II). In that case, specific examples of the good solvent include ethers such as THF and 1,4-dioxane, aromatic hydrocarbons such as benzene, toluene, and xylene, esters such as ethyl acetate, n-butyl acetate, and γ-butyrolactone, ketones such as acetone, methyl ethyl ketone, and methyl isobutyl ketone, dimethyl sulfoxide (DMSO), N,N-dimethylformamide (DMF), and acetonitrile, although this is not limited thereto. These solvents may be used singly or in combination of two or more. In that case, the mixing ratio is not particularly limited. The concentration of the compound represented by the general formula (II) after solvent substitution is, for example, 5 to 50 mass %, preferably 10 to 40 mass %, more preferably 10 to 30 mass %.

The poor solvent for use has a low solubility for the compound represented by the general formula (II). Examples of the suitable poor solvent for use include hydrocarbon such as hexane, heptane, octane, nonane, decane, cyclopentane, cyclohexane, cycloheptane, and cyclooctane, and ethers such as diethyl ether, diisopropyl ether, and di-n-butyl ether. The amount of the poor solvent used is, for example, 5 to 100 times, preferably 5 to 50 times, more preferably 5 to 20 times the mass of a compound represented by the general formula (II), although this is not particularly limited thereto. The poor solvents may be used singly, or the poor solvent may be mixed with a different solvent for use. Examples of the different solvent for mixing include esters such as ethyl acetate, n-butyl acetate, and γ-butyrolactone, ketones such as acetone, methyl ethyl ketone, and methyl isobutyl ketone, hydrocarbons such as benzene, toluene, xylene, and cumene, ethers such as tetrahydrofuran, diethyl ether, and 1,4-dioxane, alcohols such as methanol, ethanol, isopropyl alcohol, and ethylene glycol monomethyl ether, dimethyl sulfoxide (DMSO), N,N-dimethylformamide (DMF), and acetonitrile, although this is not limited thereto.

In the step b), after precipitation of solid by crystallization, the solid may be washed for purification as needed. Preferably the solvent for use in washing is the same poor solvent as described above, although this is not particularly limited thereto. The amount of the washing solvent used is also not particularly limited. The produced solid is dried under reduced pressure, so that a compound represented by the general formula (II) can be extracted as solid.

In the case in which water is mixed during polymerization of an alkylene oxide in the previous step a), a diol derivative is produced as described previously, and a compound represented by the following general formula (VIII) is produced further through the step b).

(In the general formula (VIII), $R_A^4$ and $R_A^5$ are the same as defined in the general formula (II), and q represents an integer of 1 to 890)

The diol derivative represented by the general formula (VIII) is produced in the case in which water functions as a polymerization initiator, and therefore the polymerization progresses from both ends, which is different from the case in which the polymerization initiator represented by the general formula (I) works. Therefore, q is about twice r in the general formula (I-1), and represents an integer of, for example, 1 to 890, preferably an integer of 20 to 790, more preferably an integer of 40 to 690. In the present embodiment, the polymerization reaction is preferably performed in a state in which the water content in the reaction system is suppressed at a low level as described above, so that the production of the diol derivative such as described above can be suppressed.

Moreover, in the conventional synthesis methods described in Japanese Patent No. 3050228 and Japanese Patent No. 3562000, the polymerization end is converted to a cyanoethyl group, and subsequently to an amino group, thus a diol impurity finally leads to a compound having amino groups at both end. The compound has an end structure similar to that of the target compound, and therefore cannot be separated by such a purification method with a cation exchange resin as will be described later. In contrast, in the present embodiment, the diol derivative represented by the general formula (VIII) has a different end structure from that of the target compound represented by the general formula (III). It is therefore possible to separate the diol derivative represented by the general formula (VIII) by, for example, such purification with a cation exchange resin as will be described later, and, as a result thereof, a high-purity polyalkylene glycol derivative (III) having an amino group may be synthesized.

[Step c)]

In the step c), the protective group in the compound represented by the general formula (II) obtained in the step b) is deprotected. The deprotection is preferably performed without using a heavy metal catalyst. The heavy metal catalyst here is a catalyst using a heavy metal such as, for example, Co, Ni, Pd, Pt, Rh, Ru, Cu, and Cr as a raw material. As a method for performing deprotection without using a heavy metal catalyst in the step c), for example, in the case in which $R_A^{1a}$ and/or $R_A^{1b}$ in the general formula (II) represent a silyl group (in the case of (P-1)), water or an alcohol ($R^6OH$: wherein $R^6$ represents a hydrocarbon group having 1 to 5 carbon atoms) is reacted with the compound represented by the general formula (II) in the presence of an acid catalyst, so that conversion to the compound represented by the general formula (III) may be performed. Specific examples and the amount of the acid catalyst used are as will be described later in the embodiment 2.

Moreover, in the case in which $R_A^{1a}$ and/or $R_A^{1b}$ represent a tert-butyloxycarbonyl group (in the case of (P-2)) for example, deprotection may be performed by allowing a strong acid such as trifluoroacetic acid and hydrochloric acid to act on the compound represented by the general formula (II). The amount of the strong acid used is, for example, 0.01 to 1000 equivalents, preferably 0.1 to 100 equivalents, more preferably 1 to 10 equivalents, relative to the number of moles of the compound represented by the general formula (II).

In the case in which $R_A^{1a}$ and $R_A^{1b}$ represent an N-phthaloyl group (in the case of (P-3)) for example, the phthaloyl group may be eliminated by reacting a hydrazine hydrate with the compound represented by the general formula (II) in an alcohol. Examples of the alcohol for use include methanol, ethanol, n-propyl alcohol, isopropyl alcohol, n-butyl alcohol, sec-butyl alcohol, and tert-butyl alcohol. The amount of the alcohol used is, for example, 1 to 100 times, preferably 3 to 50 times, more preferably 5 to 10 times the mass of the compound represented by the general formula (II). The amount of the hydrazine hydrate used is, for example, 1 to 50 equivalents, preferably 2 to 20 equivalents, more preferably 3 to 10 equivalents, relative to the number of moles of the compound represented by the general formula (II).

In the case in which $R_A^{1a}$ and/or $R_A^{1b}$ represent a benzyl group or an ally group (in the case of (P-4)) for example, deprotection of the compound represented by the general formula (II) may be performed under the condition of Birch reduction in which liquid ammonium and metal sodium are used. The amount of liquid ammonium used is, for example, 1 to 100 times, preferably 3 to 50 times, more preferably 5 to 10 times the mass of the compound represented by the general formula (II). The amount of metal sodium used is, for example, 2 to 50 equivalents, preferably 2 to 10 equivalents, more preferably 2 to 5 equivalents, relative to the number of moles of the compound represented by the general formula (II). As in the examples above, deprotection may be performed by appropriately selecting the condition where a heavy metal catalyst is not used, and the condition is not limited.

In addition, deprotection in the step c) is preferably performed without using a heavy metal catalyst as described above; however, it is possible to perform the deprotection with a heavy metal catalyst. For example, in the case in which the polyalkylene glycol derivative obtained by the production method of the present invention is used for applications in which mixing of a heavy metal does not cause a substantial problem (such as, for example, cosmetics, hair growth agents, and surfactants), it is considered that the heavy metal catalyst may be used in the step c). In the case in which the step c) is performed with a heavy metal catalyst, the general heavy metal catalyst as described above may be used according to a usual method, and the method is not particularly limited.

In the case in which deprotection is performed with an acid catalyst, a produced amine represented by the general formula (III) and an acid forms a salt and the acid cannot be removed in some cases. In such cases, when the produced basic compound is added to and is reacted with the acid, a salt of the added basic compound and the acid is formed, and therefore, the amine represented by the general formula (III) may be extracted. The produced salt may be removed by filtration. In the case in which the produced salt is incorporated into the polymer, the salt may be removed with an adsorption material. As the adsorption material, the adsorption materials as described in the above-mentioned [Step b] may be used, although this is not particularly limited thereto. The amount of adsorbent used may be 0.01 to 10 times, preferably 0.1 to 8 times, more preferably 0.3 to 6 times the mass of the compound represented by the general formula (III), although this is not particularly limited. Examples of the basic compound for use include potassium hydroxide, sodium hydroxide, potassium tert-butoxide, sodium methoxide, and potassium methoxide, although this is not limited thereto. The amount of the basic compound added is, for example, 1 to 10 equivalents, preferably 1 to 5 equivalents, more preferably 1 to 2 equivalents, relative to the number of moles of the acid catalyst for use in deprotection. As a solvent for use in filtration, the reaction solvent may directly be used, or filtration may be performed after solvent substitution with a solvent in which a salt is easy to precipitate. Specific examples of the solvent in which a salt is easy to precipitate include ethers such as THF and 1,4-dioxane, aromatic hydrocarbons such as benzene, toluene, and xylene, esters such as ethyl acetate, n-butyl acetate, and γ-butyrolactone, ketones such as acetone, methyl ethyl ketone, and methyl isobutyl ketone, dimethyl sulfoxide (DMSO), N,N-dimethylformamide (DMF), and acetonitrile, although this is not limited thereto. The aromatic hydrocarbons such as benzene, toluene, and xylene are preferred for the purpose of enhancing the filterability. These solvents may be used alone or in combination of two or more. In that case, the mixing ratio is not particularly limited.

In removing the acid catalyst, the adsorption material may directly be added to the reaction system without adding a basic compound; however, in that case, there is a possibility that the filterability is lowered. Therefore, the adsorption material is preferably used after the above-mentioned addition of the basic compound.

For example, crystallization of the compound represented by the general formula (III) may be performed with a poor solvent directly after deprotection, crystallization may also be performed after solvent substitution with a good solvent, or crystallization may also be performed after the above-mentioned reaction with the basic compound and the treatment with an adsorption material. In that case, specific examples of the good solvent include ethers such as THF and 1,4-dioxane, aromatic hydrocarbons such as benzene, toluene, and xylene, esters such as ethyl acetate, n-butyl acetate, and -γ-butyrolactone, ketones such as acetone, methyl ethyl ketone, and methyl isobutyl ketone, dimethyl sulfoxide (DMSO), N,N-dimethylformamide (DMF), and acetonitrile, although this is not limited thereto. These solvents may be used alone or in combination of two or more. In that case, the mixing ratio is not particularly limited. The concentration of the compound after solvent substitution is, for example, 5 to 50 mass %, preferably 10 to 40 mass %, more preferably 10 to 30 mass %.

The poor solvent for use in the crystallization of the compound represented by the general formula (III) has a low solubility for the compound represented by the general formula (III). Specific examples of the suitable poor solvent for use include hydrocarbon such as hexane, heptane, octane, nonan, decane, cyclopentane, cyclohexane, cycloheptane, and cyclooctane, and ethers such as diethyl ether, diisopropyl ether, and di-n-butyl ether. The amount of the poor solvent used is, for example, 5 to 100 times, preferably 5 to 50 times, more preferably 5 to 20 times the mass of a compound represented by the general formula (III), although this is not particularly limited thereto. The poor solvents may be used alone or in combination of two or more. Alternatively, the poor solvent may be mixed with a different solvent for use. Examples of the different solvent for mixing include esters such as ethyl acetate, n-butyl acetate, and γ-butyrolactone, ketones such as acetone, methyl ethyl ketone, and methyl isobutyl ketone, hydrocarbons such as benzene, toluene, xylene, and cumene, ethers such as tetrahydrofuran, diethyl ether, and 1,4-dioxane, alcohols such as methanol, ethanol, isopropyl alcohol, and ethylene glycol monomethyl ether, dimethyl sulfoxide (DMSO), N,N-dimethylformamide (DMF), and acetonitrile, although this is not limited thereto. In the case of using a mixture of two or more solvents as a poor solvent, the mixing ratio is not particularly limited.

In the [Step c], after precipitation of solid of the compound represented by the general formula (III) by crystallization, the solid may be washed for purification as needed. The solvent for use in washing is desirably the same poor solvent as described above, although this is not particularly limited. The amount of the washing solvent used is also not particularly limited. The produced solid is dried under reduced pressure, so that the compound represented by the general formula (III) can be extracted as a solid.

In the present embodiment, since the amino group of the compound represented by the general formula (III) is obtained by the deprotection in the [Step c] as described above, by-products (compounds represented by the following (IV) to (VI)), that can be produced by, for example, a method described in Japanese Patent No. 3562000, are not substantially produced, and a narrowly distributed and high-purity polyalkylene glycol derivative having an amino group at an end, the polyalkylene glycol derivative represented by the general formula (III), can finally be synthesized. In contrast, in the case in which a cyanoethylated compound is subjected to hydrogen reduction to lead to a polyalkylene glycol derivative having an amino group by, for example, a method described in Japanese Patent No. 3562000, the hydrogen reduction is accompanied by β-elimination of acrylonitrile, and therefore, production of a PEG derivative represented by the following general formula (VI) cannot be prevented. Moreover, in the conventional method, there is a possibility that a secondary and tertiary amine compounds represented by the following general formula (IV) and (V) are produced in the hydrogen reduction process due to addition of an amine as a product to an imine as a reduction intermediate of nitrile. The side reactions may be suppressed by adding ammonia or acetic acid to the reaction system; however, it is difficult to completely control the side reactions by a conventional method.

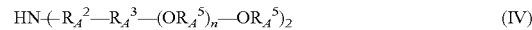

$$HN(R_A^2-R_A^3-(OR_A^5)_n-OR_A^5)_2 \quad (IV)$$

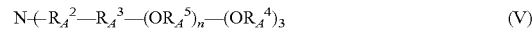

$$N(R_A^2-R_A^3-(OR_A^5)_n-OR_A^4)_3 \quad (V)$$

$$H-(OR_A^5)_n-OR_A^4 \quad (VI)$$

(In the general formulas (IV) to (VI), $R_A^2$, $R_A^3$, $R_A^4$, $R_A^5$, and n are the same as $R_A^2$, $R_A^3$, $R_A^4$, $R_A^5$, and n in the general formula (III).)

[Post-Treatment Step]

After the step c), a post-treatment step of purifying the compound represented by the general formula (III) with a strong acid cation exchange resin may optionally be performed. Moreover, in the case in which the protective group in the compound represented by the general formula (II) obtained in the step b) is a protective group that is deprotectable with an acid, this post-treatment step with a strong acid cation exchange resin may be performed after the step b) directly, so that deprotection may be performed in parallel and the process may be simplified. That is to say, in this case, the step c) (step of deprotecting the compound represented by the general formula (II) to obtain the compound represented by the general formula (III)) may specifically be performed by the following operations of the post-treatment step.

In the post-treatment step, the reaction product (crude product) containing the compound represented by the general formula (III) obtained in the step c) or the reaction product (crude product) containing the compound represented by the general formula (II) obtained in the step b) is reacted with the strong acid cation exchange resin. Examples of the method for reacting the crude products obtained in the step c) or the step b) with a strong acid cation exchange resin include: flowing the solution of the crude products in a column filled with the ion exchange resin to cause adsorption; and circulating the solution of the crude products between a cartridge filled with the resin and the reaction tank for the step c) or the step b); although this is not particularly limited. Moreover, in the case in which the post-treatment step is performed after the step b), the compound represented by the general formula (II) is reacted with water or a monohydric alcohol solvent having 1 to 5 carbon atoms in the presence of the catalyst of the strong acid cation exchange resin, so that the compound represented by the general formula (III) may be adsorbed by the strong acid cation exchange resin after deprotection.

Specific examples of the strong acid cation exchange resin including AMBERLITE series (IR120B, IR124B, 200CT, and 252) made by Organo Corporation, AMBERJET series (1020, 1024, 1060, and 1220) made by Organo Corporation, DIAION series (e.g. SK104, SK1B, SK110, SK112, PK208, PK212, PK216, PK218, PK220, PK228, UBK08, UBK10, UBK12, UBK510L, UBK530, and UBK550) made by Mitsubishi Chemical Corporation, DOWEX series (50W×2 50-100, 50W×2 100-200, 50W×4 100-200, 50W×8 50-100, 50W×8 100-200, 50W×8 200-400, HCR-S, and HCR-W2 (H)) made by Dow Chemical Co., are suitably used although this is not limited thereto. The amount of the strong acid cation exchange resin used is, for example, 1 to 50 times, preferably 1 to 30 times, more preferably 1 to 20 times the mass of the compound represented by the general formula (III).

In the case of using a strong acid cation exchange resin, the strong acid cation exchange resin may be treated with an acid compound prior to use, since commercially available strong acid cation exchange resins are often in an alkali metal sulfonate salt state, the pretreatment with an acid compound regenerates sulfo groups, so that the reaction efficiency can be improved. In this case, examples of the acid compound for use include inorganic acids such as hydrochloric acid, sulfuric acid, nitric acid, phosphoric acid, and perchloric acid, although this is not limited thereto. The amount of the acid compound used is, for example, 1 to 15 times, preferably 1 to 10 times, more preferably 1 to 8 times the mass of the strong acid cation exchange resin. After treatment of the strong acid cation exchange resin with an acid compound, the acid compound may be separated from the resin by washing with water, and water may be separated by a water-soluble organic solvent such as methanol and ethanol as needed.

In this post-treatment step, impurities other than the compound represented by the general formula (III) (compound represented by the general formula (VIII) and salts) may also be separated. That is to say, the crude products after the step c) or the step b) are reacted with a strong acid cation exchange resin to adsorb the compound represented by the general formula (III) by the strong acid cation exchange resin, and then the strong acid cation exchange resin is washed with water or the monohydric alcohol having 1 to 5 carbon atoms, so that substances other than the target compound represented by the general formula (III) can be separated. Examples of the monohydric alcohol having 1 to 5 carbon atoms for use in the washing include methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol, although this is not limited thereto. In performing washing, water or a monohydric alcohol may be used alone, or a mixture of water and one or more alcohols or a mixture of two or more alcohols may be used. In that case, the mixing ratio is not particularly limited. The amount of water or a monohydric alcohol having 1 to 5 carbon atoms used is, for example, 1 to 30 times, preferably 1 to 20 times, more preferably 1 to 10 times the mass of the strong acid cation exchange resin for use, although this is not particularly limited.

The strong acid cation exchange resin with the adsorbed compound represented by the general formula (III) is reacted with a basic compound in water or a monohydric alcohol having 1 to 5 carbon atoms, so that a compound represented by the general formula (III) may be extracted in water or the monohydric alcohol. In performing the reaction, water or the monohydric alcohol may be used alone, or a mixture of water and one or more alcohols or a mixture of two or more alcohols may be used. In that case, the mixing ratio is not particularly limited. Examples of the method for reacting a strong acid cation exchange resin and a basic compound include: flowing the solution of basic compound in a column filled to cause reaction; and circulating the solution of the basic compound between a cartridge filled with the resin and the reaction tank for the [Step c]; although this is not particularly limited.

Examples of the monohydric alcohol for use in the extraction include methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol. The amount of water or a monohydric alcohol used is, for example, 1 to 30 times, preferably 1 to 20 times, more preferably 1 to 10 times the mass of the strong acid cation exchange resin for use, although this is not particularly limited.

As the basic compound for use in the extraction, ammonia dissolved in water or an organic solvent (e.g. ammonia water and methanol solution of ammonia) may be suitably used, and primary, secondary and tertiary aliphatic amines, mixed amines, aromatic amines, and heterocyclic amines may be also used. Examples of the primary aliphatic amines include methylamine, ethylamine, n-propylamine, isopropylamine, n-butylamine, isobutylamine, sec-butylamine, tert-butylamine, and ethylene diamine; examples of the secondary aliphatic amines include dimethylamine, diethylamine, di-n-propylamine, diisopropylamine, di-n-butylamine, diisobutylamine, di-sec-butylamine; examples of the tertiary aliphatic amines include trimethylamine, triethylamine, tri-n-propylamine, triisopropylamine, tri-n-butylamine, triisobutylamine, and tri-sec-butylamine; examples of the mixed amines include dimethylethylamine, methylethylpropylamine, benzylamine, phenethylamine, benzyldimethylamine; specific examples of the aromatic amines and the heterocyclic amines include aniline derivatives (e.g. aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, and pyridine derivatives (e.g. pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), although this is not limited thereto. Alternatively an alkali aqueous solution such as potassium hydroxide and sodium hydroxide may be used as a basic compound. The amount of the basic compound used is, for example, 0.1 to 100 times, preferably 0.1 to 10 times, more preferably 0.1 to 5 times the mass of the strong acid cation exchange resin for use.

In this way, the steps a) to c) are performed, or the pre-steps 1 and 2 and/or the post-treatment step are further performed optionally before and/or after the steps a) to c), so that the compound represented by the general formula (III) (narrowly distributed and high-purity polyalkylene glycol derivative having an amino group at an end) can be produced.

That is to say, according to another aspect, the present invention relates to a narrowly distributed and high-purity polyalkylene glycol derivative having an amino group at an end, the polyalkylene glycol derivative obtained in the above-described production method and represented by the general formula (III).

Regarding the compound: obtained after performing the steps a) to c), or obtained by further performing the pre-steps 1 and 2 and/or the post-treatment step optionally before and/or after the steps a) to c); and represented by the general formula (III), the initiation reaction is sufficiently faster than the propagation reaction during polymerization, the amount of water mixed as a factor of termination reaction is small, and further the polymerization initiator is uniformly dissolved in the polymerization solvent, so that a narrowly distributed polymer can be obtained. That is to say, the compound produced by the production method of the present embodiment and represented by the general formula (III) is narrowly distributed, and the dispersity (weight average molecular weight (Mw)/number average molecular weight (Mn)) is, for example, 1.0 to 1.20, preferably 1.0 to 1.10, more preferably 1.0 to 1.06. Moreover, the molecular weight of the compound represented by the general formula (III) produced by the production method of the present invention is preferably 5,000 to 25,000, more preferably 8,000 to 15,000 as the weight average molecular weight (Mw). The molecular weight and dispersity of a polymer in the present embodiment are defined as values obtained in the case in which measurement is performed with gel permeation chromatography (hereinafter, alleviated as "GPC").

Regarding the amount of compounds represented by the general formulas (IV) and (V) mixed in the product obtained after performing the steps a) to c), or obtained by further performing the pre-steps 1 and 2 and/or the post-treatment step optionally before and/or after the steps, a) to c) expressed by an area content ratio (%), the area of the compounds represented by the general formulas (IV) and (V) is preferably 3% or less, more preferably 2% or less, relative to the total area of the compounds represented by the general formulas (III), (IV), and (V). Most preferably, the obtained product does not contain any one of the compounds represented by the general formula (IV) and represented by the general formula (V). According to the present embodiment, any one of the compound represented by the general formula (IV) and the compound represented by the general formula (V) are not actually produced. The secondary amine represented by the general formula (IV) and the tertiary amine represented by the general formula (V) have a molecular weight twice or three times as large as the molecular weight of the polyalkylene glycol derivative represented by the general formula (III) as a main product, and, therefore, the amount of these amines produced can be confirmed by GPC.

The amount of the compound represented by the general formula (VI) mixed in the product obtained after performing the steps a) to c), or obtained by further performing the pre-steps 1 and 2 and/or the post-treatment step optionally before and/or after the steps a) to c) is preferably 2 mol % or less, more preferably 1 mol % or less, relative to the total amount of substances of the compound represented by the general formula (III) and the compound represented by the general formula (VI). Most preferably, the obtained product does not contain a compound represented by the general formula (VI). According to the present embodiment, a compound represented by the general formula (VI) is not actually produced. The compound represented by the general formula (VI) contains an alcohol as a functional group, and therefore the content ratio in terms of composition ratio (mol %) can be determined by comparing with a methylene of amine of the polyalkylene glycol derivative represented by the general formula (III) as a main product from proton magnetic resonance (1H-NMR).

Moreover, the product obtained after performing the steps a) to c), or obtained by further performing the pre-steps 1 and 2 and/or the post-treatment step optionally before and/or after the steps a) to c) does not substantially contain such by-products (compounds represented by the general formulas (IV) to (VI)) that can be produced in the conventional methods as described above. Specifically, $X_A/(X_A+X_B)$ is preferably 0.95 or more, more preferably 0.97 or more, where $X_A$ represents the total amount of the compound represented by the general formula (III) as the main product, $X_B$ represents the total amount of by-products containing the compounds represented by the general formula (IV), the general formula (V), and the general formula (VI) respectively, and both $X_A$ and $X_B$ are converted from the measurement results by GPC and 1H-NMR as described above. Most preferably, the obtained product does not contain such by-products as described above. According to the present embodiment, these by-products are not actually produced.

Moreover, the content of heavy metal impurities measured by a high frequency inductively coupled plasma mass spectrometer (ICP-MS) in the product obtained after performing the steps a) to c), or obtained by further performing the pre-steps 1 and 2 and/or the post-treatment step optionally before and/or after the steps a) to c) is preferably 100 ppb or less, more preferably 10 ppb or less. The measurement of the amount of heavy metal impurities in the product described above is generally performed with the above-described ICP-MS; however, the measurement method is not limited thereto. A polymer sample, when analyzed with an ICP-MS, may be diluted with a solvent for measurement. It is essential that a solvent used dissolve the polymer and not contain a metal. Ultrapure water and N-methyl-2-pyrrolidone for electronic industry are particularly preferred; however, the solvent is not limited thereto. The dilution ratio is preferably 10 to 100,000 times, more preferably 50 to 1,000 times, although this is not limited thereto.

As described above, in the conventional synthesis methods described in, for example, Japanese Patent No. 3050228 and Japanese Patent No. 3562000, a cyano group is converted to an aminomethyl group with a Raney nickel catalyst, and therefore, for example, in the case in which the polyalkylene glycol derivative is used in medical supplies, there is concern over mixing of a heavy metal in the product. According to "ICH Q3D: GUIDELINES FOR ELEMENTAL IMPURITIES Draft ICH consensus Guideline" reported in International Conference on Harmonization of Technical Requirements for Registration of Pharmaceuticals for Human Use, as elementary impurities that need risk assessment among elementary impurities, As, Pb, Cd, and Hg are listed in Class 1, V, Mo, Se, and Co are listed in Class 2A, Ag, Au, Tl, Pd, Pt, Ir, Os, Rh, and Ru are listed in Class 2B, and Sb, Ba, Li, Cr, Cu, Sn, and Ni are listed in Class 3. Examples of the heavy metal for use in hydrogen reduction include Co, Ni, Pd, Pt, Rh, Ru, Cu, and Cr; however, these metals are listed as the metals that need risk assessment, and reducing the mixing amount thereof will be required more and more in the future. In this regard, since the method of the present embodiment does not require the use of a heavy metal catalyst as described above, a heavy metal is not mixed in a product. As a result thereof, the method of the present invention is a production method that is particularly suitable for obtaining a compound represented by the general formula (III) for use in medical supplies.

Embodiment 2

In the present invention, the compound represented by the following general formula (1) and/or the following general formula (2) the amino group of which is silyl-protected (hereinafter, sometimes noted as "compounds represented by the general formulas (1) and/or (2)" as an abbreviation, and the same applies to the other compounds) are preferably used as a polymerization initiator, among the above-described embodiment 1. The compounds represented by the general formulas (1) and/or (2) have advantages of having a high solubility to polymerization solvents, moreover having a high stability as a polymerization initiator, and furthermore being easily deprotectable with an acid after polymerization. Hereinafter, the embodiment in which the compounds represented by the general formulas (1) and/or (2) are used as a polymerization initiator is sometimes referred to as "embodiment 2". In addition, the present embodiment 2 is a preferred embodiment of the embodiment 1, and therefore, the description is omitted in the overlapping portions.

The compound represented by the following general formula (1) represents a compound represented by the general formula (I) in the embodiment 1 where $R_A^{1a}$ and $R_A^{1b}$ each have a structure represented by $Si(R^1)_3$, $R_A^2$ represents $R^2$, and $R_A^3$ represents $(OR^5)_m$.

Moreover, the compound represented by the following general formula (2) represents a compound represented the general formula (I) in the embodiment 1 where $R_A^{1a}$ and $R_A^{1b}$ each have a structure represented by $Si(R^1)_3$, $R_A^2$ represents $R^3$, and $R_A^3$ represents a single bond.

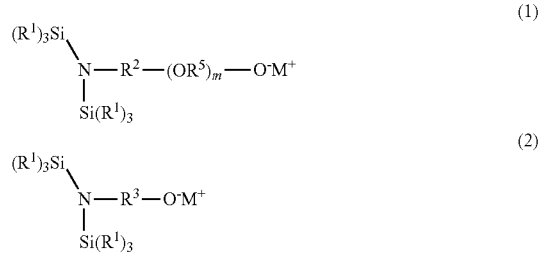

A method for producing a polyalkylene glycol derivative in the case in which the compounds represented by the general formulas (1) and/or (2) are used as a polymerization initiator in the present embodiment 2 is described as steps a') to c') as follows. As shown in the following, in the case in which the compound represented by the general formula (1) is used as a polymerization initiator, the polyalkylene glycol derivative to be obtained is the compound represented by the general formula (3), and in the case in which the compound represented by the general formula (2) is used as a polymerization initiator, the polyalkylene glycol derivative to be obtained is the compound represented by the general formula (4).

Step a') a step of reacting the polymerization initiator represented by the general formulas (1) and/or (2) with an alkylene oxide in a polymerization solvent to obtain compounds represented by the following general formulas (12) and/or (13), Step b') a step of reacting the compounds represented by the general formulas (12) and/or (13) with a compound represented by the following general formula (5) to obtain compounds represented by the following general formulas (14) and/or (15), and Step c') a step of deprotecting the compounds represented by the general formulas (14) and/or (15) to obtain compounds represented by the general formulas (3) and/or (4).

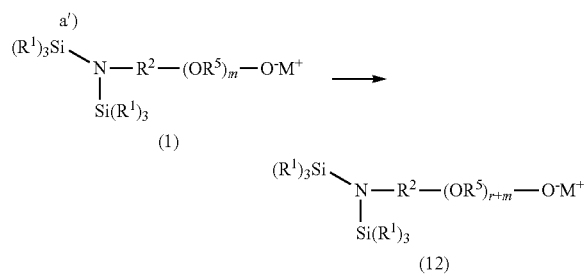

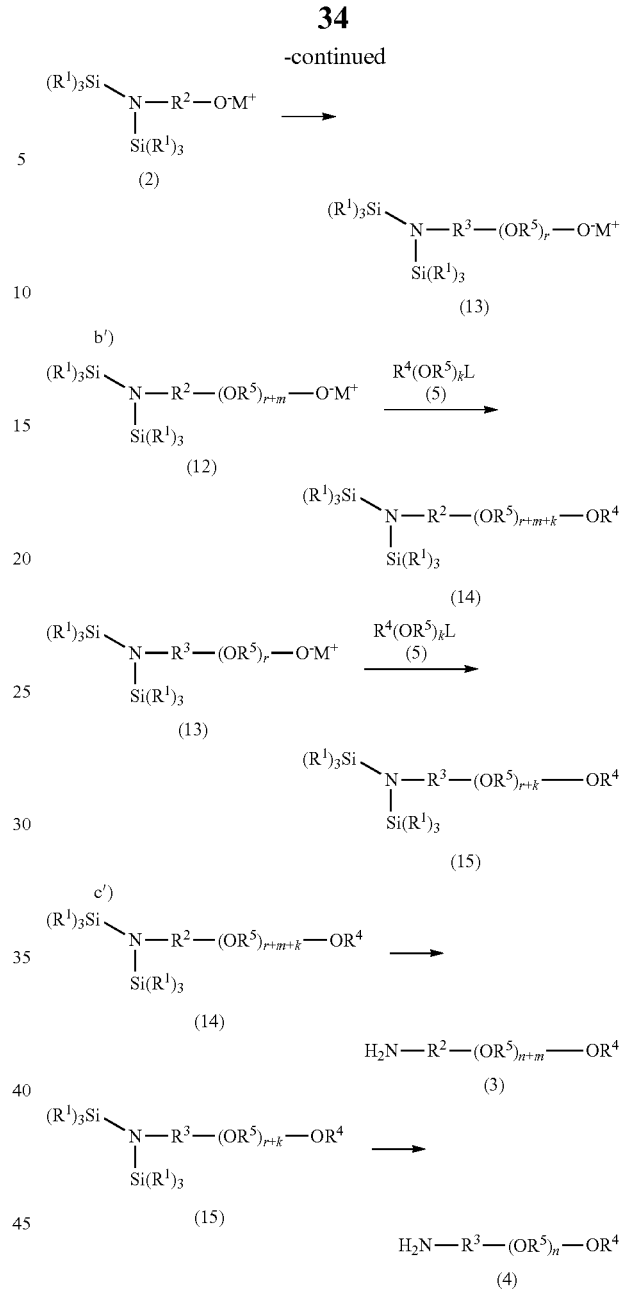

In the general formulas (1) to (2), and (12) to (15), $R^1$ each independently represent a linear monovalent hydrocarbon group having 1 to 6 carbon atoms, or a branched or cyclic monovalent hydrocarbon group having 3 to 6 carbon atoms. Alternatively, $R^1$ may bind to each other to form a 3 to 6 membered ring together with a silicon atom having bonds with $R^1$. Specific examples of $R^1$ include a methyl group, an ethyl group, an n-propyl group, an isopropyl group, an n-butyl group, an isobutyl group, a tert-butyl group, an n-pentyl group, an n-hexyl group, a cyclopropyl group, a cyclobutyl group, a cyclopentyl group, and a cyclohexyl group. Moreover, in the case in which $R^1$ bind to each other to form a ring together with a silicon atom, examples of $R^1$ include a group obtained by eliminating one hydrogen atom from the above-listed groups (in addition, as described above, $R^1$ in the present embodiment 2 is a discrete sign the definition of which is different from the definition of $R_A^{1a}$ and/or $R_A^{1b}$ in the embodiment 1, and is the same as $R^1$ in "(P-1) a protective group of a structure represented by Si(R$^1$)$_3$," described in the embodiment 1). R$^1$ is preferably the methyl group, the ethyl group, the n-propyl group, and the isopropyl group from the viewpoint of easiness of introducing two protective groups on nitrogen to easily synthesize the compounds represented by the general formulas (6) and/or (7) as will be described later.

In the general formulas (1), (3), (12), and (14), R$^2$ represents a linear divalent hydrocarbon group having 1 to 6 carbon atoms, or a branched or cyclic divalent hydrocarbon group having 3 to 6 carbon atoms. Specific examples of R$^2$ include a group obtained by eliminating one hydrogen atom from each of a methyl group, an ethyl group, an n-propyl group, an isopropyl group, an n-butyl group, an isobutyl group, a tert-butyl group, an n-pentyl group, an n-hexyl group, a cyclopropyl group, a cyclobutyl group, a cyclopentyl group, and a cyclohexyl group. R$^2$ in the present embodiment 2 corresponds to R$_A{}^2$ in the embodiment 1, and the definition of R$^2$ is the same as the definition of R$_A{}^2$ in the embodiment 1.

In the general formulas (2), (4), (13), and (15), R$^3$ represents a linear divalent hydrocarbon group having 4 to 6 carbon atoms. Specific examples of R$^3$ include a group obtained by eliminating one hydrogen atom from each of an n-butyl group, an n-pentyl group, and an n-hexyl group. R$^3$ in the present embodiment 2 is a discrete sign the definition of which is different from the definition of R$_A{}^3$ in the embodiment 1 as described above.

In the general formulas (3) to (5) and (14) to (15), R$^4$ represents a hydrogen atom, or a linear, branched, or cyclic hydrocarbon group that may be substituted, the hydrocarbon group having 1 to 12 carbon atoms, and the hydrocarbon group may contain a heteroatom. Specific examples of R$^4$ include a methyl group, an ethyl group, an n-propyl group, an isopropyl group, an n-butyl group, an isobutyl group, a tert-butyl group, a pentyl group, a cyclopentyl group, a hexyl group, a cyclohexyl group, an octyl group, a decyl group, a dodecyl group, a phenyl group, an o-tolyl group, an m-tolyl group, a p-tolyl group, a 2,3-xylyl group, a 2,4-xylyl group, a 2,5-xylyl group, a 2,6-xylyl group, a 3,4-xylyl group, a 3,5-xylyl group, a mesityl group, a vinyl group, and an allyl group. Examples of R$^4$ of a substituted structure include an acetalated formyl group, a cyano group, a formyl group, a carboxyl group, an amino group, an alkoxycarbonyl group having 1 to 6 carbon atoms, an acylamide group having 2 to 7 carbon atoms, tri(same or different alkyl having 1 to 6 carbon atoms)siloxy group, a siloxy group, a silylamino group, a maleimide group, a thiol group, a hydroxide group, a methacryloyloxy group, an acryloyloxy group, an active ester group, and an azi group. Specific examples of R$_A{}^4$ having a substituent include substituents represented by the following structures, although this is not limited thereto. The following formulas each represent an end portion of R$^4$ of a substituted structure, and the dotted lines in the formulas show that a hydrocarbon portion of R$^4$ can have variations as described above. Such substituents may further be protected by freely selected appropriate protective groups.

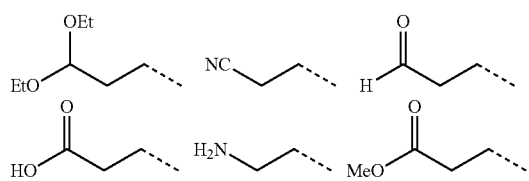

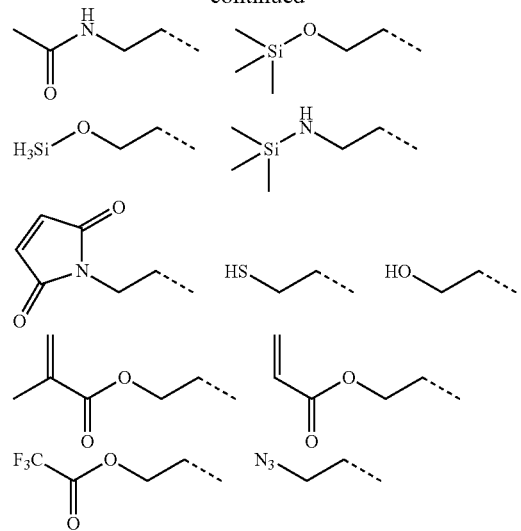

R$^4$ in the present embodiment 2 corresponds to R$_A{}^4$ in the embodiment 1, and the definition of R$^4$ is the same as the definition of R$_A{}^4$ in the embodiment 1.

In the general formulas (1), (3) to (5), and (12) to (15), R$^5$ represents an alkylene group having 2 to 8 carbon atoms. Among others, R$^5$ is preferably an alkylene group having 2 to 3 carbon atoms. That is to say, R$^5$ is preferably an ethylene group or a propylene group. In addition, the (OR$^5$) unit may be constituted from a single kind of oxyalkylene group, for example, from only an oxyethylene or oxypropylene group, or two or more kinds of oxyalkylene groups may be mixed together. In the case in which two or more kinds of oxyalkylene groups are mixed together, (OR$^5$) may be constituted from two or more kinds of different oxyalkylene groups by random polymerization or block polymerization. In addition, R$^5$ in the present embodiment 2 corresponds to R$_A{}^5$ in the embodiment 1, and the definition of R$^5$ is the same as the definition of R$_A{}^5$ in the embodiment 1.

In the general formulas (1) to (2), and (12) to (13), M represents an alkali metal, and specific examples of M are as described in the embodiment 1.

In the general formulas (1), (3), (12), and (14), m represents an integer of 1 to 3. Considering the boiling point of a compound when distilled, m is preferably an integer of 1 to 2.

Moreover, in the general formulas (1) to (4), and (12) to (15), r, k, n, and L are the same as r, k, n, and L described in the embodiment 1.

In selecting each of the compounds for use in each step in the production method of the present embodiment 2, desired R$^1$, R$^2$, R$^3$, R$^4$, R$^5$, m, r, k, n, and L in the general formulas (1), (2), (5), and (12) to (15) may be selected so that the compounds represented by the general formulas (3) and/or (4) as the desired final products may be obtained.

Moreover, in the present embodiment 2, [Pre-step 1'] and [Pre-step 2'] may be performed as an optional step prior to the steps a') to c'). The [Pre-step 1'] and [Pre-step 2'] include: a step ([Pre-step 1']) of producing compounds represented by the following general formulas (6) and/or (7) as a raw material (starting material) of the polymerization initiator; and a step ([Pre-step 2']) of producing compounds represented by the general formulas (1) and/or (2) as a polymerization initiator. As the pre-step, the [Pre-step 2'] may be performed subsequent to the [Pre-step 1'], or the [Pre-step 2'] may only be performed not through the [Pre-step 1'].

Moreover, in the present embodiment 2, a post-treatment step of purifying a produced target substance (compounds represented by the general formulas (3) and/or (4)) may be performed as an optional step after the steps a') to c').

The preferred embodiment 2 will be described below in the order of the [Pre-step 1'], the [Pre-step 2'], the steps a') to c'), and the post-treatment step along time series. The description will appropriately be omitted for passages the content of which is the same as those in the embodiment 1.

[Pre-Step 1']

The [Pre-step 1'] is a step of synthesizing the compound represented by the following general formulas (6) and/or (7) used as a precursor of the polymerization initiator.

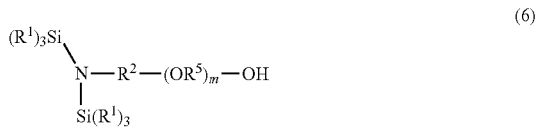

(In the general formulas (6) and (7), $R^1$, $R^2$, $R^3$, $R^5$, and m are the same as defined in the general formulas (1) and (2))

The [Pre-step 1'] may be performed in, for example, the following steps (1-1) to (1-2) and/or the following steps (2-1) to (2-2), although this is not limited thereto.

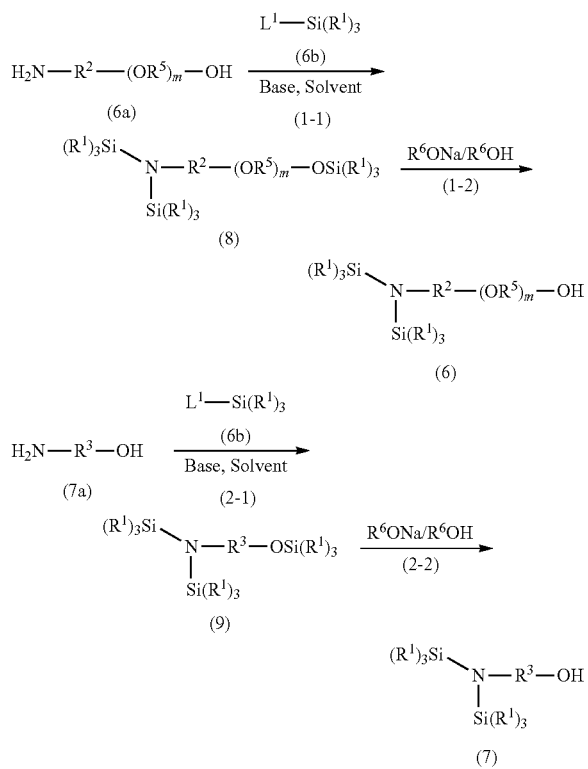

(In the general formulas (6a), (6b), (7a), (8), and (9), R', $R^2$, $R^3$, $R^5$, and m are the same as defined in the general formulas (1) and (2), $L^1$ represents a leaving group, specific examples thereof are as described in the embodiment 1, and $R^6$ represents a hydrocarbon group having 1 to 5 carbon atoms.)

Specific examples of $R^6$ include a methyl group, an ethyl group, an n-propyl group, an isopropyl group, an n-butyl group, an isobutyl group, a tert-butyl group, an n-pentyl group, a cyclopropyl group, a cyclobutyl group, and a cyclopentyl group, although this is not limited thereto.

A silicon-nitrogen bond is generally weaker than a silicon-oxygen bond, and therefore, in the deprotection reaction as represented by the formulas (1-2) and (2-2), the silicon-nitrogen bond is fundamentally cleaved in a preferential manner. However, in the case of the present reaction in the present embodiment 2, two bulky protective groups (trialkylsilyl groups) are present on the nitrogen atom, the silicon-oxygen bond can be cleaved in a preferential manner due to steric hindrance of the protective groups. In this way, after the amino group is protected by two bulky protective groups and the hydroxy group is also protected by a protective group of the same structure (that is, after all the three protective groups are introduced in the amino group and the hydroxy group), only the hydroxy group is deprotected in a preferential manner making use of bulk due to the presence of two protective groups on the amino group, so that an alcohol in which only the amino group is silylated can be synthesized. Such alcohol has been difficult to synthesize by conventional methods.

The steps (1-1) and/or (2-1) may be performed, for example, in the following manner. Reaction may be performed by adding a basic compound to the compounds represented by the general formulas (6a) and/or (7a) without a solvent, and subsequently dripping the compound represented by the general formula (6b) to mix, or, reaction may be performed by dissolving the compounds represented by the general formulas (6a) and/or (7a) in a proper solvent, then adding a basic compound, and then dripping the compound represented by the general formula (6b) to mix. The amount of the compound represented by the general formula (6b) used is, for example, 3 to 15 times, preferably 3 to 10 times, more preferably 3 to 5 times the number of moles of the compounds represented by the general formulas (6a) and/or (7a).

In the case in which a solvent is used in the steps (1-1) and/or (2-1), specific examples of the solvent include ethers such as THF and 1,4-dioxane, aromatic hydrocarbons such as benzene, toluene, and xylene, halogens such as methylene chloride, and N,N-dimethylformamide, N-methyl-2-pyrrolidone, acetonitrile, and acetone, although this is not limited thereto. The amount of the solvent used is, for example, 1 to 20 times, preferably 2 to 10 times, more preferably 2 to 5 times the mass of the compounds represented by the general formulas (6a) and/or (7a), although this is not particularly limited thereto.

As specific examples of the basic compound for use in the steps (1-1) and/or (2-1), hydroxides such as sodium hydroxide, potassium hydroxide, and tetramethylammonium hydroxide, carbonates such as sodium carbonate, potassium carbonate, and cesium carbonate, metal alkoxides such as sodium methoxide, sodium ethoxide, and potassium t-butoxide, metal hydrides such as sodium hydride, and potassium hydride, and primary, secondary, and tertiary aliphatic amines, conjugated amines, aromatic amines, heterocyclic amines, and ammonia water may be used although this is not limited thereto. The amount of the basic compound used is, for example, 3 to 15 times, preferably 3 to 10 times, more preferably 3 to 5 times the mass of the compounds represented by the general formulas (6a) and/or (7a).

The reaction temperature in the steps (1-1) and/or (2-1) may be within a range from the melting point to the boiling point of the solvent used, and is, for example, −60° C. to 150° C., preferably 0° C. to 80° C. The completion of the reaction in the steps (1-1) and/or (2-1) can be assumed when the compounds represented by the general formulas (6a) and/or (7a) analyzed by gas chromatography disappear or when the compounds represented by the general formulas (8) and/or (9) are obtained as main products.

Moreover, the steps (1-2) and/or (2-2) may be performed by, for example, treating, with a base, the compounds represented by the general formulas (8) and/or (9). Specifically, the steps (1-2) and/or (2-2) may be performed, for example, in the following manner After the compounds represented by the general formulas (8) and/or (9) are once purified and extracted, selective deprotection is performed by dissolving the compounds represented by the general formulas (8) and/or (9) in $R^6OH$ and adding a catalytic amount of $R^6ONa$. Produced $(R^1)_3SiOR^6$ is distilled away under reduced pressure together with $R^6OH$ to bias the equilibrium from the general formulas (8) and/or (9) toward the general formulas (6) and/or (7). $R^6OH$ is added again to further perform the reaction, and the operation of distilling produced $(R^1)_3SiOR^6$ away is repeated to make it possible to complete the reaction. The amount of $R^6OH$ used is, for example, 1 to 20 times, preferably 2 to 15 times, more preferably 3 to 10 times the mass of the compounds represented by the general formulas (8) and/or (9), although this is not particularly limited thereto. The amount of $R^6ONa$ used is, for example, 0.01 to 1 times, preferably 0.01 to 0.5 times, more preferably 0.01 to 0.1 times the number of moles of the compounds represented by the general formulas (8) and/or (9), although this is not particularly limited thereto.

The reaction temperature in the steps (1-2) and/or (2-2) is, for example, 0° C. to 100° C., preferably 30° C. to 80° C. The completion of the reaction in the steps (1-2) and/or (2-2) can be assumed when the compounds represented by the general formulas (8) and/or (9) analyzed by gas chromatography disappear. The compounds represented by the general formulas (6) and/or (7) are preferably purified by distillation to remove water. In that case, the water content ratio of the compounds represented by the general formulas (6) and/or (7) is, for example, 50 ppm or less, preferably 10 ppm or less, more preferably 5 ppm or less.

Examples of the other methods for producing the compounds represented by the general formulas (6) and/or (7) include such methods as the following steps (1-3) to (1-4), the following steps (1-5) to (1-6), and the following steps (2-3) to (2-4), although this is not limited thereto.

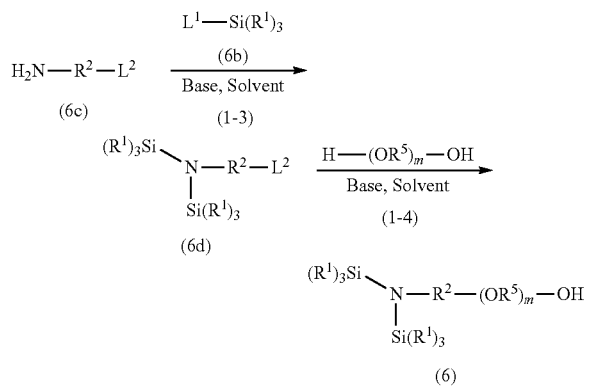

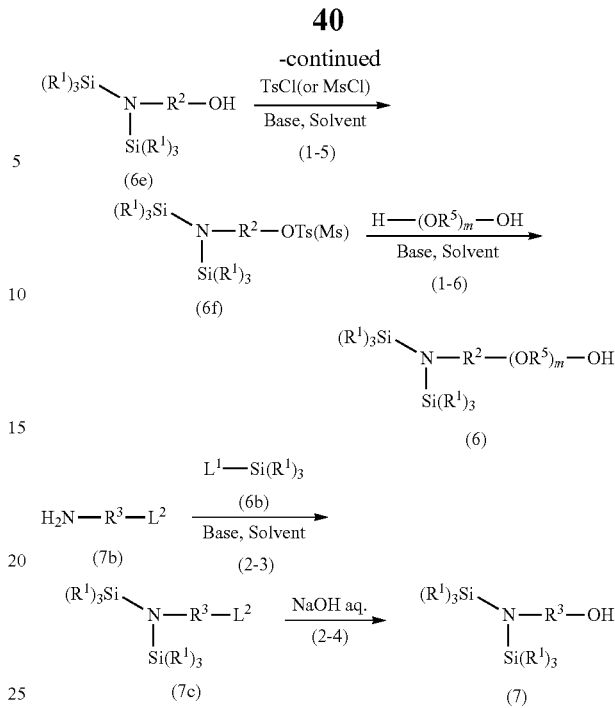

(In the general formulas (6b), (6c), (6d), (6e), (6f), (7b), and (7c), $R^1$, $R^2$, $R^3$, $R^5$, and m are the same as defined in the general formulas (1) and (2), $L^1$ and $L^2$ each represent a leaving group, the specific examples thereof are as described in the embodiment 1, TsCl is abbreviation of p-toluenesulfonyl, and MSCl is abbreviation of methanesulfonyl chloride.)

The steps (1-3) and (2-3) may be performed by the same method as in the step (i-2) described in the embodiment 1.

The steps (1-4) and (1-6) may be performed by the same method as in the step (i-3) described in the embodiment 1. In the case of the reaction represented by (1-4) or (1-6), as described in the step (i-3) in the embodiment 1, use of an excessive amount of a diol makes it possible to etherify an alcohol at one end.

The step (1-5) may be performed, for example, in the following manner Reaction may be performed, using, as a starting material, the compound represented by the general formula (6e) synthesized by the same method as in the step (i-1) described in the embodiment 1, by adding a basic compound to the compound represented by the general formula (6e) without a solvent, and then adding TsCl or MSCl to mix, or, reaction may be performed by dissolving the compound represented by the general formulas (6e) in a proper solvent, then adding a basic compound, and then adding TsCl or MsCl to the solution to mix. The amount of TsCl or MsCl used is, for example, 1 to 5 times, preferably 1 to 3 times, more preferably 1 to 2 times the number of moles of the compound represented by the general formula (6e).

In the case in which a solvent is used in the step (1-5), specific examples of the solvent include ethers such as THF and 1,4-dioxane, aromatic hydrocarbons such as benzene, toluene, and xylene, halogens such as methylene chloride, and N,N-dimethylformamide, N-methyl-2-pyrrolidone, and acetonitrile, although this is not limited thereto. The amount of the solvent used is, for example, 1 to 20 times, preferably 2 to 10 times, more preferably 2 to 5 times the mass of the compound represented by the general formula (6e), although this is not particularly limited thereto.

As specific examples of the basic compound for use in the step (1-5) include hydroxides such as sodium hydroxide, potassium hydroxide, and tetramethylammonium hydroxide, carbonates such as sodium carbonate, potassium carbonate, and cesium carbonate, metal alkoxides such as sodium methoxide, sodium ethoxide, and potassium t-butoxide, metal hydrides such as sodium hydride and potassium hydride, and primary, secondary, and tertiary aliphatic amines, conjugated amines, aromatic amines, heterocyclic amines, and ammonia water may be used, although this is not limited thereto. The amount of the basic compound used is, for example, 3 to 15 times, preferably 3 to 10 times, more preferably 3 to 5 times the mass of the compound represented by the general formula (6e).

The reaction temperature in the step (1-5) may be within a range from the melting point to the boiling point of the solvent used, and is, for example, −60° C. to 150° C., preferably 0° C. to 80° C. The completion of the reaction in the step (1-5) can be assumed when the compound represented by the general formula (6e) analyzed by gas chromatography disappears.

The step (2-4) may be performed, for example, in the following manner.

Reaction may be performed, using, as a starting material, the compound represented by the general formula (7c) synthesized in the step (2-3), by adding a sodium hydroxide aqueous solution without a solvent to mix, or, reaction may be performed by dissolving the compound represented by the general formula (7c) in a proper solvent, and then adding a sodium hydroxide aqueous solution to mix. The amount of sodium hydroxide used is, for example, 1 to 5 times, preferably 1 to 3 times, more preferably 1 to 2 times the number of moles of the compound represented by the general formula (7c).

In the case in which a solvent is used in the step (2-4), specific examples of the solvent include $H_2O$, ethers such as THF and 1,4-dioxane, aromatic hydrocarbons such as benzene, toluene, and xylene, halogens such as methylene chloride, and N,N-dimethylformamide, N-methyl-2-pyrrolidone, and acetonitrile, although this is not limited thereto. The amount of the solvent used is, for example, 1 to 20 times, preferably 2 to 10 times, more preferably 2 to 5 times the mass of the compound represented by the general formula (7c), although this is not particularly limited thereto.

The reaction temperature in the step (2-4) may be within a range from the melting point to the boiling point of the solvent used, and is, for example, −60° C. to 100° C., preferably −30° C. to 20° C. The completion of the reaction in the step (2-4) can be assumed when the compound represented by the general formula (7c) analyzed by gas chromatography disappears.

[Pre-Step 2']

The [Pre-step 2'] is a step of reacting the compounds represented by the general formulas (6) and/or (7) with an alkali metal or an alkali metal compound to obtain the compounds represented by the following general formulas (1) and/or (2).

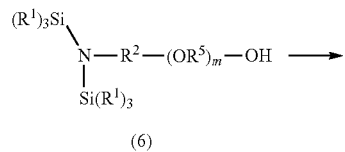

(6)

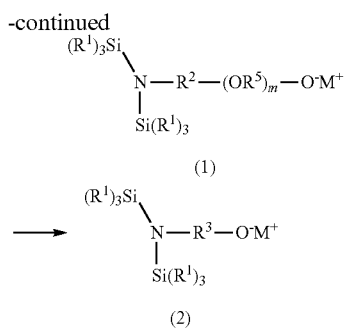

(1)

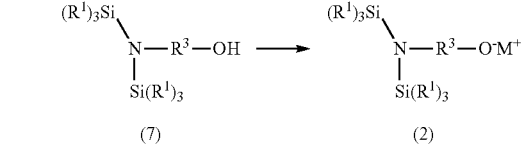

(7)  (2)

The reaction of the [Pre-step 2'] may be performed in the same manner as in the pre-step 2 in the embodiment 1. That is to say, the kind and amount of the alkali metal or alkali metal compound used, the kind and amount of the solvent used, the method for adding the compounds to the reaction system, and the reaction temperature may be appropriately selected within the range as described in the pre-step 2 in the embodiment 1. Moreover, as the solvent for use in the [Pre-step 2'], a solvent of the same kind as the polymerization solvent for use in polymerization is used, so that whether the polymerization initiator dissolves or not in the polymerization solvent can be confirmed in advance during the synthesis of the polymerization initiator. The confirmation method is the same as described in the pre-step 2 in the embodiment 1.

As described above, in the polymerization reaction, the water content in the reaction system containing the compounds represented by the general formulas (1) and/or (2) (polymerization initiator) is required to be reduced as low as possible in order to suppress the production of a diol polymer as a by-product. Regarding this, a compound represented by the general formula (6) with, for example, $R^1$=an ethyl group, $R^2$=$CH_2CH_2CH_2$, m=1, and a high boiling point of 120° C. (10 Pa) and a compound represented by the general formula (7) with $R^1$=an ethyl group, $R^3$=$CH_2CH_2CH_2CH_2CH_2CH_2$ and a high boiling point of 110° C. (10 Pa) have a sufficient difference in boiling point from water, so that separation of water can be achieved by drying under reduced pressure. Therefore, it is preferred that, prior to the addition of the alkali metal or the alkali metal compound in the [Pre-step 2'], the compounds represented by the general formulas (6) and/or (7) be sufficiently dried under reduced pressure and then distilled. The range of the water content ratio of the compounds represented by the general formulas (6) and/or (7) is the same as the range of the water content ratio of the compound described in the pre-step 2 in the embodiment 1 and represented by the general formula (i).

As described above, in order to increase the polymerization rate, a polymerization initiator having a small amount of a residual alcohol as an initiator raw material is preferably used. Specifically, it is preferred that the ratio of the amounts of substances between the polymerization initiator represented by the general formulas (1) and/or (2) and the alcohol that is an initiator raw material represented by the general formulas (6) and/or (7) after completion of the synthesis of the polymerization initiator in the [Pre-step 2'] be in the same range as the range of the ratio of the amounts of substances between the polymerization initiator represented by the general formula (I) and the alcohol that is an initiator raw material represented by the general formula (i) as described in the pre-step 2 in the embodiment 1. Moreover, it is possible to distill away the alcohol represented by the general formulas (6) and/or (7) under reduced pressure after the polymerization initiator is synthesized, and also in that case, it is preferred that the ratio of the amounts of substances between the polymerization initiator represented by the general formulas (1) and/or (2) and the alcohol represented by the general formulas (6) and/or (7) is in the same range as the range of the ratio of the amounts of substances between the polymerization initiator represented by the general formula (I) and the alcohol represented by the general formula (i) as described in the pre-step 2 in the embodiment 1.

[Step a')]

The step a') is a step of reacting the compounds represented by the general formulas (1) and/or (2) with an alkylene oxide in a polymerization solvent. The compound represented by the general formulas (1) and/or (2) are desirably reacted with the alkylene oxide after the compounds represented by the general formulas (1) and/or (2) are completely dissolved in the polymerization solvent. According to the step a'), the compounds represented by the following general formulas (12) and/or (13) can be obtained. As the polymerization initiator, only one of the compounds represented by the general formula (1) and the compounds represented by the general formula (2) may be used, or both may be used together.

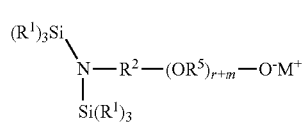

(12)

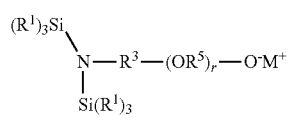

(13)

Since the silicon-oxygen bond is generally stronger than the silicon-nitrogen bond, there is a possibility that exchange reaction between the silicon-nitrogen bond and the silicon-oxygen bond progresses within a molecule during synthesis of a silyl-protected amino group-containing alkoxide in the case in which a five-membered ring or six-membered ring structure containing a silicon-oxygen bond can be formed. Therefore, when polymerization is tried using, for example, a compound represented by the following general formula (0a) as a polymerization initiator, polymerization progresses from the amino group side, not from the alkoxide side, and a target polyalkylene glycol derivative cannot be obtained. In contrast, in the polymerization initiator (for example, the following formulas (1a) and (2a)) represented by the general formulas (1) and/or (2) for use in the present embodiment 2, production of the five-membered or six-membered ring containing a silicon-oxygen bond is suppressed by extending the length of a chain that connects nitrogen and oxygen that constitutes O⁻M⁺ to 4 or more, so that a stable structure can be formed in a state of being an alkoxide. As a result thereof, polymerization progresses from the alkoxide side, and the target polyalkylene glycol derivative can be obtained.

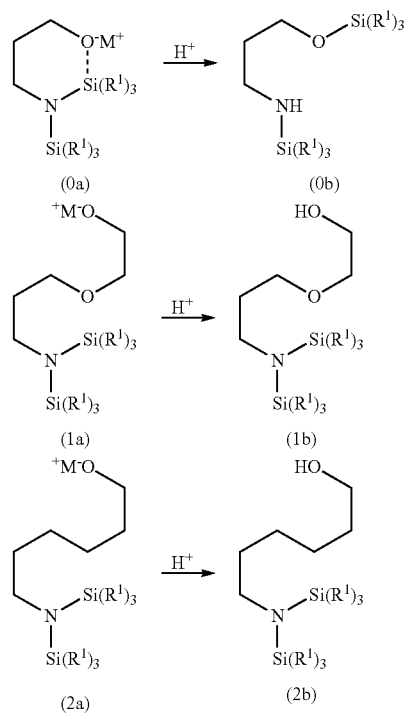

The silyl-protected amino group-containing alcohol derivatives represented by the general formulas (1) and/or (2) which are used as a polymerization initiator each have a structure similar to that of the polymerization solvent within each molecule, and therefore can dissolve in the polymerization solvent in the absence of an alcohol that is an initiator raw material. The polymerization initiator represented by the general formula (1) in particular has an alkylene oxide structure within the molecule to enhance the compatibility between the polymerization initiator and the polymerization solvent in the case in which the solvent is, for example, an ether-based solvent such as THF, and therefore, the polymerization initiator can dissolve in the polymerization solvent in the absence of the alcohol. Moreover, the polymerization initiator represented by the general formula (2) in particular has a hydrocarbon structure represented by R³ within the molecule to enhance the compatibility between the polymerization initiator and the polymerization solvent in the case in which the solvent is, for example, a hydrocarbon-based solvent such as toluene, and therefore, the polymerization initiator can dissolve in the polymerization solvent in the absence of the alcohol. As a result thereof, polymerization in a uniform system under mild conditions becomes possible, making it possible to produce a narrowly distributed polyalkylene glycol derivative.

The reaction in the step a') may be performed in the same manner as described in the step a) in the embodiment 1. That is to say, the kind and amount of the polymerization solvent used, the method for adding the alkylene oxide to the reaction system, and the reaction temperature may appropriately be selected within the range as described in the step a) in the above-described embodiment.

Among others, in the case in which the polymerization initiator represented by the general formula (1) is used, the polymerization initiator has an alkylene oxide structure within the molecule, and therefore, a cyclic ether compound having 4 to 10 carbon atoms, or a linear or branched ether compound, is preferably used as a polymerization solvent. Specific examples of the cyclic ether compound, and the linear or branched ether compound are as described respectively in the step a) in the embodiment 1. Moreover, in the case in which the polymerization initiator represented by the general formula (2) is used, the polymerization initiator has a hydrocarbon structure within the molecule, and therefore an aromatic hydrocarbon is preferably used as a polymerization solvent. Specific examples of the hydrocarbons are also as described in the step a) in the above-described embodiment.

[Step b')]

The step b') is a step of reacting the compounds obtained in the step a') and represented by the general formulas (12) and/or (13) with the compound represented by the following general formula (5). Through the step b'), the compounds represented by the general formulas (14) and (15) can be obtained.

$$R^4(OR^5)_k L \tag{5}$$

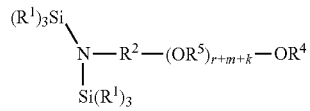
(14)

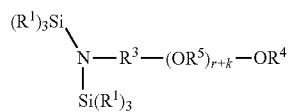
(15)

The reaction of the step b') may be performed in the same manner as in the step b) in the embodiment 1. That is to say, the method for adding the compound represented by the general formula (5) to the reaction system, the kind and amount of the solvent used, the kind and amount of the basic catalyst used, the kind and amount of alkaline adsorbent used, the reaction temperature, and crystallization, washing, and purification of the obtained compounds represented by the general formulas (14) and/or (15) may appropriately be selected within the range as described in the step b) in the above-described embodiment.

[Step c')]

In the step c'), the compounds obtained in the step b') and represented by the general formulas (14) and/or (15) are deprotected. The deprotection is preferably performed without using a heavy metal catalyst. More preferably, the compounds represented by the general formulas (14) and/or (15) are deprotected under an acidic condition. Specifically, the compounds represented by the general formulas (14) and/or (15) are reacted with water or an alcohol (R$^6$OH: wherein R$^6$ represents a hydrocarbon group having 1 to 5 carbon atoms) in the presence of an acid catalyst, so that the conversion to the compounds represented by the general formulas (3) and/or (4) may be performed. The reaction may be performed by reacting the compounds represented by the general formulas (14) and/or (15) with water or an alcohol in the presence of an acid catalyst without a solvent or in a proper solvent as needed. In the reaction, the yield rate can be improved by transferring the equilibrium to the product side, and therefore produced (R$^1$)$_3$SiOH or (R$^1$)$_3$SiOR$^6$ is preferably distilled away under heating or reduced pressure. The amount of water or the alcohol used is, for example, 2 to 4000 equivalents, preferably 10 to 3000 equivalents, more preferably 20 to 2000 equivalents, relative to the number of moles of the compounds represented by the general formulas (14) and/or (15), although this is not particularly limited thereto.

$$H_2N-R^2-(OR^5)_{n+m}-OR^4 \tag{3}$$

$$H_2N-R^3-(OR^5)_n-OR^4 \tag{4}$$

Specific examples of the acid catalyst used include carboxylic acids such as formic acid, acetic acid, propionic acid, succinic acid, citric acid, tartaric acid, fumaric acid, malic acid, and trifluoroacetic acid, inorganic acids such as hydrochloric acid, sulfuric acid, nitric acid, phosphoric acid, and perchloric acid, and sulfonic acids such as benzenesulfonic acid and p-toluenesulfonic acid, and solid acids such as AMBERLYST SERIES made by Organo Corporation, although this is not limited thereto. The amount of the acid catalyst used is, for example, 0.01 to 500 equivalents, preferably 0.1 to 300 equivalents, more preferably 0.1 to 150 equivalents, relative to the number of moles of the compounds represented by the general formulas (14) and/or (15). These acid compounds may be used alone, or in combinations of two or more. In that case, the mixing ratio is not particularly limited.

Crystallization, washing, and purification of the compounds obtained after deprotection and represented by the general formulas (3) and/or (4) may appropriately be selected and performed within the range as described in the step c) in the embodiment 1.

Since the amino group in the compounds represented by the general formulas (3) and/or (4) is obtained by deprotection in the step c'), by-products (compounds represented by the following (A) to (C-2)) that can be produced by the method described in, for example, Japanese Patent No. 3562000 are not produced, and finally narrowly distributed and high-purity polyalkylene glycol derivatives having an amino group at an end and represented by the general formulas (3) and/or (4) can be synthesized in the present invention. In contrast, in the case in which the method described in, for example, Japanese Patent No. 3562000 is used, a PEG derivative represented by the following general formula (A) cannot be prevented, as described above. Moreover, there is a possibility that secondary and tertiary amines represented by the following general formulas (B-1), (B-2), (C-1), and (C-2) are by-produced in the hydrogen reduction step. It is difficult to completely control these side reactions by the conventional methods as described above.

$$H-(OR^5)_n-OR^4 \tag{A}$$

$$HN+R^2-(OR^5)_{n+m}-OR^4)_2 \tag{B-1}$$

$$N+R^2-(OR^5)_{n+m}-OR^4)_3 \tag{B-2}$$

$$HN+R^3-(OR^5)_n OR^4)_2 \tag{C-1}$$

$$N+R^3-(OR^5)_n-OR^4)_3 \tag{C-2}$$

(In the general formulas (A), (B-1), (B-2), (C-1), and (C-2), R$^2$, R$^3$, R$^4$, R$^5$, m, and n are the same as defined in the general formulas (3) and (4).)

[Post-Treatment Step]

The post-treatment step of purifying the compounds represented by the general formulas (3) and/or (4) with a strong acid cation exchange resin may be performed after the step c'). The post-treatment step in this case may also be performed by the same operations as described in the post-treatment step in the embodiment 1.

In this way, the steps a') to c') are performed, (or the pre-steps 1' and 2' and/or the post-treatment step are further performed optionally before and/or after performing the steps a') to c')), so that the compounds (narrowly distributed and high-purity polyalkylene glycol derivatives having an amino group at an end) represented by the general formulas (3) and/or (4) can be produced.

That is to say, according to another aspect, the present invention relates to narrowly distributed and high-purity polyalkylene glycol derivatives having an amino group at an end, the polyalkylene glycol derivatives obtained by the above-described production method and represented by the general formulas (3) and/or (4).

Regarding properties of the compound represented by the general formulas (3) and/or (4) obtained after performing the steps a') to c') (or obtained by further performing the pre-steps 1' and 2' and/or the post-treatment step optionally before and/or after performing the steps a') to c')), namely the dispersity and weight average molecular weight, the amount of by-products (PEG derivative, and secondary and tertiary amines) mixed, the content of heavy metal impurities are the same as described with respect to the compound represented by the general formula (III) in the embodiment 1.

According to yet another aspect, the present invention relates to a metal salt of a protected amino group-containing alcohol compound represented by the general formula (I), the compound used as a polymerization initiator for use in the above-disclosed method for producing a polyalkylene glycol derivative having an amino group at an end. Among others, the metal salt is preferably a metal salt of a novel silyl-protected amino group-containing alcohol compound represented by the general formula (1) or (2). Further, the present invention also relates to a novel protected amino group-containing alcohol compound represented by the general formula (i), the compound used as a raw material (starting material) of the polymerization initiator. Among others, the alcohol compound is preferably a novel silyl-protected amino group-containing alcohol compound represented by the general formula (6) or (7). The definition, production method, and use method of these compounds are described in detail in the method for producing a polyalkylene glycol derivative in the embodiment 1 and the embodiment 2, and therefore the descriptions thereof are omitted.

EXAMPLES

The present invention is specifically illustrated with reference to the following Examples and Comparative Examples, though the present invention is not limited to the following Examples. In the notation of molecular weight in Examples, the weight average molecular weight (Mw) and the number average molecular weight (Mn) are values in terms of polyethylene glycol measured by GPC. Measurement by gel permeation chromatography (GPC) was performed under the following conditions:
Column: TSK gel Super AWM-H, Super AW-3000
Developing solvent: DMF (0.01 mol/L lithium bromide solution)
Column oven temperature: 60° C.
Sample concentration: 0.20 wt. %
Sample injection volume: 25
Flow rate: 0.3 ml/min

[Synthesis Example 1] Synthesis of Compound Represented by Formula (iA)

[Synthesis Example 1-1] Synthesis of Compound Represented by Formula (iA-1)

In a 50 ml three neck flask, 0.75 g of 2-(3-aminopropoxy)-ethanol, 2.35 g of triethylamine, and 2.92 g of toluene were charged, and then 5.98 g of triethylsilyl trifluoromethane-sulfonate (hereinafter, written as "TESOTf") was dripped under a nitrogen atmosphere. Stirring was then performed at 80° C. for 25 hours. The reaction liquid was transferred into a separatory funnel, the lower layer was separated, and the upper layer was distilled under reduced pressure, so that 2.71 g (yield rate 93.3%) of a silyl-protected compound (iA-1) was produced.

Silyl-protected compound (iA-1)
Colorless liquid
Boiling point 190° C./10 Pa
$^1$H-NMR (500 MHz, CDCL3): δ=0.63 (18H, q), 0.96 (27H, t), 1.69 (2H, m), 2.83 (2H, m), 3.40 (2H, t), 3.49 (2H, t), 3.76 (2H, t)

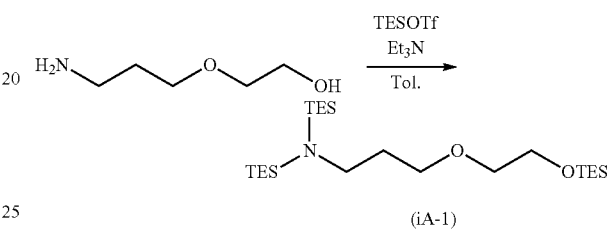

(iA-1)

In the formula, TES means a triethylsilyl group.

[Synthesis Example 1-2] Synthesis of Compound Represented by Formula (iA)

In a 10 ml round-bottom flask, 2.21 g of the silyl-protected compound (iA-1), 2.70 g of methanol, and 13 mg of sodium methoxide were charged, and stirring was performed at 60° C. for 18 hours. Triethylmethoxy silane was then distilled away under reduced pressure, 2.70 g of methanol was again placed into the flask, and stirring was performed at 60° C. The same operation was repeated, quenching was performed with sodium bicarbonate after completion of reaction, solvent substitution with toluene was performed, and a salt was then removed by filtration. Reduced pressure-distillation was then performed, so that 1.50 g (yield rate 90.0%) of a silyl-protected amino group-containing alcohol (iA) was produced. The measured water content ratio after distillation was 1 ppm or less.

Silyl-protected amino group-containing alcohol (iA)
Colorless liquid
Boiling point 118 to 122° C./10 Pa
$^1$H-NMR (500 MHz, CDCL3): δ=0.60 (12H, q), 0.93 (18H, t), 1.68 (2H, m), 1.96 (1H, bs), 2.82 (2H, m), 3.40 (2H, t), 3.50 (2H, m), 3.73 (2H, m)

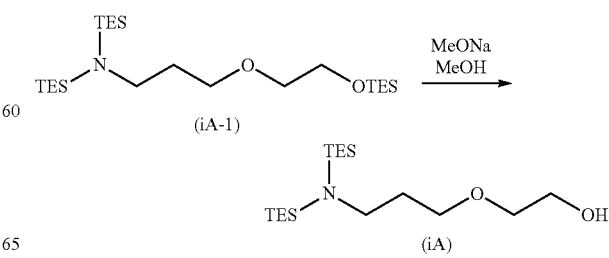

[Synthesis Example 2] Synthesis of Formula (iA) by Another Method

[Synthesis Example 2-1] Synthesis of Electrophile (iiA)

(2-1-1) Synthesis of Silyl Protector (iiA-1)

In a 300 ml three neck flask, 6.0 g of 3-amino-1-propanol, 28.74 g of triethylamine, and 18.0 g of toluene were charged, and then 75.0 g of TESOTf was dripped therein under a nitrogen atmosphere. Stirring was then performed at 80° C. for 25 hours. The reaction liquid was transferred into a separatory funnel, the lower layer was separated, and the upper layer was distilled under reduced pressure, so that 31.47 g (yield rate 93.3%) of a silyl protector (iiA-1) was produced.

Silyl Protector (iiA-1)
Colorless liquid
Boiling point 133 to 138° C./10 Pa
$^1$H-NMR (500 MHz, CDCL3): δ=0.60 (18H, q), 0.94 (27H, t), 1.62 (2H, m), 2.83 (2H, m), and 3.54 (2H, t)

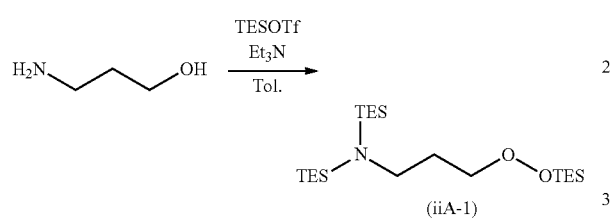

(2-1-2) Silyl-Protected Amino Group-Containing Alcohol (iiA-2)

In a 200 ml round-bottom flask, 30.98 g of silyl protector (iiA-1), 30.98 g of methanol, and 0.2 g of sodium methoxide were charged, and stirring was performed at 60° C. for 18 hours. Triethylmethoxy silane was then distilled under reduced pressure, 30.98 g of methanol was again placed into the flask, and stirring was performed at 60° C. The same operation was repeated, quenching was performed with sodium bicarbonate after completion of reaction, solvent substitution with toluene was performed, and a salt was then removed by filtration. Toluene was then distilled away under reduced pressure, so that 22.66 g of a silyl-protected amino group-containing alcohol (iiA-2) was produced (crude yield rate 96.4%). It was able to be confirmed from a $^1$H-NMR spectrum that this crude product had a sufficient purity as an intermediate, so that the compound (iiA-2) was directly used in the subsequent step.

Silyl-protected amino group-containing alcohol (iiA-2)
Colorless liquid
$^1$H-NMR (500 MHz, CDCL3): δ=0.60 (12H, q), 0.93 (18H, t), 1.67 (2H, m), 2.85 (2H, m), and 3.59 (2H, m)

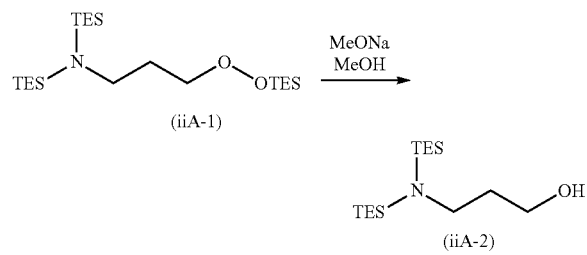

(2-1-3) Synthesis of Electrophile (iiA)

In a 50 ml three neck flask, 4.7 g of TsCl, 5 g of methylene chloride, and 5.0 g of triethylamine were charged, and a solution of 5.0 g of the silyl-protected amino group-containing alcohol (iiA-2) dissolved in 10.0 g of methylene, chloride was dripped therein while the flask was ice-cooled. The temperature was brought back to normal temperature, stirring was performed for 13 hours, quenching was then performed with water, and extraction was performed with toluene. The toluene solution was then concentrated, so that 7.6 g (crude yield rate 100%) of an electrophile (iiA) was produced. It was confirmed from a $^1$H-NMR spectrum that the crude product had a sufficient purity as an intermediate, and thus (iiA) was used directly for the subsequent step.

Electrophile (iiA)
Brown liquid
$^1$H-NMR (500 MHz, CDCL$_3$): δ=0.54 (12H, q), 0.89 (18H, t), 1.68 (2H, m), 2.45 (3H, s), 2.71 (2H, m), and 3.98 (2H, t)

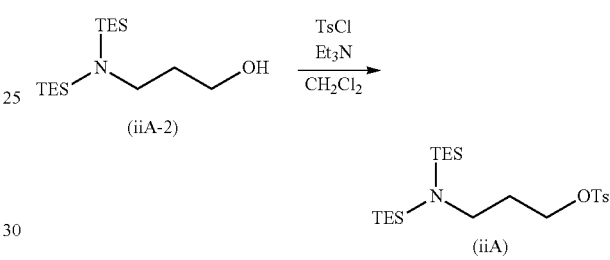

[Synthesis Example 2-2] Synthesis of Electrophile (iiB)

In a 200 ml three neck flask, 15.93 g of 3-bromopropylamine hydrobromate, 27.26 g of triethylamine, and 47.79 g of toluene were charged, and 50.00 g of TESOTf was then dripped therein under a nitrogen atmosphere. Stirring was then performed at 80° C. for 63 hours. The reaction solution was transferred to a separatory flask, the lower layer was separated, and the upper layer was distilled under reduced pressure, so that 8.00 g of an electrophile (iiB) was produced (yield rate 30.0%).

Electrophile (iiB)
Colorless liquid
Boling point 108° C./30 Pa
$^1$H-NMR (500 MHz, CDCL$_3$): δ=0.61 (12H, q), 0.94 (18H, t), 1.92 (2H, m), 2.90 (2H, m), and 3.31 (2H, t)

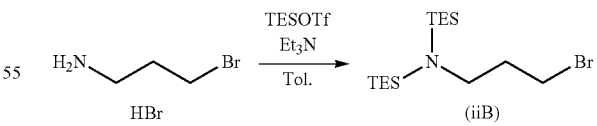

[Synthesis Example 2-3] Synthesis of Compound Represented by Formula (iA) with Electrophile (iiA)

In a 100 ml three neck flask, 6.78 g of ethylene glycol, 10 g of N-methylpyrrolidone, and 1.35 g of potassium tert-butoxide were charged, stirring was performed for 30 minutes, and then a solution of 5.0 g of an electrophile (iiA)

dissolved in 15 g of N-methylpyrrolidone was dripped at normal temperature. After the temperature was raised to 60° C. and stirring was performed for 5 hours, the reaction was stopped with 0.18 g of sodium bicarbonate. Subsequently, solvent substitution with diphenyl ether was performed, and a precipitated salt was then removed by filtration. Reduced pressure-distillation was then performed, so that 3.16 g (yield rate 65.7%) of a silyl-protected amino group-containing alcohol (iA) was produced. The measured water content ratio after distillation was 1 ppm or less (Measurement of the water content ratio was performed by a Karl Fisher moisture meter, and the same applies hereinafter).

Silyl-protected amino group-containing alcohol (iA)
Colorless liquid
Boiling point: same as the result obtained in the [Synthesis Example 1-2].
$^1$H-NMR (500 MHz, CDCL3): same as the result obtained in the [Synthesis Example 1-2].

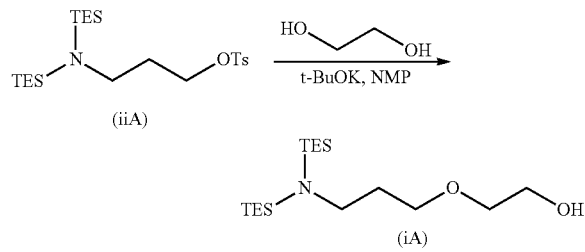

In the formula, Ts means a para-toluenesulfonyl group, t-BuOK means tert-butoxide, and NMP means N-methylpyrrolidone.

[Synthesis Example 2-4] Synthesis of Compound Represented by Formula (iA) with Electrophile (iiB)

In a 200 ml three neck flask, 2.98 g of ethylene glycol, 5.0 g of N-methylpyrrolidone, and 0.54 g of potassium tert-butoxide were charged, stirring was performed for 30 minutes, and then a solution of 2.00 g of an electrophile (iiB) dissolved in 10.0 g of N-methylpyrrolidone was dripped at normal temperature. After the temperature was raised to 60° C. and stirring was performed for 5 hours, the reaction was stopped with 0.08 g of sodium bicarbonate. Subsequently, solvent substitution with diphenyl ether was performed, and a precipitated salt was then removed by filtration. Reduced pressure-distillation was then performed, so that 1.07 g (yield rate 64.0%) of a silyl-protected amino group-containing alcohol (iA) was produced. The measured water content ratio after distillation was 1 ppm or less.

Silyl-protected amino group-containing alcohol (iA)
Colorless liquid
Boiling point: same as the result obtained in the [Synthesis Example 1-2].
$^1$H-NMR (500 MHz, CDCL3): same as the result obtained in the [Synthesis Example 1-2].

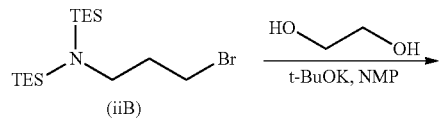

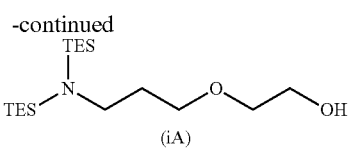

[Synthesis Example 3] Synthesis of Compound Represented by Formula (iB)

[Synthesis Example 3-1] Synthesis of Compound Represented by Formula (iB-1)

In a 200 ml three neck flask, 5.00 g of 6-amino-1-hexanol, 15.68 g of triethylamine, and 15.00 g of toluene were charged, and then 40.91 g of TESOTf was dripped under nitrogen atmosphere. Stirring was then performed at 80° C. for 25 hours. The reaction liquid was transferred into a reparatory funnel, the lower layer was separated, and the upper layer was distilled under reduced pressure, so that 18.39 g (yield rate 93.0%) of a silyl-protected compound (iB-1) was produced.

Silyl-protected compound (iB-1)
Colorless liquid
Boiling point 180° C./10 Pa
$^1$H-NMR (500 MHz, CDCL3): δ=0.63 (18H, q), 0.96 (27H, t), 1.69 (8H, m), 2.83 (2H, m), 3.40 (2H, t)

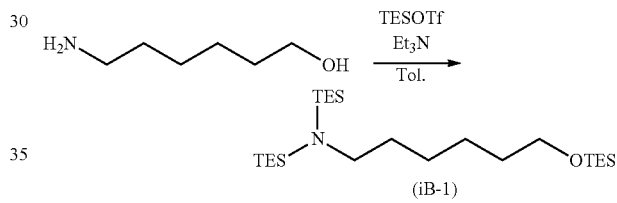

[Synthesis Example 3-2] Synthesis of Compound Represented by Formula (iB)

In a 50 ml one neck flask, 5.00 g of the silyl-protected compound (iB-1), 5.00 g of methanol, and 29 mg of sodium methoxide were charged, and stirring was performed at 60° C. for 18 hours. Triethylmethoxy silane was then distilled away under reduced pressure, 5.00 g of methanol was again placed into the flask, and stirring was performed at 60° C. The same operation was repeated, then quenching was performed with sodium bicarbonate after completion of reaction, solvent substitution with toluene was performed, and then a salt was removed by filtration. Reduced pressure-distillation was then performed, so that 3.35 g of a silyl-protected amino group-containing alcohol (iB) was produced (yield rate 89.0%). The measured water content ratio after distillation was 1 ppm or less.

Silyl-protected amino group-containing alcohol (iB)
Colorless liquid
Boiling point 118 to 112° C./10 Pa
[NMR4]

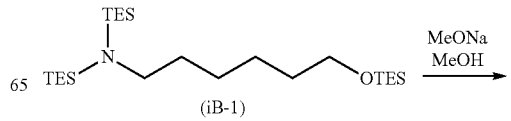

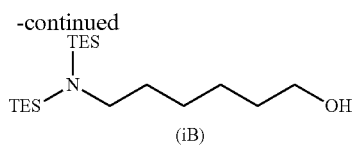

(iB)

[Synthesis Example 4] Synthesis of Compound Represented by Formula (IA)

[Synthesis Example 4-1] Synthesis of Compound Represented by Formula (IA)

In a glove box under a nitrogen atmosphere, potassium hydride (in a mineral oil form, made by Kanto Chemical Co., Ltd.) was fed into a 50 mL three neck flask, and after the mineral oil was washed with hexane to be separated, vacuum drying was performed for about two hours to obtain 0.50 g (12.5 mmol) of potassium hydride. Into the flask, 7.71 g of distilled THF was added with a syringe, and 4.44 g (12.8 mmol) of the compound represented by the general formula (iA) was dripped at normal temperature. Stirring was performed at normal temperature for 1 hour and then at 50° C. for 2 hours, so that 12.40 g (1.02 mmol/g) of a THF solution of the compound represented by the general formula (IA) was produced. Precipitation of a salt and cloudiness were not observed at that time ((IA) mass/THF solution mass=39.8 wt. %). The ratio of the amounts of substances between the polymerization initiator (IA) synthesized by the above-described reaction and the alcohol (iA) that is an initiator raw material is 98:2 (mol %). A reaction scheme is shown in the following.

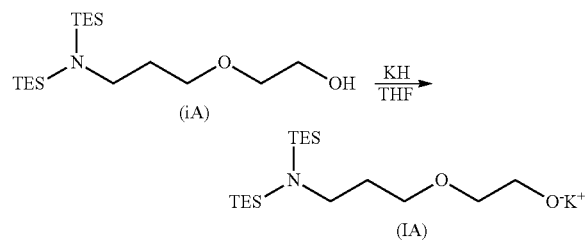

[Synthesis Example 4-2] Synthesis of Compound Represented by Formula (IA) by Another Method In a glove box under a nitrogen atmosphere, 2.02 g of naphthalene and 0.68 g of potassium were weighed and fed into a 100 mL three neck flask, and vacuum drying was performed for 1 hour. The flask was then brought back to under a nitrogen atmosphere, 19.65 g of distilled THF was added into the flask with a syringe. Stirring was performed for 1 hour to prepare a THF solution of potassium naphthalene (0.71 mmol/g). On the other hand, 1.96 g (5.64 mmol) of the compound represented by the formula (iA) was weighed with a syringe and fed into a 50 ml three neck flask under a nitrogen atmosphere. 7.85 g of the THF solution of potassium naphthalene prepared above was dripped therein at normal temperature. Maturation was performed for 1 hour, so that 9.77 g (0.58 mmol/g) of a THF solution of the polymerization initiator (IA) was produced. Precipitation of a salt and cloudiness were not observed at that time ((IA) mass/THF solution mass=22.3 wt. %). The ratio of the amounts of substances between the polymerization initiator (IA) synthesized by the above-described reaction and the alcohol (iA) that is an initiator raw material is 98:2 (mol %). A reaction scheme is shown in the following.

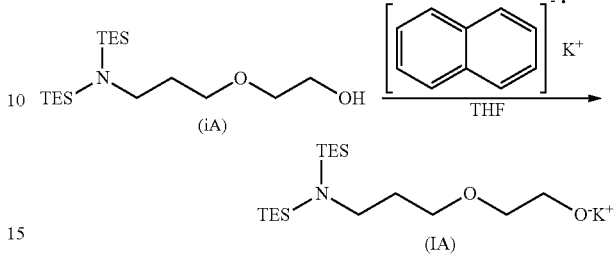

[Synthesis Example 5] Synthesis of Compound Represented by Formula (I-1A)

A stirring bar was placed in a 500 mL four neck flask connected to a thermometer, a dripping funnel, and a Dimroth condenser. After the degree of vacuum in the device was held at 10 Pa or less, the internal part of the device was heated with an oil bath and a heat gun, so that the water content in the system was removed. Subsequently, 1.69 g of the THF solution of the compound represented by the formula (IA), the THF solution prepared in the [Synthesis Example 4-1] and 140 g of distilled THF were added into the 2 L four neck flask under nitrogen stream. Into the dripping funnel, 20 g of ethylene oxide and 40 g of distilled THF were injected, to be dripped into the 500 mL four neck flask slowly. After confirming stabilization of the temperature in the 500 mL four neck flask, maturation was performed at 45 to 50° C. for 8 hours. A reaction scheme is shown in the following.

After completion of the reaction, the oil bath was detached and the reaction system was cooled to room temperature. A small amount of the produced reaction liquid was sampled, and the reaction was stopped with acetic acid for measurement by GPC. The following results were obtained: Mw=8,000 and Mw/Mn=1.04.

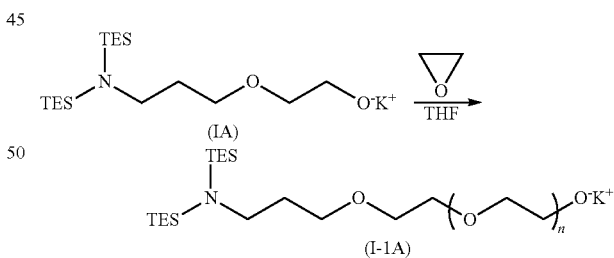

[Synthesis Example 6] Synthesis of Compound Represented by Formula (IIA)

[Synthesis Example 6-1] Synthesis of Compound Represented by Formula (IIA)

In a reaction liquid of the compound represented by the formula (I-1A), 2.41 g of 2-bromoethylmethyl ether and 10.5 mL (1 mol/L) of a THF solution of potassium tert-butoxide were added, and stirring was performed for 5 hours under refluxing. After a salt in the reaction liquid was removed by filtration, the reaction liquid was concentrated to 25 wt. %, and the concentrated liquid was transferred into a dripping funnel. In a 500 mL beaker with a stirring bar therein, 201 g of hexane was placed, and after dripping of the concentrated liquid thereto for 10 minutes, maturation was performed for 20 minutes. The produced white powder was filtered and then returned to the original beaker, to be washed with 99 g of hexane for 20 minutes, and the same washing operation was further performed once. A reaction scheme is shown in the following.

The produced white powder was vacuum-dried to obtain 18.6 g of a polymer (IIA). The following GPC measurement results were obtained: Mw=8,000 and Mw/Mn=1.05.

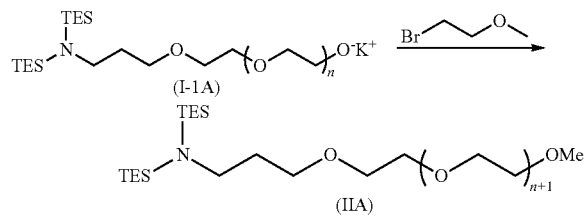

[Synthesis Example 6-2] Synthesis of Compound Represented by Formula (IIA) by Another Method In the reaction liquid of the compound represented by the formula (I-1A), 2.05 g of 2-methoxyethyl-p-toluenesulfonate and 0.50 g of potassium tert-butoxide were added, and stirring was performed at 40° C. for 5 hours. After a salt in the reaction liquid was removed by filtration, the reaction liquid was concentrated to 25 wt. %, and the concentrated liquid was transferred to a dripping funnel. In a 500 mL beaker with a stirring bar therein, 200 g of hexane was placed, and after dripping of the concentrated liquid thereto for 10 minutes, maturation was performed for 10 minutes. The produced white powder was filtered and then returned to the original beaker, to be washed with 100 g of hexane for 10 minutes, and the same washing operation was further performed once. A reaction scheme is shown in the following.

The produced white powder was vacuum-dried to obtain 18.6 g of the polymer (IIA). The following GPC measurement results were obtained: Mw=8,000 and Mw/Mn=1.05.

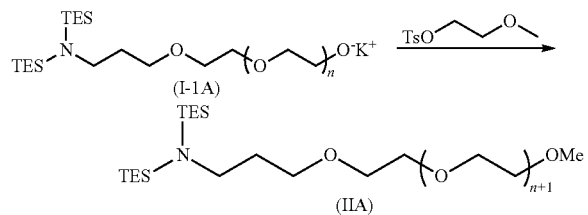

[Synthesis Example 6-3] Synthesis of Compound Represented by Formula (IIA) by Yet Another Method A 2 L high pressure reaction vessel was dried by nitrogen purge, and 8.29 g (1.02 mmol/g, 8.46 mmol) of a THF solution of the polymerization initiator (IA) synthesized by the method of the above-described [Synthesis Example 4-1] and 885 g of distilled THF were added thereto under a nitrogen atmosphere. After the temperature in the vessel was raised to 45° C., 100 g of ethylene oxide was continuously charged into the reaction vessel, and the pressure in the system was then adjusted to 0.15 MPa by nitrogen pressurization. Stirring was performed at 45° C. to gradually lower the pressure of the system, and after 6 hours, the pressure of the system became stable at 0.11 MPa where the reaction was determined to be completed. After the reaction system was cooled to 40° C., 9.75 g of 2-methoxyethyl-p-toluenesulfonate as an electrophile was dissolved in 97.5 g of THF, and the resultant mixture was charged into the system, and, further, 21 ml of a THF solution of potassium tert-butoxide (1 mol/L) was diluted with 21 g of THF, and the resultant solution was charged into the system. Subsequently, with the temperature being held at 40° C., maturation was performed for 5 hours. A precipitated salt was separated by filtration, 17 g of an adsorption material KW-2000 was added to the filtrate, stirring was performed for 2 hours, and the adsorption material was then removed by filtration. The reaction solution was concentrated to 400 g. 750 g of hexane and 750 g of ethyl acetate were then placed in a 3 L beaker with a stirring bar therein, and after dripping the produced reaction solution, maturation was performed for 10 minutes. The produced white powder was filtered and then returned to the original beaker, to be washed with 375 g of hexane and 375 g of ethyl acetate for 10 minutes, and after the same washing was repeated once again, the produced white powder was vacuum-dried to obtain 96 g of the polymer (IIA). The following GPC measurement results were obtained: Mw=11,400 and Mw/Mn=1.03. A reaction scheme is shown in the following.

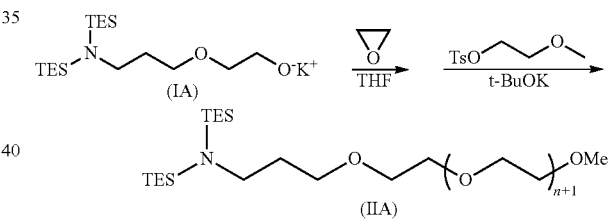

It is revealed that the polymerization with ethylene oxide stoichiometrically progresses in the Synthesis Example 6-3 as shown in Table 1 below.

TABLE 1

|  | Theoretical Mw | Mw | Mw/Mn | Yield rate (%) |
|---|---|---|---|---|
| Synthesis Example 6-3 | 12,000 | 11,400 | 1.03 | 95.5 |

[Synthesis Example 7] Synthesis of Compound Represented by Formula (IIIA-a)

[Synthesis Example 7-1] Synthesis of Compound Represented by Formula (IIIA-a)

Into a 50 ml three neck flask, 1.0 g of the compound produced in the [Synthesis Example 6-1] and represented by the formula (IIA), 9.0 g of THF and 0.4 ml of 1N HCl aq. were fed, and stirring was performed at 40° C. for 4 hours. The reaction was then stopped with 0.2 ml of 25 wt. % NaOH aqueous solution. After the reaction solution was concentrated to distill away water, the concentration of the polymer solution was adjusted by adding 5.7 g of THF, and a precipitated salt was filtered. In a 100 mL beaker with a stirring bar therein, 10 g of hexane was placed, and after dripping the produced reaction solution, maturation was performed for 10 minutes. The produced white powder was filtered and then returned to the original beaker, to be washed with 5 g of hexane for 10 minutes, and the same washing operation was further performed once.

The produced white powder was vacuum-dried to obtain 0.7 g of a compound represented by the formula (IIIA-a). The following GPC measurement results were obtained: Mw=7,900 and Mw/Mn=1.05. A reaction scheme is shown in the following.

Deprotection may subsequently be performed by adding hydrochloric acid without purifying the compound represented by the formula (IIA) after the reaction, and in that case, the process can be further simplified.

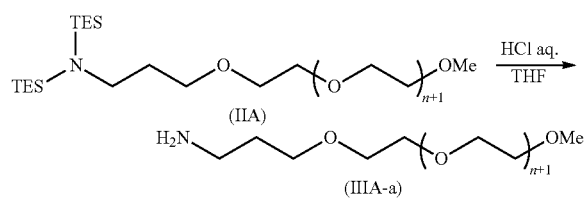

[Synthesis Example 7-2] Synthesis of Compound Represented by Formula (IIIA-a) by Another Method Into a 1 L three neck flask, 100 g of the polymer (IIA) produced in the [Synthesis Example 6-3], 400 g of MeOH, and 5.00 g of acetic acid were fed, and stirring was performed at 35° C. for 3 hours. The reaction was then stopped with 24.12 g of a 28% solution of sodium methylate in methanol. The reaction solution was concentrated, and solvent substitution with toluene was performed, so that 450 g of a polymer solution was prepared, and a precipitated salt was filtered. To the produced polymer solution, 100 g of the adsorption material KW-2000 was added, and treatment was performed at 35° C. for 1 hour to remove the trace amount of the salt. In a 3 L beaker with a stirring bar therein, 1000 g of hexane and 500 g of ethyl acetate were placed, and after dripping the produced reaction solution, maturation was performed for 10 minutes. The produced white powder was filtered and then returned to the original beaker, to be washed with 600 g of hexane and 300 g of ethyl acetate for 10 minutes, and the same washing operation was further performed once.

The produced white powder was vacuum-dried to obtain 90 g of a polymer (IIIA-a). The following GPC measurement results were obtained: Mw=11,000 and Mw/Mn=1.03. A reaction scheme is shown in the following.

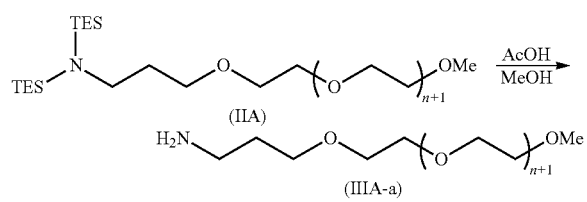

[Synthesis Example 8] Synthesis of Compound Represented by Formula (IIIB-a)

A compound represented by the formula (IIIB-a) was produced by the same operations as in [Synthesis Examples 4 to 7], except that the compound represented by the formula (iA) was changed to the compound represented by the formula (iB). That is to say, the polymerization initiator (IB) was synthesized using the compound represented by the formula (iB) by the same operations as in the [Synthesis Example 4-1], and the compound represented by the formula (IIIB-a) was produced with the polymerization initiator by the same operations as in the [Synthesis Examples 5 to 7]. In addition, the same operations as in the [Synthesis Examples 6-1 and 7-1] were performed in the [Synthesis Examples 6 and 7] respectively. The following GPC measurement results were obtained for the compound represented by the formula (IIIB-a): Mw=7,900 and Mw/Mn=1.05. A reaction scheme is shown in the following.

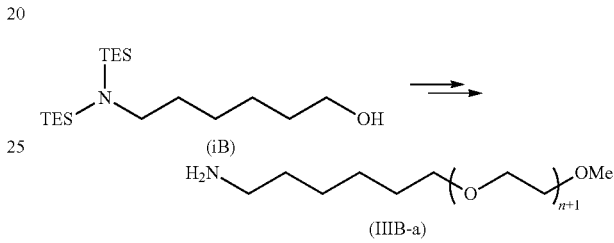

[Synthesis Example 9] Synthesis of Compounds Represented by Formulas (IIIA-b) to (IIIA-f)

Polymers (IIIA-b) to (IIIA-f) were synthesized by approximately the same operations as in the [Synthesis Examples 4 to 7], except that the ratio between the compound represented by the formula (iA) and ethylene oxide was changed. In addition, the same operations as in the [Synthesis Examples 4-1, 6-1, and 7-1] were performed in the [Synthesis Examples 4, 6, and 7] respectively. The analysis results are shown in Table 2.

TABLE 2

| Formula | Ethylene oxide | | |
| --- | --- | --- | --- |
| (iA) (mmol) | (g) | Mw | Mw/Mn |
| IIIA-a  1.72 | 20 | 7,900 | 1.05 |
| IIIA-b  1.72 | 22 | 8,600 | 1.05 |
| IIIA-c  1.72 | 25 | 9,800 | 1.05 |
| IIIA-d  1.72 | 30 | 12,000 | 1.04 |
| IIIA-e  1.72 | 38 | 15,200 | 1.04 |
| IIIA-f  1.72 | 50 | 19,800 | 1.05 |

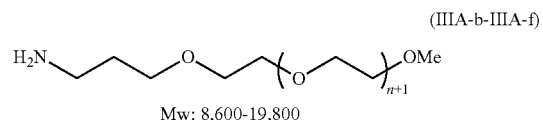

Mw: 8,600-19,800

[Synthesis Example 10] Synthesis of Compounds Represented by Formulas (IIIB-b) to (IIIB-f)

Polymers (IIIB-b) to (IIIB-f) were synthesized by approximately the same operations as in the [Synthesis Example 8], except that the ratio between the compound represented by the formula (iB) and ethylene oxide was changed. The analysis results are shown in Table 3.

TABLE 3

|  | Formula (iB) (mmol) | Ethylene oxide (g) | Mw | Mw/Mn |
|---|---|---|---|---|
| IIIB-a | 1.72 | 20 | 7,900 | 1.05 |
| IIIB-b | 1.72 | 22 | 8,600 | 1.05 |
| IIIB-c | 1.72 | 25 | 9,900 | 1.05 |
| IIIB-d | 1.72 | 30 | 12,200 | 1.04 |
| IIIB-e | 1.72 | 38 | 15,300 | 1.04 |
| IIIB-f | 1.72 | 50 | 19,700 | 1.05 |

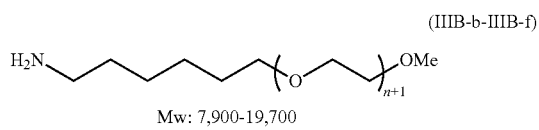

(IIIB-b-IIIB-f)

Mw: 7,900-19,700

[Synthesis Example 11] Synthesis of compounds represented by formulas (IIIA-g) to (IIIA-l), and (IIIB-g) to (IIIB-l)

Compounds represented by the formulas (IIIA-g) to (IIIA-l) were synthesized by approximately the same operations as in the [Synthesis Examples 4 to 7], and compounds represented by the formulas (IIIB-g) to (IIIB-l) were synthesized by approximately the same operations as in the [Synthesis Example 8], except that 2-bromoethylmethyl ether as the substrate in the [Synthesis Example 6-1] was changed to 2-bromoethyl (substituted) alkyl ethers having an alkyl group ($R^4$) (with a substituent) at an end, the ethers shown in the table below. The same operations as in the Synthesis Examples 4-1, 6-1, and 7-1 were performed in the Synthesis Examples 4, 6, and 7 respectively. The analysis results are shown in Tables 4 and 5.

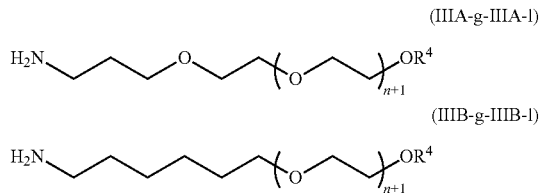

(IIIA-g-IIIA-l)

(IIIB-g-IIIB-l)

TABLE 4

|  | $R^4$ | Mw | Mw/Mn |
|---|---|---|---|
| IIIA-g | Ethyl group | 8,000 | 1.05 |
| IIIA-h | n-Propyl group | 8,100 | 1.06 |
| IIIA-i | Isopropyl group | 8,200 | 1.04 |
| IIIA-j | n-Butyl group | 8,400 | 1.05 |
| IIIA-k | Cyanoethyl group | 8,400 | 1.05 |
| IIIA-l | Methacryloyloxyethyl group | 8,500 | 1.05 |

TABLE 5

|  | $R^4$ | Mw | Mw/Mn |
|---|---|---|---|
| IIIB-g | Ethyl group | 7,900 | 1.05 |
| IIIB-h | n-Propyl group | 8,000 | 1.05 |
| IIIB-i | Isopropyl group | 8,100 | 1.04 |
| IIIB-j | n-Butyl group | 8,300 | 1.05 |
| IIIB-k | Cyanoethyl group | 8,300 | 1.05 |
| IIIB-l | Methacryloyloxyethyl group | 8,400 | 1.05 |

[Synthesis Example 12] Purification of the Compound Represented by the Formula (IIIA-a)

The inside of a cartridge filled with 50 g of a cation exchange resin DIAION PK-208 (made by Mitsubishi Chemical Corporation) was washed with 300 g of 1N hydrochloric acid, and then washed 3 times with 300 g of ion-exchanged water, and subsequently once with 300 g of methanol. Into a 500 mL two neck flask, a 5 wt. % solution of the polymer (IIIA-a) in methanol (polymer content; 10 g) was injected, and transferred into the cartridge with a pump. The methanol solution discharged from the liquid outlet of the cartridge was added into the original 500 mL round-bottom flask. The operation was continuously performed for 2 hours, so that the polymer (IIIA-a) was adsorbed to the cation exchange resin. Subsequently the resin in the cartridge was washed with 300 g of methanol once, and then the polymer (IIIA-a-2) was eluted from the cation exchange resin with 50 g of 7N ammonia solution (methanol solution made by Kanto Chemical Co., Ltd.). The purified polymer after the process of elution from the cation exchange resin is denoted as ("IIIA-a-2").

On the other hand, even when the compound represented by the formula (IIa) is used in place of the compound represented by the formula (IIIA-a), deprotection progresses in the methanol solution in the presence of the cation exchange resin catalyst, and therefore both deprotection and purification can be performed in parallel, and the process was able to be further simplified.

The produced eluent was transferred into a 500 mL round-bottom flask, and ammonia and methanol were distilled away with a rotary evaporator. Through vacuum concentration almost to dryness, the solvent was substituted with toluene such that the solid content concentration of the polymer (IIIA-a-2) was adjusted to 25 wt. %.

In a 500 mL beaker with a stirring bar therein, 100 g of hexane and 50 g of ethyl acetate were mixed. After dripping of a 25 wt. % produced polymer (IIIA-a-2) solution for 10 minutes with a dripping funnel, stirring was performed for 20 minutes, and maturation was performed. The produced white powder was filtered and then returned to the original beaker, to be washed with a mixed solvent of 50 g of hexane and 25 g of ethyl acetate for 20 minutes. The same washing operation was further performed once.

The produced white powder was vacuum-dried to obtain 8.51 g of a polymer (IIIA-a-2). The following GPC measurement results were obtained: Mw=8,000 and Mw/Mn=1.05. On the other hand, in the case in which the reaction was performed in the same manner as in the above-described Example, except that a small amount of water was purposely mixed during polymerization, an extremely small amount of a by-product represented by the following formula (VIIIa) produced due to water that was mixed during polymerization was able to be confirmed by H-NMR in the compound produced through concentration and drying of a filtrate obtained by the purification with a cation exchange resin. From the above fact, even if water is mixed during polymerization, a by-product was able to be removed with a cation exchange resin and a production margin was able to be enlarged.

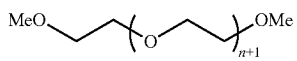
(VIIIa)

[Comparative Synthesis Example 1] Synthesis of Polymer (VIa)

A stirring bar and 71 mg (1.01 mmol) of potassium methoxide (made by Kanto Chemical Co., Ltd.) as a polymerization initiator was placed in a 500 mL four neck round-bottom flask connected to a thermometer, a dripping funnel, and a Dimroth condenser. After the degree of vacuum in the device was held at 10 Pa or less, the internal part of the device was heated with an oil bath and a heat gun, so that the water content in the system was removed.

Subsequently 40 µL (1.00 mmol) of methanol (made by Tokyo Chemical Industry Co., Ltd.) and 140 g of distilled THF were injected in the four neck flask under a nitrogen stream, and the mixture was stirred at room temperature until potassium methoxide was completely dissolved. The ratio of the amounts of substances between potassium methoxide being the polymerization initiator synthesized by the above-described method and methanol being the alcohol that is an initiator raw material is 50:50 (mol %).

Into the dripping funnel, a mixed solution of 35 g of ethylene oxide and 60 g of distilled THF were injected, to be dripped into the four neck flask slowly, with the inner temperature being kept at 35° C. or lower. After dripping of the entire quantity, the mixture was stirred for 80 hours, with the inner temperature being kept at 50° C. or lower.

After confirming no change in conversion ratio of ethylene oxide, 0.06 g of acetic acid was added into the flask. After removal of ethylene oxide by nitrogen bubbling, the reaction liquid was transferred into a 500 mL round-bottom flask and was concentrated with a rotary evaporator until solid precipitated. The crude product of polymer in an amount of 23 g was redissolved in 46 g of toluene, and transferred into a dripping funnel.

Into a 500 mL beaker with a stirring bar therein, 138 g of isopropyl alcohol was injected. After dripping of the polymer solution for 10 minutes with a dripping funnel, maturation was performed for 20 minutes. The produced white powder was filtered and returned to the original beaker, to be washed with a mixed solvent of 69 g of isopropyl ether for 20 minutes. And the same washing operation was further performed twice. A reaction scheme is shown in the following.

The produced white powder was vacuum-dried to obtain 18.54 g of a comparative polymer (VIa). The following GPC measurement results were obtained: Mw=7,200 and Mw/Mn=1.16.

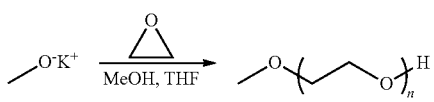
(VIa)

[Comparative Synthesis Example 2] Synthesis of Polymer (IXa)

In a 300 ml four neck flask, 10.00 g of the polymer (VIa), 29.5 g of THF, 0.56 g of 10 wt. % potassium hydroxide aqueous solution, 0.5 g of $H_2O$, and 1.06 g of acrylonitrile were charged, and stirring was performed at normal temperature for 6 hours. After completion of reaction, 1.45 g of an alkaline adsorbent "TOMITA AD 700NS" (product name, synthesized aluminum silicate made by Tomita Pharmaceutical Co., Ltd.) was added, and reaction was performed for 2 hours. After filtration of the alkaline adsorbent, the filtrate was transferred into a 300 mL round-bottom flask, solvent substitution with toluene was performed, and concentration was performed to a solid content concentration of a comparative polymer (IXa) of 25 wt. %.

In a 500 mL beaker with a stirring bar therein, 100 g of hexane and 50 g of ethyl acetate were mixed. After dripping of the concentrated liquid for 10 minutes with a dripping funnel, maturation was performed for 20 minutes. The produced white powder was filtered and then returned to the original beaker, to be washed with a mixed solvent of 50 g of hexane and 25 g of ethyl acetate for 20 minutes. The same washing operation was further performed once. A reaction scheme is shown in the following.

The produced white powder was vacuum-dried to obtain 9.12 g of a comparative polymer (IXa). The following GPC measurement results were obtained: Mw=7,300 and Mw/Mn=1.15.

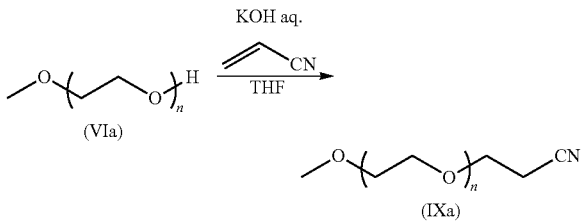

[Comparative Synthesis Example 3] Synthesis of Polymer (IIIc)

Into a 500 mL autoclave for hydrogen reduction, 5.0 g of a polymer (IXa), 5.0 g of Raney cobalt catalyst R-400 (made by Nikko Rica Corporation), 45.0 g of methanol, and 3.0 mL of 1 N methanol solution of ammonia (made by Aldrich) were injected at room temperature. Subsequently, hydrogen gas (pressure: 10 kg/cm$^2$) was provided therein, and the inner temperature was raised to 120° C. for a direct reaction for 6 hours. After cooling to room temperature, the pressure was returned to atmospheric pressure. Subsequently nitrogen was injected to purge ammonia from the system. After removal of the Raney cobalt catalyst by filtration, the filtrate was transferred into a 100 mL round-bottom flask, and ammonia and methanol were distilled away with a rotary evaporator. Through vacuum concentration to dryness, 4.5 g of a mixture of a polymer (IIIc) and the compounds represented by the following formula (IVc) to (VIc) were obtained. The following GPC measurement results were obtained: Mw=7,300 and Mw/Mn=1.25. A reaction scheme and by-products are described in the following.

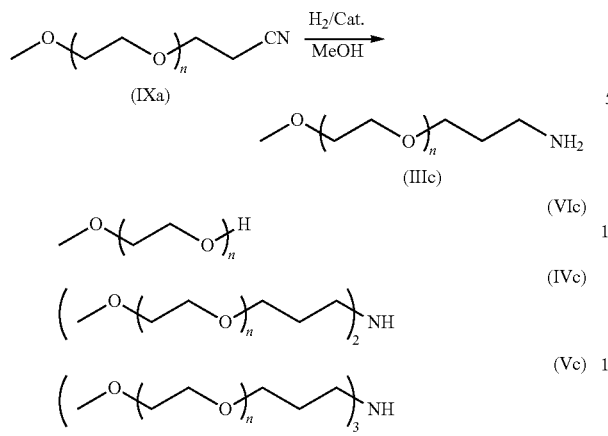

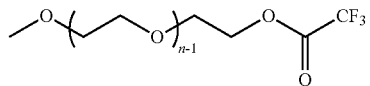

Analysis of Content of Impurities in Products Produced in Synthesis Examples 7-1, 8, and 12 and Comparative Synthesis Example 3

The content of impurities in the product produced in the [Synthesis Example 7-1], [Synthesis Example 8], and [Synthesis Example 12] and in the product produced in the [Comparative Synthesis Example 3] were analyzed. The results are shown in Table 6 below.

A compound represented by "mPEG" in Table 6 is a compound corresponding to the general formula (VIc) in the [Comparative Synthesis Example 3] and is a compound produced through β-elimination of acrylonitrile from a polymer having a cyanoethyl group at an end. The compositional ratio of mPEG was calculated by H-NMR measurement. First of all, each of the products produced in the [Synthesis Example 7-1], [Synthesis Example 8], [Synthesis Example 12], and [Comparative Synthesis Example 3] was weighed at 10 mg, and each was dissolved in 0.75 ml of CDCl3, 50 mg of trifluoroacetic anhydride was then added thereto, and the resultant mixture was left standing for 1 day. The compositional ratio of mPEG was calculated from the ratio between a proton originated from α-methylene of an ester in the compound represented by the general formula (VI-1) produced through the treatment and a proton originated from α-methylene of an amide in the compound represented by the general formula (III-1) also produced from the treatment.

Compounds represented by "secondary and tertiary amines" in Table 6 are compounds corresponding to the general formulas (IVc) and (Vc) in the [Comparative Polymer Synthesis Example 3] respectively. The amount of the compounds mixed was measured by GPC and was calculated from the area percentages of the polymers having twice or three times as large as the molecular weight.

From these results, β-elimination of acrylonitrile and production of secondary and tertiary amines due to hydrogen reduction were observed in the comparative polymer (IIIc), however these by-products were not observed in the example polymers (IIIA-a), (IIIB-a), and (IIIA-a-2).

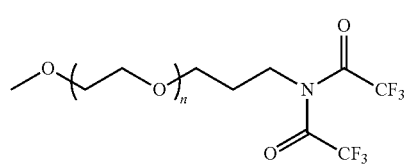

TABLE 6

|  | mPEG | Secondary and tertiary amines |
|---|---|---|
| Polymer (IIIA-a) | <1% | <1% |
| Polymer (IIIB-a) | <1% | <1% |
| Polymer (IIIA-a-2) | <1% | <1% |
| Comparative polymer (IIIc) | 10% | 5% |

Metal Analysis of Products Produced in Synthesis Examples 7-1, 8, and 12, and Comparative Synthesis Example 3

Metal impurities in the products produced in each of the [Synthesis Example 7-1], [Synthesis Example 8], and [Synthesis Example 12], and in the product produced in the [Comparative Synthesis Example 3] were analyzed with a high frequency inductively coupled plasma mass spectrometer (ICP-MS, Agilent Technologies 7500 cs). The analysis was performed by a standard loaded method using samples each obtained by diluting each product with ultrapure water by 100 times for measurement. The analysis results (value obtained in terms of solid content) are shown in Table 7 (in units of ppb).

As a result of the metal analysis, it is revealed that the heavy metal used for reduction is mixed in the comparative polymer (IIIc), but that a heavy metal is not contained in the example polymers (IIIA-a), (IIIB-a) and (IIIA-a-2) of the Examples because a heavy metal catalyst is not used in the [Synthesis Example 7-1], [Synthesis Example 8], and [Synthesis Example 12].

TABLE 7

|  | Co | Ni | Pd | Pt | Rh | Ru | Cu | Cr | K |
|---|---|---|---|---|---|---|---|---|---|
| Polymer (IIIA-a) | <1 | <1 | <1 | <1 | <1 | <1 | <1 | <1 | 7000 |
| Polymer (IIIB-a) | <1 | <1 | <1 | <1 | <1 | <1 | <1 | <1 | 7500 |
| Polymer (IIIA-a-2) | <1 | <1 | <1 | <1 | <1 | <1 | <1 | <1 | 100 |
| Comparative polymer (IIIc) | 200 | <1 | <1 | <1 | <1 | <1 | <1 | <1 | 8000 |

Synthesis of Polymerization Initiator and Comparative Polymerization Initiator, and Comparison of Solubility to Polymerization Solvents Results of synthesizing polymerization initiators (initiators 2 to 9, 11, and 12, and Comparative initiators 1 to 8) other than the polymerization initiators used above are shown in the following. The "initiator 1" below represents the polymerization initiator synthesized with the compound represented by the formula (iA) in the [Synthesis Example 4-1], the polymerization initiator represented by the formula (IA). The "initiator 10" below represents the polymerization initiator (IB) synthesized with the compound represented by the formula (iB) in the [Synthesis Example 8].

Synthesis of Initiator 2

An initiator 2 was synthesized in the same manner as in the method described in the [Synthesis Example 2-3] and [Synthesis Example 4-1], except that ethylene glycol used in the [Synthesis Example 2-3] was changed to diethylene glycol.

Initiator 2

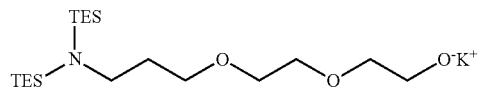

Synthesis of Initiator 3

An initiator 3 was synthesized in the same manner as in the method described in the [Synthesis Example 2-4] and [Synthesis Example 4-1], except that the electrophile (iiB) used in the [Synthesis Example 2-4] was changed to an electrophile (iiC) below.

Electrophile (iiC)

Initiator 3

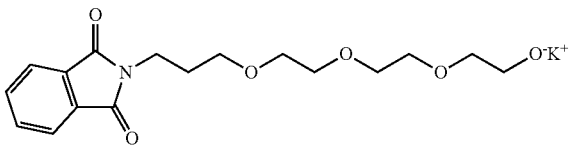

Synthesis of Initiator 4

An initiator 4 was synthesized in the same manner as in the method described in the [Synthesis of Initiator 3], except that ethylene glycol used in the [Synthesis Example 2-4] was changed to diethylene glycol.

Initiator 4

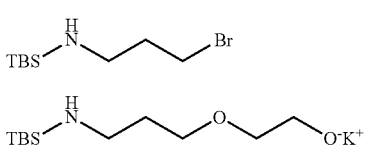

Synthesis of Initiator 5

An initiator 5 was synthesized in the same manner as in the method described in the [Synthesis Example 2-4] and [Synthesis Example 4-1], except that the electrophile (iiB) used in the [Synthesis Example 2-4] was changed to an electrophile (iiD) below, and ethylene glycol was changed to triethylene glycol.

Electrophile (iiD)

Initiator 5

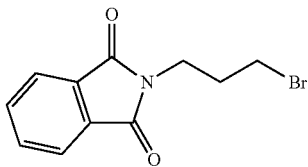

Synthesis of Initiator 6

An initiator 6 was synthesized in the same manner as in the method described in the [Synthesis Example 2-4] and [Synthesis Example 4-1], except that the electrophile (iiB) used in the [Synthesis Example 2-4] was changed to an electrophile (iiE) below.

Electrophile (iiE)

Initiator 6

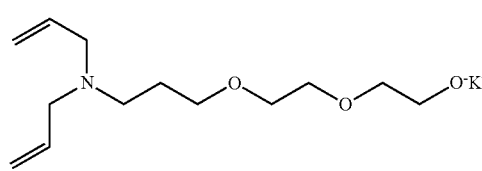

In the electrophile (iiE) and the initiator 6, "TBS" means tert-butyldimethylsilyl

Synthesis of Initiator 7

An initiator 7 was synthesized in the same manner as in the method described in the [Synthesis Example 2-4] and [Synthesis Example 4-1], except that the electrophile (iiB) used in the [Synthesis Example 2-4] was changed to an electrophile (iiF) below.

Electrophile (iiF)

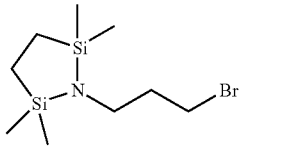

Initiator 7

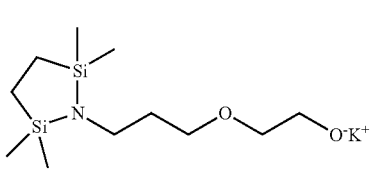

Synthesis of Initiator 8

An initiator 8 was synthesized in the same manner as in the method described in the [Synthesis Example 2-4] and [Synthesis Example 4-1], except that the electrophile (iiB) used in the [Synthesis Example 2-4] was changed to an electrophile (iiG) below.

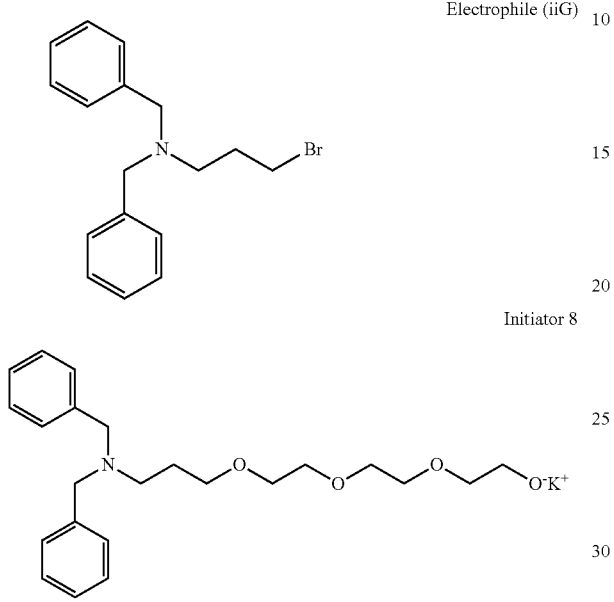

Synthesis of Initiator 9

An initiator 9 was synthesized in the same manner as in the method described in the [Synthesis Example 2-4] and [Synthesis Example 4-1], except that the electrophile (iiB) used in the [Synthesis Example 2-4] was changed to an electrophile (iiH) below.

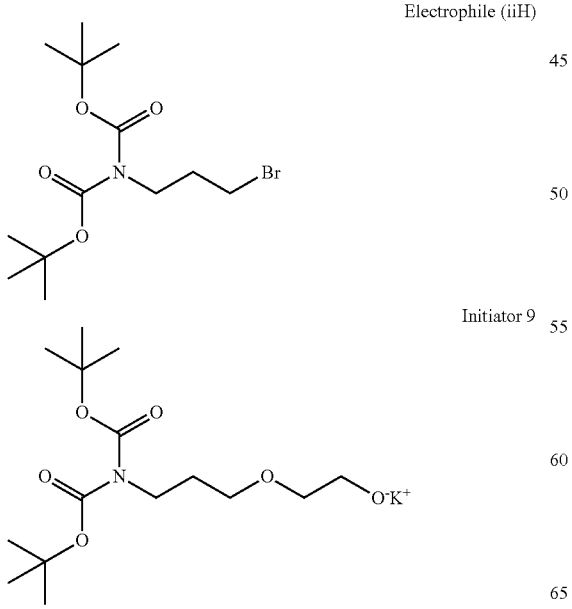

Synthesis of Initiator 11

In a 300 ml three neck flask, 15.7 g of 6-amino-1-hexanol, 91.0 g of THF, and 46.3 g of potassium carbonate were charged, and 28.4 ml of allyl bromide was then dripped therein while the flask was ice-cooled under a nitrogen atmosphere. Stirring was then performed at nornial temperature for 1 hour. The reaction liquid was filtered and distilled under reduced pressure, so that 13.2 g (yield rate 50.0%) of a raw material alcohol (iC) for a polymerization initiator 11 was produced. Subsequently, the polymerization initiator 11 was synthesized in the same manner as in the method described in the [Synthesis Example 4-1].

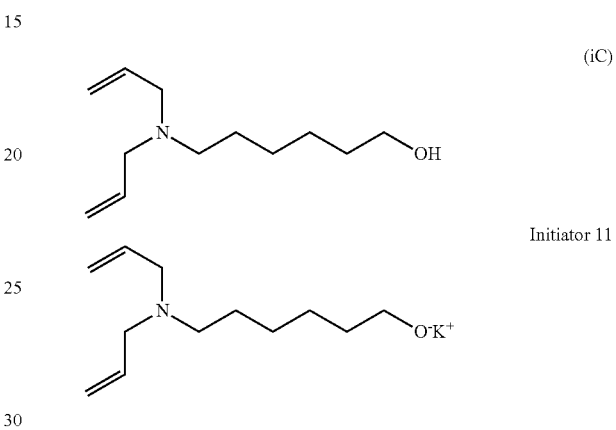

Synthesis of Initiator 12

An initiator 12 was synthesized in the same manner as in the [Synthesis of Initiator 11], except that allyl bromide was changed to 1,2-bis(chlorodimethylsilyl)ethane.

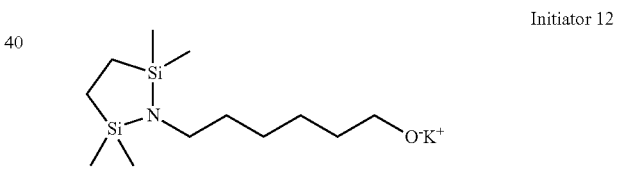

Synthesis of Comparative Initiator 1

A comparative initiator 1 was synthesized in the same manner as in the method described in the [Synthesis Example 4-1] using the silyl-protected amino group-containing alcohol (iiA-2) as a raw material.

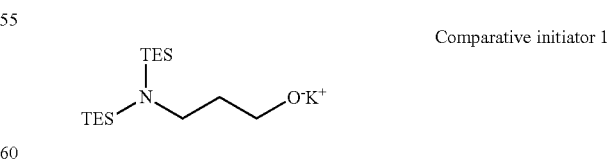

Synthesis of Comparative Initiator 2

A comparative initiator 2 was synthesized in the same manner as in the method described in the [Synthesis of Comparative Initiator 1], except that triethylsilyl as a protective group was changed to trimethylsilyl (TMS).

Comparative initiator 2

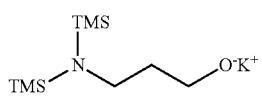

In the comparative initiator 2, TMS means trimethylsilyl.

Synthesis of Comparative Initiator 3

A comparative initiator 3 was synthesized in the same manner as in the method described in the [Synthesis of Initiator 11], except that 6-amino-1-hexanol used in the [Synthesis of Initiator 11] was changed to 3-amino-1-propanol.

Comparative initiator 3

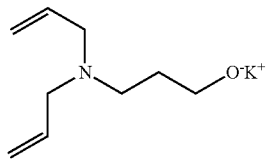

Synthesis of Comparative Initiator 4

A comparative initiator 4 was synthesized in the same manner as in the method described in the [Synthesis Example 4-1], except that the compound represented by the formula (iD) below was used as a raw material alcohol in place of the compound represented by the formula (iA).

(iD)

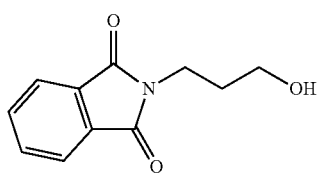

Comparative initiator 4

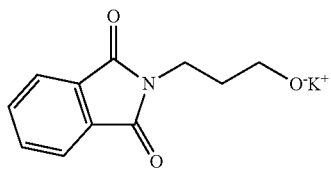

Synthesis of Comparative Initiator 5

A comparative initiator 5 was synthesized in the same manner as in the method described in the [Synthesis Example 4-1], except that the compound represented by the formula (iE) below was used as a raw material alcohol in place of the compound represented by the formula (iA).

(iE)

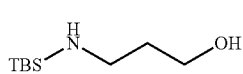

Comparative initiator 5

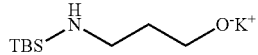

Synthesis of Comparative Initiator 6

A comparative initiator 6 was synthesized in the same manner as in the method described in the [Synthesis of Initiator 12], except that 6-amino-1-hexanol used in the [Synthesis of Initiator 12] was changed to 3-amino-1-propanol.

Comparative initiator 6

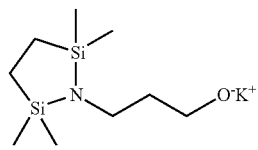

Synthesis of Comparative Initiator 7

A comparative initiator 7 was synthesized in the same manner as in the method described in the [Synthesis of Comparative Initiator 3], except that allyl bromide used in the [Synthesis of Comparative Initiator 3] was changed to benzyl bromide.

Comparative initiator 7

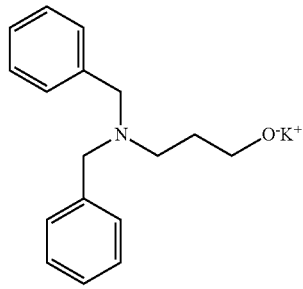

Synthesis of Comparative Initiator 8

A compound represented by the following formula (iF) was synthesized through the reaction shown in scheme 1 below. A comparative initiator 8 was synthesized in the same manner as in the method described in the [Synthesis Example 4-1], except that the compound represented by the formula (iF) was used in place of the compound represented by the formula (iA).

1) Synthesis of Boc-Protected Compound (iF-1)

In a 200 ml three neck flask, 5.11 g of 3-amino-1-propanol, 7.21 g of triethylamine, 55.43 g of methanol, and 15.61 g of di-tert-butyl dicarbonate (hereinafter, written as Boc2O), and stirring was performed under nitrogen atmosphere at normal temperature for 14 hours. The reaction of the reaction liquid was stopped with a saturated ammonium chloride aqueous solution, and extraction with ethyl acetate was performed. The obtained ethyl acetate solution was concentrated under reduced pressure, so that 10.73 g of a Boc-protected compound (iF-1) was produced (crude yield rate 90%).

2) Synthesis of TBS-Protected Compound (iF-2)

In a 500 ml three neck flask, 10.61 of the Boc-protected compound (iF-1), and 241.80 g of THF were added, and then 9.26 g of imidazole, 15.38 g of TBSCl were added thereto while the flask was ice-cooled under a nitrogen atmosphere. The temperature was brought back to normal temperature, stirring was then performed for 22 hours, and thereafter, the reaction was stopped with a saturated ammonium chloride aqueous solution, and extraction with isopropyl ether was performed. The obtained isopropyl ether solution was concentrated under reduced pressure, so that 18.24 g of a TBS-protected compound (iF-2) was produced (crude yield rate 93%).

3) Synthesis of Boc-Protected Compound (iF-3)

In a 500 ml two neck flask, 10.01 g of the TBS-protected compound (iF-2), and 155.58 g of dehydrated THF were added, and 16.68 mL of an n-butyllithium/hexane solution (2.69 M) was dripped therein while the flask was ice-cooled under a nitrogen atmosphere. After stirring was performed at the same temperature, 40.87 g of a Boc2O/THF solution (26 wt. %) was dripped, the temperature was then brought back to normal temperature, and stirring was performed for 2.5 hours. The reaction solution was diluted with isopropyl ether, to be washed with a saturated ammonium chloride aqueous solution, and the obtained solution was then concentrated under reduced pressure, so that 14.77 g of a TBS-protected compound (iF-3) was produced (crude yield rate 100%).

4) Synthesis of Alcohol (iF)

In a 500 ml three neck flask, 14.77 g of the TBS-protected compound (iF-3) and 110.59 g of THF were charged, and, under nitrogen atmosphere, 39.5 mL of a TBAF (tetra-n-butylammonium fluoride)/THF solution was added thereto under stirring at normal temperature. After stirring was performed at the same temperature for 5 hours, the reaction solution was diluted with isopropyl ether, to be washed with ultrapure water. The obtained isopropyl ether solution was concentrated under reduced pressure, so that 10.22 g of an alcohol (iF) was produced (crude yield rate 98%).

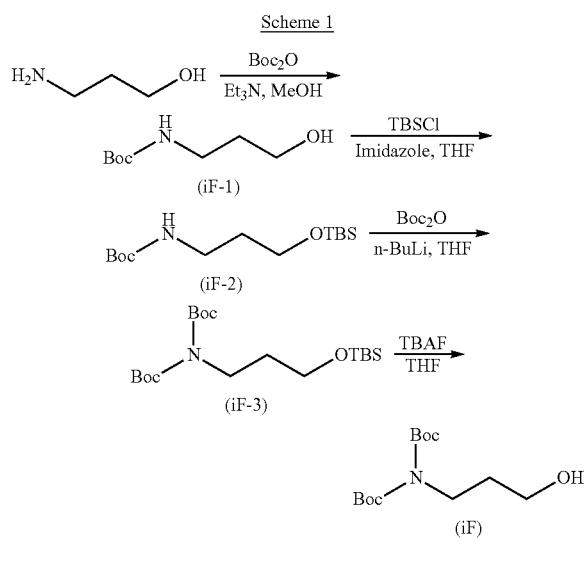

In the scheme, Boc means tert-butoxycarbonyl

The structures of the various polymerization initiators (initiators 1 to 12 and comparative initiators 1 to 8) synthesized above are shown together below.

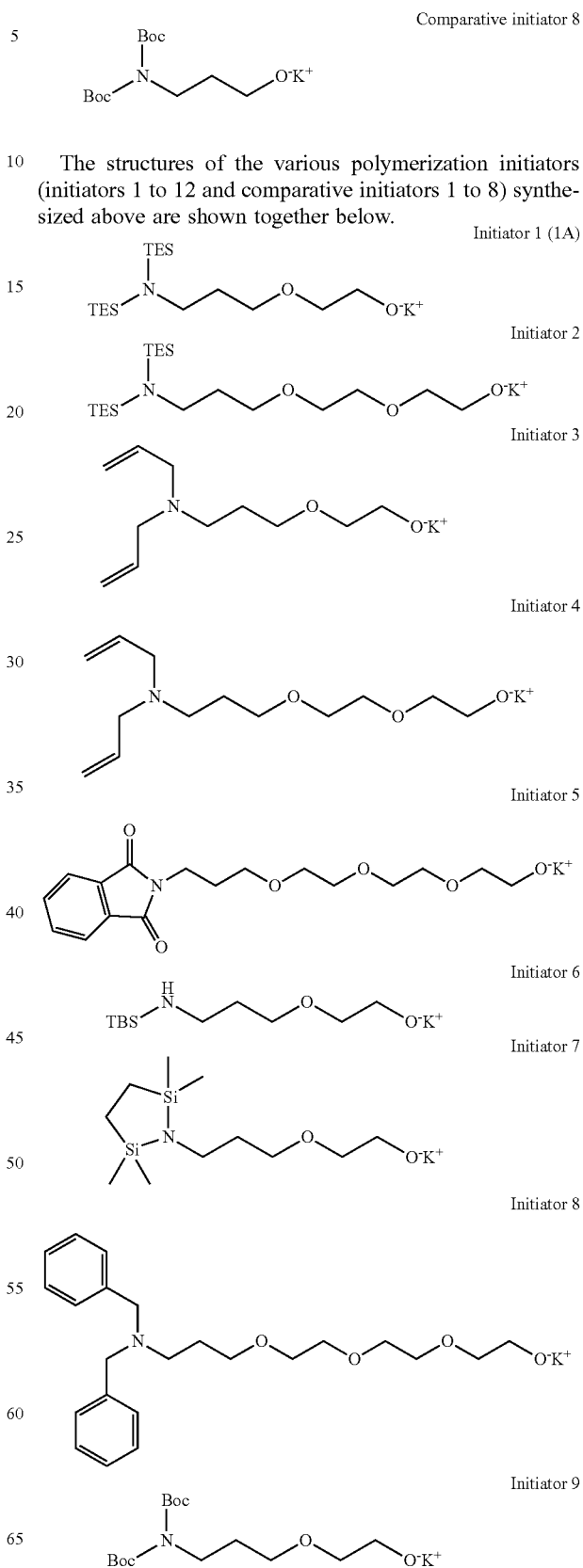

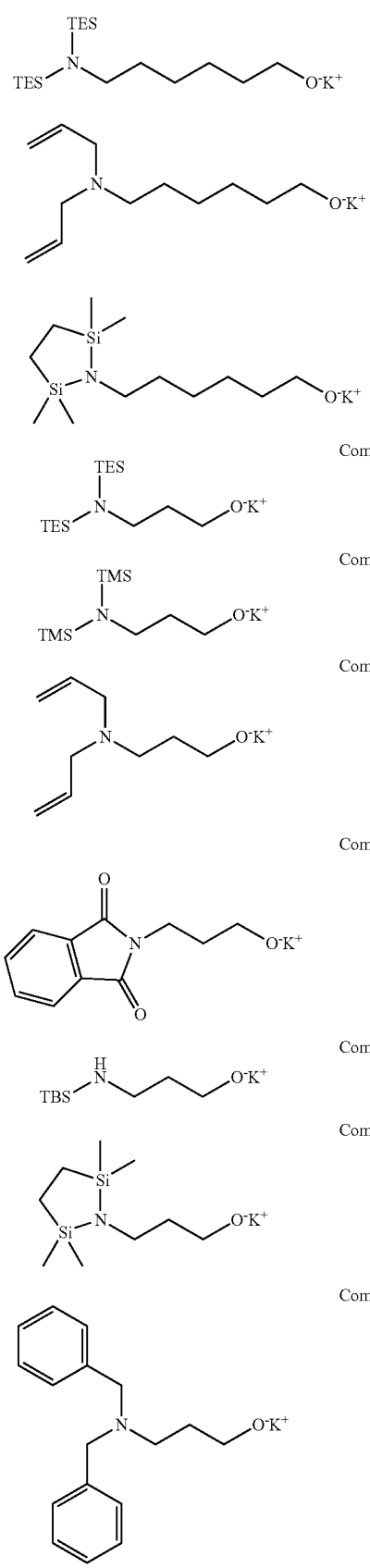

Results of solubility of the initiators 1 to 12 and comparative initiators 1 to 8 to polymerization solvents are shown below. THF in each of the products of the initiators 1 to 12 and the comparative initiators 1 to 8 synthesized above was distilled away under reduced pressure to extract the polymerization initiators. The results obtained by dissolving each polymerization initiator in each polymerization solvent at a concentration of 20 wt. % are shown. In the case in which cloudiness was not observed at all in the solution by visual observation, the initiator was shown as "excellent"; in the case in which cloudiness was observed or the initiator did not dissolve at all, or in the case in which the initiator decomposed when the alkoxide was formed from the initiator, the initiator was shown as "poor"; and the initiator for which solubility was not checked was shown as "–".

TABLE 8

|  |  | THF | Toluene |
|---|---|---|---|
| Initiators | 1 | Excellent | — |
|  | 2 | Excellent | — |
|  | 3 | Excellent | — |
|  | 4 | Excellent | — |
|  | 5 | Excellent | — |
|  | 6 | Excellent | — |
|  | 7 | Excellent | — |
|  | 8 | Excellent | — |
|  | 9 | Excellent | — |
|  | 10 | — | Excellent |
|  | 11 | — | Excellent |
|  | 12 | — | Excellent |
| Comparative initiators | 1 | Poor | Poor |
|  | 2 | Poor | Poor |
|  | 3 | Poor | Poor |
|  | 4 | Poor | Poor |
|  | 5 | Poor | Poor |
|  | 6 | Poor | Poor |
|  | 7 | Poor | Poor |
|  | 8 | Poor | Poor |

In studying the synthesis of the comparative initiators 1, 2, 5, and 6, changes in the position protected by a protective group progressed. On the other hand, in the initiators 1, 2, 6, 7, 10, and 12 in which chain lengths were extended, the initiators stably existed and dissolved in the solvent. In addition, the comparative initiators 3, 4, 7, and 8 did not dissolve in the solvents. On the other hand, the initiators 3, 4, 5, 8, 9, and 11, in which the chain lengths were extended, dissolved in a solvent.

From the results of the above-described Examples and Comparative Examples, it is revealed that, in the [Synthesis Example 5] and in the [Comparative Synthesis Example 1], the latter requires a long polymerization time, as long as 80 hours, due to the presence of an alcohol as an initiator raw material, and that, in the former, the polymerization reaction is completed within 8 hours by using an initiator that is soluble in THF even in a state in which the amount of residual alcohol as an initiator raw material is small. That is to say, the polymerization of an alkylene oxide under mild conditions was realized by the method of the present invention. Moreover, by using the reaction liquid in the Synthesis Example 5, without performing post-treatment, directly to the reaction in the subsequent step in the Synthesis Example 6, the process was able to be substantially simplified. Furthermore, by using an organic solvent for purifying a resin with an ion exchange resin in the Synthesis Example 12, it became possible to purify a polymer by a simple method without using freeze dry in the final process.

In the [Synthesis Examples 5 to 8] and the [Comparative Examples 1 to 3], hydrogenation reaction using a heavy metal as a catalyst is required for reducing a cyano group in the latter; however, in the former, the target polymer can be synthesized only by deprotecting the protected amino group. In the comparative polymer (Inc), β-elimination of acrylonitrile and production of secondary and tertiary amines occurred through hydrogen reduction; however, in the example polymers (IIIA-a), (IIIB-a), and (IIIA-a-2), production of any one of them was not observed (Table 6). Moreover, from the results of metal analysis, it is revealed that, in the [Synthesis Examples 7-1, 8, and 12], and in the [Comparative Synthesis Example 3], the heavy metal used for reduction is mixed in the comparative polymer, but that a heavy metal is not substantially mixed in the example polymers because a heavy metal is not used in the [Synthesis Examples 7-1, 8, and 12]. Moreover, the amount of a potassium metal mixed was able to be reduced by the purification with a strong acid cation exchange resin (Table 7). As a result thereof, synthesis of a narrowly distributed and amino group-containing polyalkylene glycol derivative without mixing of a heavy metal that could cause adverse effects in medical supplies was able to be achieved by the present invention. Moreover, novel protected amino-group containing alcohols were synthesized, and further, polymerization initiators were produced using the alcohols as a raw material, and thereby it became possible to apply the polymerization initiators for synthesis of various polymers. By using the novel polymerization initiators, and further performing purification with a cation exchange resin as needed, it became possible to remove diol polymers produced due to mixing of water and that had been difficult to separate, thereby making it possible to produce narrowly distributed amino group-containing polyalkylene glycol derivatives with high purity to enlarge a production margin.

Polymer compounds produced using the method of the present invention can widely be used as a starting raw material in synthesizing block copolymers for use in medical supplies and cosmetic products including a field of drug delivery systems. Moreover, metal salts of novel protected amino group-containing alcohols can be applied to synthesis of various polymers.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A silyl-protected amino group-containing alcohol compound of formula (6) or (7):

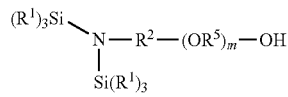

(6)

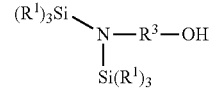

(7)

wherein each $R^1$ independently is a linear monovalent hydrocarbon group having 1 to 6 carbon atoms, or a branched or cyclic monovalent hydrocarbon group having 3 to 6 carbon atoms, or $R^1$ may bind to each other to form a 3 to 6 membered ring together with a silicon atom having bonds with $R^1$;

$R^2$ is a linear divalent hydrocarbon group having 1 to 6 carbon atoms, or a branched or cyclic divalent hydrocarbon group having 3 to 6 carbon atoms;

$R^3$ is a linear divalent hydrocarbon group having 4 to 6 carbon atoms;

$R^5$ is an alkylene group having 2 to 8 carbon atoms, and $R^5$ is not the same as $R^2$; and m is an integer of 1 to 3.

2. A metal salt of a silyl-protected amino group-containing alcohol compound of formula (1) or (2):

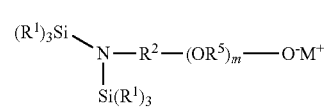

(1)

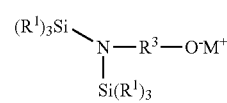

(2)

wherein each $R^1$ independently is a linear monovalent hydrocarbon group having 1 to 6 carbon atoms, or a branched or cyclic monovalent hydrocarbon group having 3 to 6 carbon atoms, or $R^1$ may bind to each other to form a 3 to 6 membered ring together with a silicon atom having bonds with $R^1$;

$R^2$ is a linear divalent hydrocarbon group having 1 to 6 carbon atoms, or a branched or cyclic divalent hydrocarbon group having 3 to 6 carbon atoms;

$R^3$ is a linear divalent hydrocarbon group having 4 to 6 carbon atoms;

$R^5$ is an alkylene group having 2 to 8 carbon atoms, and $R^5$ is not the same as $R^2$;

M is an alkali metal; and m is an integer of 1 to 3.

3. A polyalkylene compound derivative having a protected amino group of formula (II-1) or (II-2):

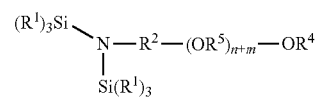

(II-1)

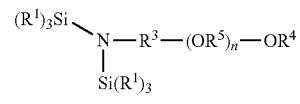

(II-2)

wherein each $R^1$ independently is a linear monovalent hydrocarbon group having 1 to 6 carbon atoms, or a branched or cyclic monovalent hydrocarbon group having 3 to 6 carbon atoms, or $R^1$ may bind to each other to form a 3 to 6 membered ring together with a silicon atom having bonds with $R^1$;

$R^2$ is a linear divalent hydrocarbon group having 1 to 6 carbon atoms, or a branched or cyclic divalent hydrocarbon group having 3 to 6 carbon atoms;

$R^3$ is a linear divalent hydrocarbon group having 4 to 6 carbon atoms;

$R^4$ is a hydrogen atom, or a linear, branched, or cyclic hydrocarbon group that may be substituted, the hydrocarbon group having 1 to 12 carbon atoms, and the hydrocarbon group may contain a heteroatom;

$R^5$ is an alkylene group having 2 to 8 carbon atoms, and $R^5$ is not the same as $R^2$;

m is an integer of 1 to 3; and n is an integer of 1 to 450.

* * * * *

UNITED STATES PATENT AND TRADEMARK OFFICE
CERTIFICATE OF CORRECTION

PATENT NO. : 10,472,377 B2
APPLICATION NO. : 15/621272
DATED : November 12, 2019
INVENTOR(S) : Suka et al.

It is certified that error appears in the above-identified patent and that said Letters Patent is hereby corrected as shown below:

On the Title Page

Item (56) References Cited, OTHER PUBLICATIONS, Page 2, Column 2, Lines 21 and 22, Extended European Search Report of Aug. 29, 2018: Please correct "No. 18186866.3" to read -- No. 18185866.3 --

Item (56) References Cited, OTHER PUBLICATIONS, Page 2, Column 2, Lines 23 and 24, Extended European Search Report of Aug. 24, 2018: Please correct "No. 18165868.9" to read -- No. 18185868.9 --

In the Specification

Column 5, Line 11: Please correct "$R_A^4 OR_A^5)_k L$" to read -- $R_A^4(OR_A^5)_k L$ --

Column 8, Line 10: Please correct "$R_A^{13}$" to read -- $R_A^{1a}$ --

Column 10, Line 23: Please correct "ap-tolyl" to read -- a p-tolyl --

Column 10, Line 39: Please correct "$-(OR_A^5)_p-$" to read -- $-(OR_A^5)_p-$ --

Column 10, Line 56: Please correct "atom-(oxygen" to read -- atom (oxygen --

Column 11, Line 6: Please correct "ap-tolyl" to read -- a p-tolyl --

Column 16, Line 19: Please correct "$[R_Y]^-$" to read -- $[R_Y]^- M^+$ --

Column 16, Line 23: Please correct "$R_y$" to read -- $R_Y$ --

Column 28, Line 6: Please correct "$HN-(-R_A^2-R_A^3-(OR_A^5)_n-OR_A^5)_2$" to read -- $HN-(-R_A^2-R_A^3-(OR_A^5)_n-OR_A^4)_2$ --

Signed and Sealed this
Tenth Day of March, 2020

Andrei Iancu
*Director of the United States Patent and Trademark Office*

CERTIFICATE OF CORRECTION (continued)
U.S. Pat. No. 10,472,377 B2

Column 40, Line 29: Please correct "R'" to read -- R$^1$ --

Column 40, Line 33: Please correct "MSCl" to read -- MsCl --

Column 40, Line 50: Please correct "MSCl" to read -- MsCl --

Column 47, Line 57: Please correct "25" to read -- 25 µl --

Column 49, Lines 26-30, (iiA-1): Please correct " 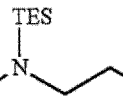 " to read  -- 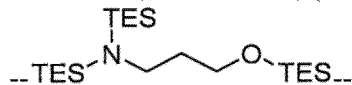 --

Column 49, Lines 55-60, (iiA-1): Please correct " 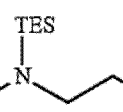 " to read -- 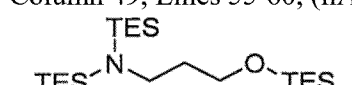 --

Column 52, Line 26: Please correct "8=0.63" to read -- δ=0.63 --

Column 60, Line 62: Please correct "(Villa)" to read -- (VIIIa) --

Column 75, Line 12: Please correct "(Inc)" to read -- (IIIc) --